(12) United States Patent
Kolandaivelu et al.

(10) Patent No.: US 10,318,707 B2
(45) Date of Patent: Jun. 11, 2019

(54) MULTI-PARAMETER THROMBOTIC ASSAY APPARATUS, SYSTEMS, AND METHODS

(71) Applicant: MASSACHUSETTS INSTITUTE OF TECHNOLOGY, Cambridge, MA (US)

(72) Inventors: Kumaran Kolandaivelu, Newton, MA (US); Elazer R. Edelman, Brookline, MA (US)

(73) Assignees: Massachusetts Institute of Technology, Cambridge, MA (US); The Brigham and Women's Hospital, Inc., Boston, MA (US)

( * ) Notice: Subject to any disclaimer, the term of this patent is extended or adjusted under 35 U.S.C. 154(b) by 1349 days.

(21) Appl. No.: 14/266,954

(22) Filed: May 1, 2014

(65) Prior Publication Data

US 2014/0236494 A1  Aug. 21, 2014

Related U.S. Application Data

(63) Continuation of application No. PCT/US2012/063613, filed on Nov. 5, 2012.

(60) Provisional application No. 61/555,691, filed on Nov. 4, 2011.

(51) Int. Cl.
| | |
|---|---|
| *G01N 33/48* | (2006.01) |
| *G06F 19/26* | (2011.01) |
| *G01N 33/49* | (2006.01) |
| *G01N 33/86* | (2006.01) |

(52) U.S. Cl.
CPC ......... *G06F 19/26* (2013.01); *G01N 33/4905* (2013.01); *G01N 33/86* (2013.01); *G01N 2800/226* (2013.01)

(58) Field of Classification Search
CPC ..... G06F 19/26; G01N 33/4905; G01N 33/86
See application file for complete search history.

(56) References Cited

FOREIGN PATENT DOCUMENTS

WO      2007113804 A2      10/2007

OTHER PUBLICATIONS

Echenique, Javier, "Thrombotic Fingerprints for the Enhanced Prediction of Thrombosis" Dissertation, Jun. 1, 2007, pp. 1-137. (Year: 2007).*

(Continued)

*Primary Examiner* — Larry D Riggs, II
(74) *Attorney, Agent, or Firm* — Eversheds Sutherland (US) LLP

(57) ABSTRACT

Apparatus, systems, and methods are provided for assessing clot activity in blood under various conditions in vitro. The apparatus includes a plurality of test receptacles that receive the blood, at least one flow generating mechanism in communication with the test receptacles, and a clot detector configured to analyze an amount of clot formation that occurs within the blood in each receptacle. Blood contacting surfaces of a first subset of the test receptacles are coated with a first surface substrate and blood contacting surfaces of a second subset of the test receptacles are coated with a different second surface substrate. The flow generating mechanism is configured to generate a first blood flow rate through a third subset of the test receptacles and to generate a different second blood flow rate through a fourth subset of the test receptacles.

18 Claims, 41 Drawing Sheets

(56) References Cited

OTHER PUBLICATIONS

Kolandaivelu et al., (J Biomed Mater Res. A. 2004.70(2):186-93). (Year: 2004).*

K. Kolandaivelu, "Multi-Parameter Assay for Personalized Targeting and Monitoring of Anti-Thrombotic Therapy—Presentation", CIMIT, Center for Integration of Medicine & Innovative Technology, Mar. 17, 2009.

Echenique, Javier, "Thrombotic Fingerprints for the Enhanced Prediction of Thrombosis", Dissertion, Jun. 1, 2007, pp. 1-137.

Conant, C.G., et al., "Well Plate Microfluidic System for Investigation of Dynamic Platelet Behavior Under Variable Shear Loads", Biotechnology and Bioengineering, vol. 108, No. 12, Dec. 2011.

International Search Report and Written Opinion for PCT/US2012/063613, dated Apr. 17, 2013.

Kolandaivelu, K. and E.R. Edelman, "Low Background, Pulsatile, In Vitro Flow Circuit for Modeling Coronary Implant Thrombosis", J. Biomech Eng. 2002. 124(6): p. 662-8.

Kolandaivelu, K. and E.R. Edelman, "Environmental Influences on Endovascular Stent Platelet Reactivity: An in vitro Comparison of Stainless Steel and Gold Surfaces", J. Biomed Mater Res. A., 2004. 70(2): p. 186-93.

Basmadjian, D., "The Effect of Flow and Mass Transport in Thrombogenesis", Ann Biomed Eng. 1990. 18(6): p. 685-709.

Beythien, C. W., et al., "In vitro Model to Test the Thrombogenicity of Coronary Stents",. Thromb Res. 1994. 75(6): p. 581-90.

Vats, H.S., et al., "Suspected Clopidogrel Resistance in a Patient with Acute Stent Thrombosis", Nature Clinical Practice CM, 2006; 3:226-230.

Lordkipanidze, M., et al. "A Comparison of Six Major Platelet Function Tests to Determine the Prevalence of Aspirin Resistance in Patients with Stable Coronary Artery Disease", European Heart Journal, (2007); 28 (14):1702-1708.

Gurbel, P.A., et al. "The Relation of Dosing to Clopidogrel Responsiveness and the Incidence of High Post-Treatment Platelet Aggregation in Patients Undergoing Coronary Stenting", Journal of the American College of Cardiology 2005; vol. 45: No. 9. pp 1392-1346.

Samama, M., et al. "Clinical Aspects and Laboratory Problems in Hereditary Thombophilia", Haemostasis, 1999; 29(2-3): pp. 76-99.

Iakovou I., "A Simple Risk Score for Prediction of Thrombosis After Drug-Eluting Stent Implantation", ESC 2005 Abstract 3749.

Gardner, R.A., "An Examination of the Fluid Mechanics and Thrombus Formation Time Parameters in a Chandler Rotating Loop System", J. Lab Clin. Med. 1974. 84(4): pp. 494-508.

* cited by examiner

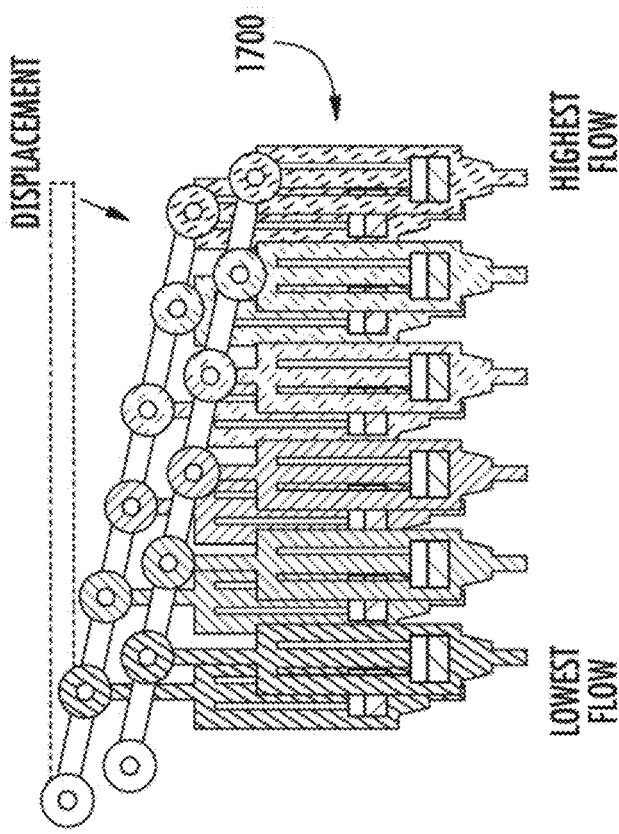
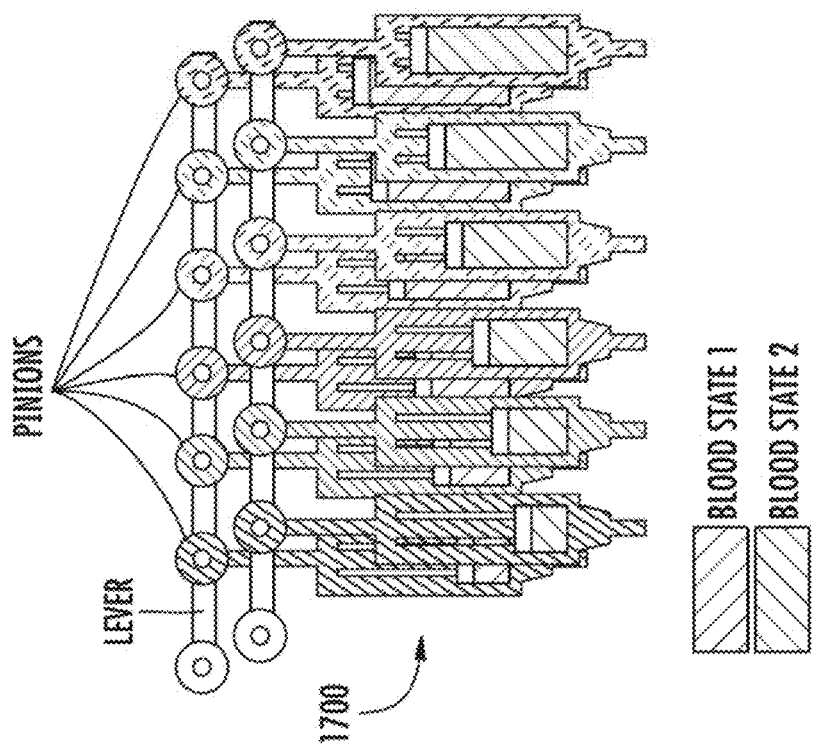
FIG. 17A
FIG. 17B

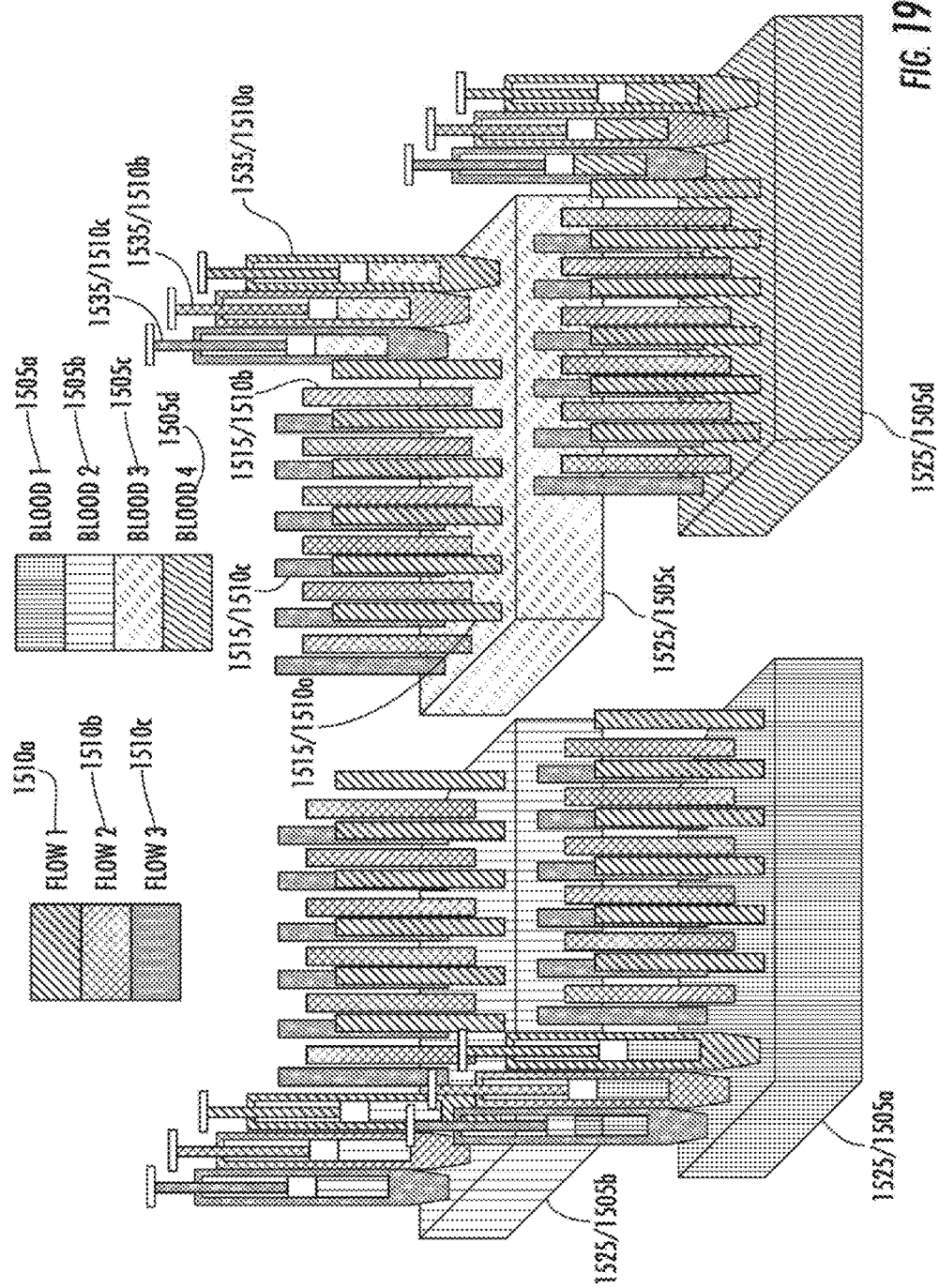

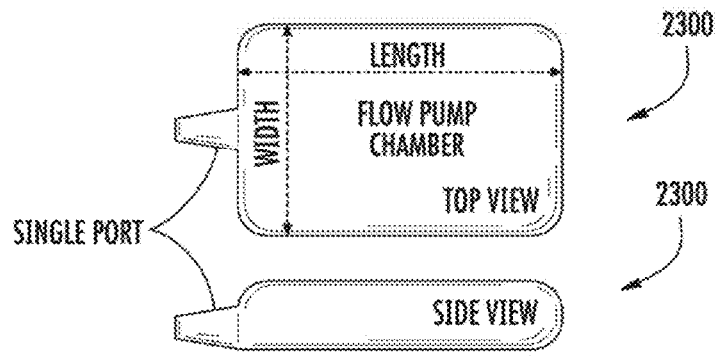
FIG. 23A
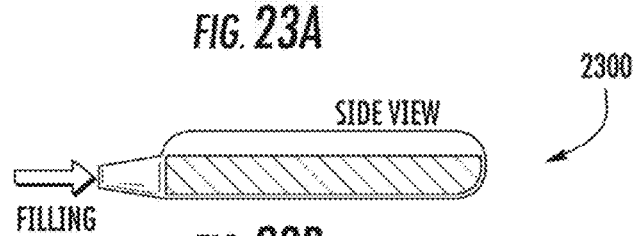
FIG. 23B
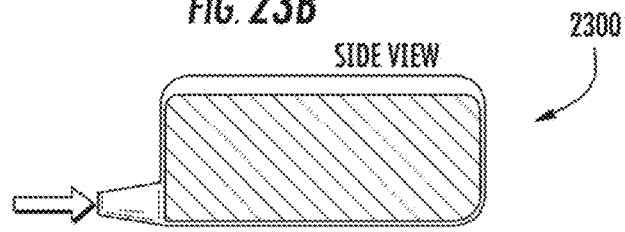
FIG. 23C
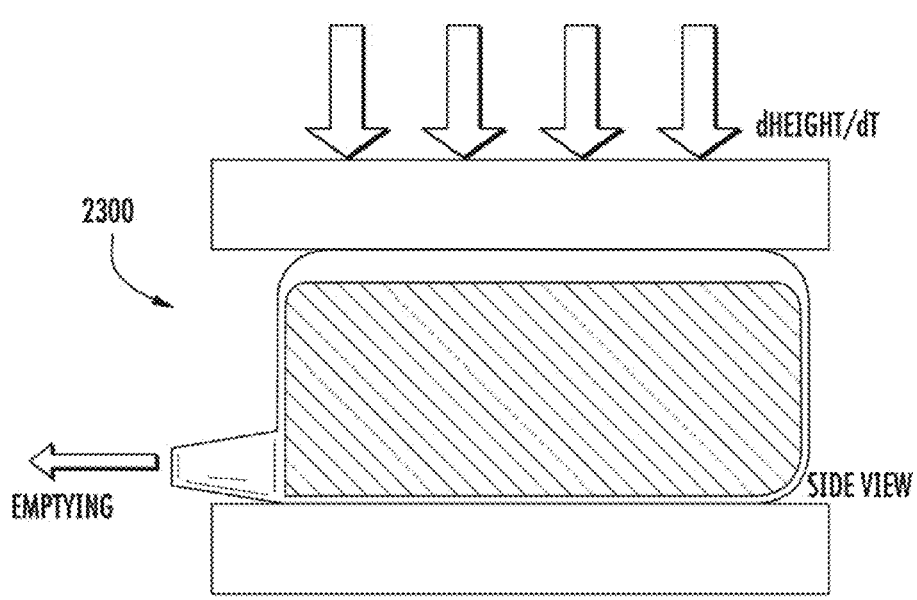
FLOW = LENGTH X WIDTH X dHEIGHT/dT    FIG. 23D

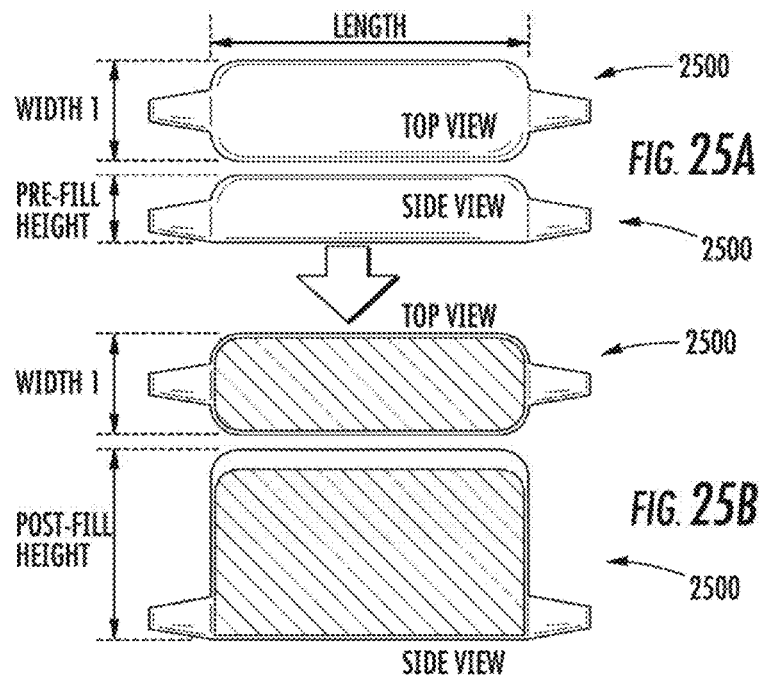
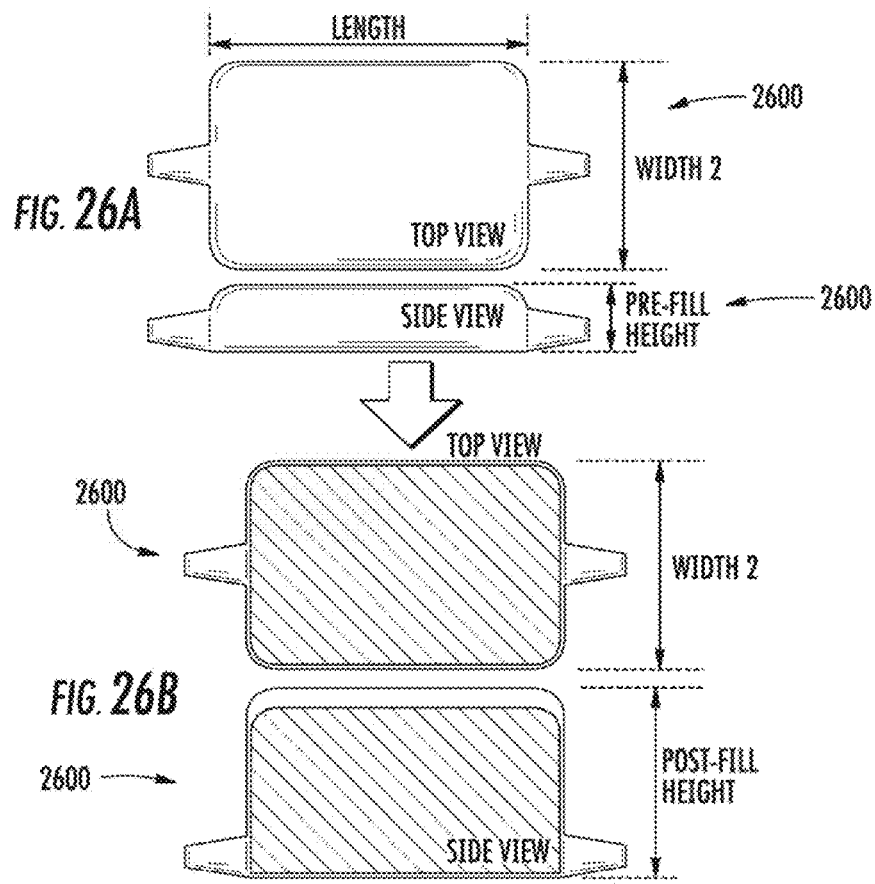

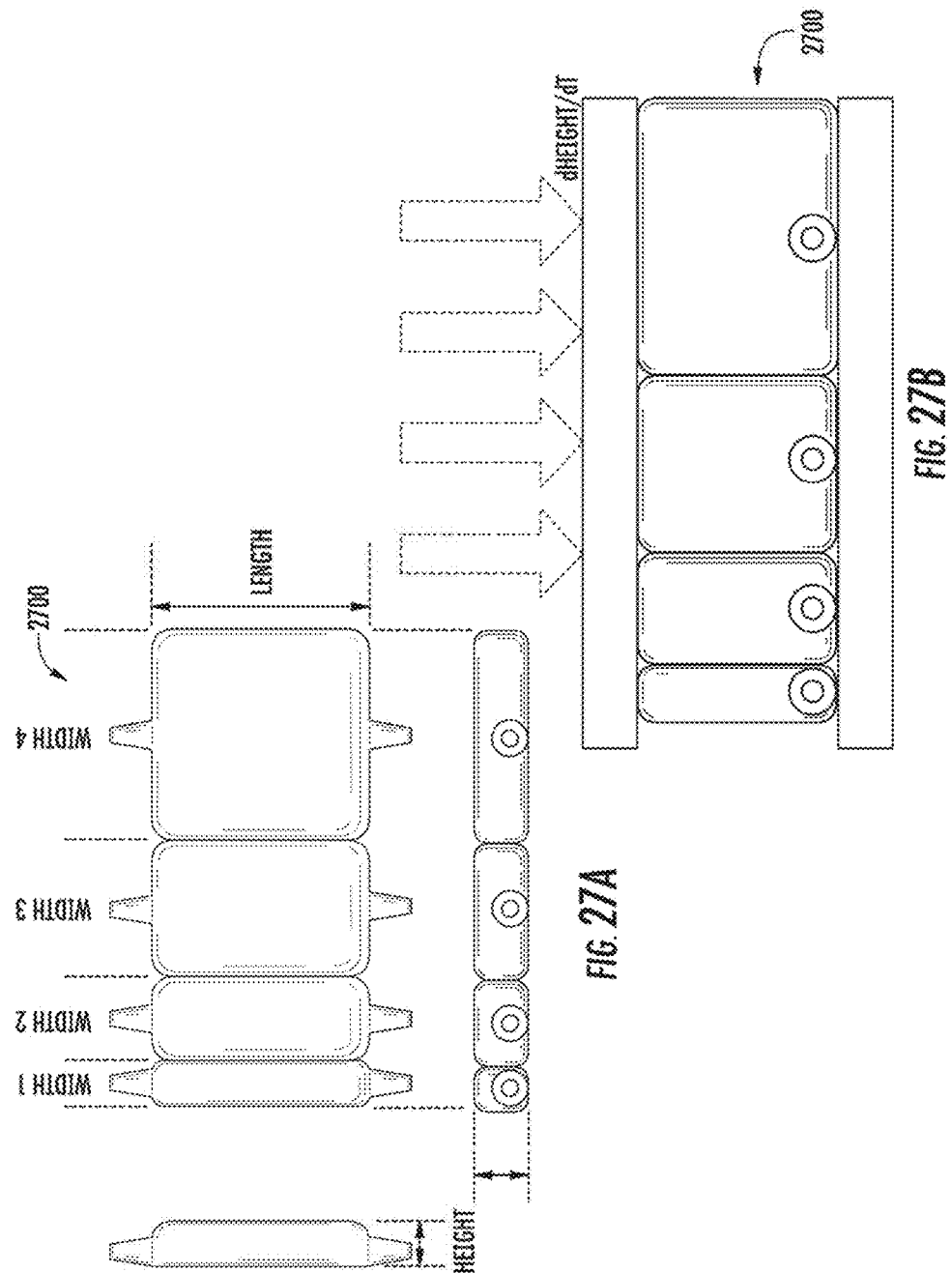

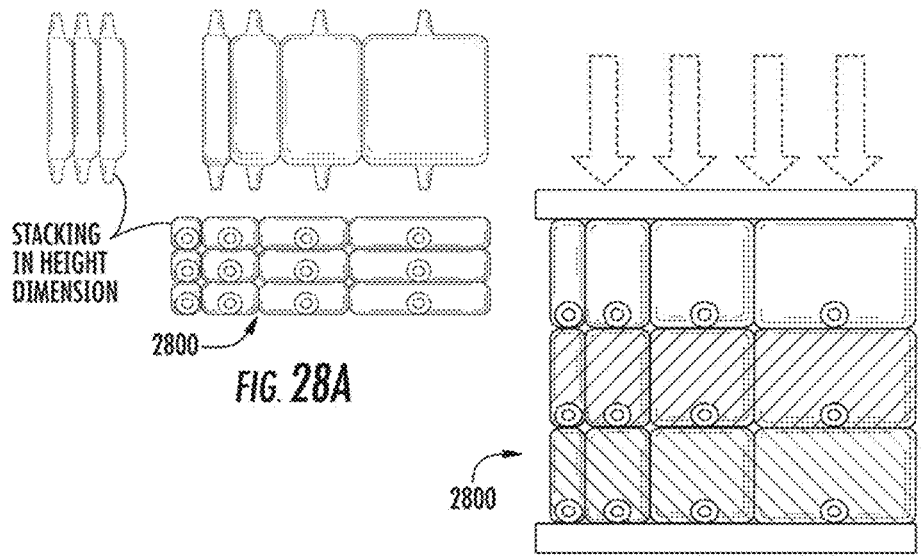
FIG. 28A
FIG. 28B
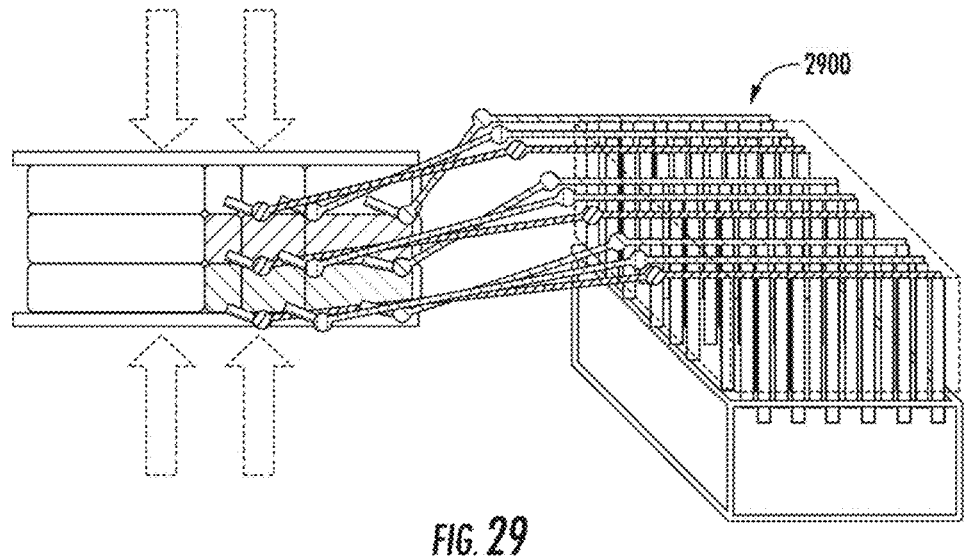
FIG. 29

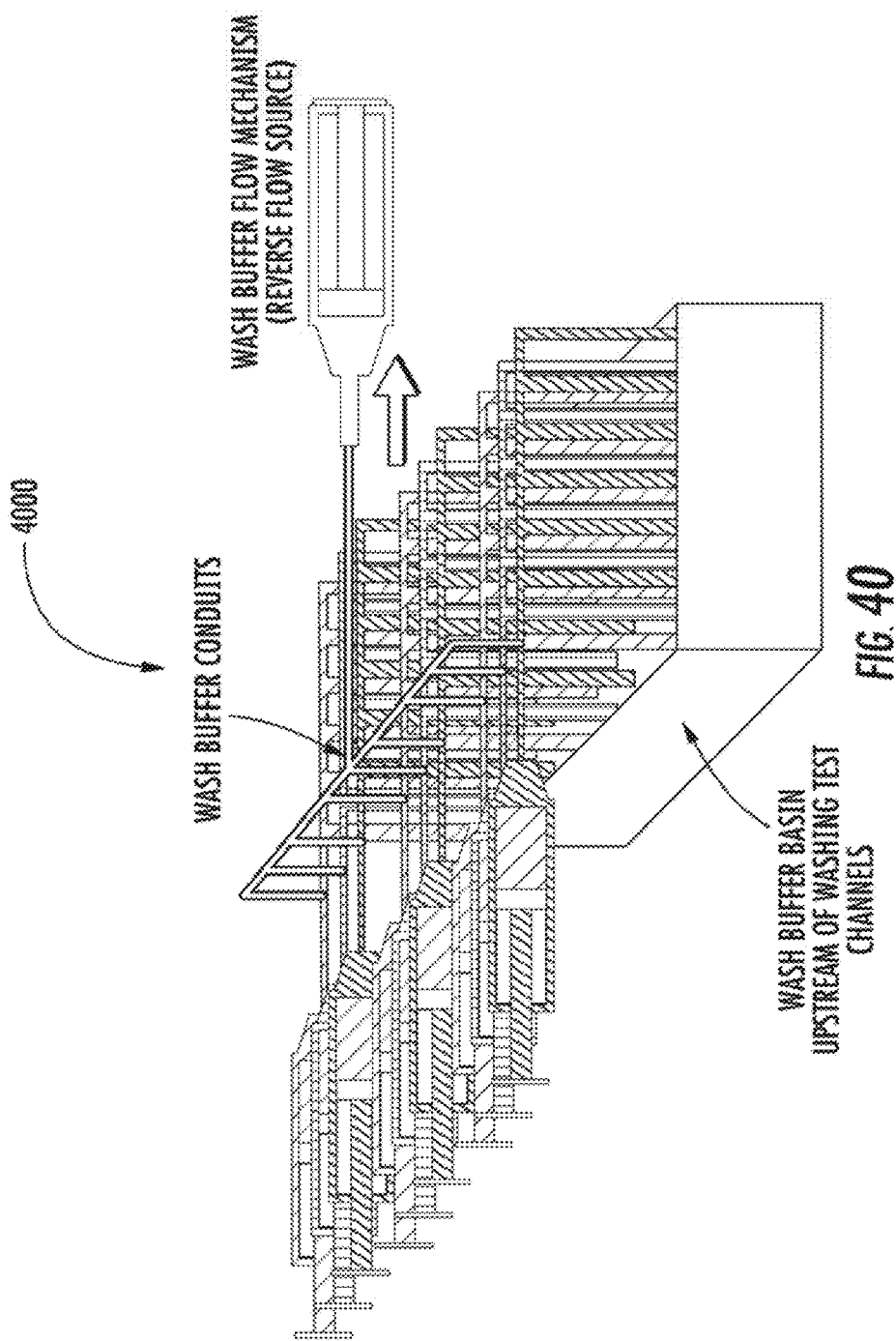

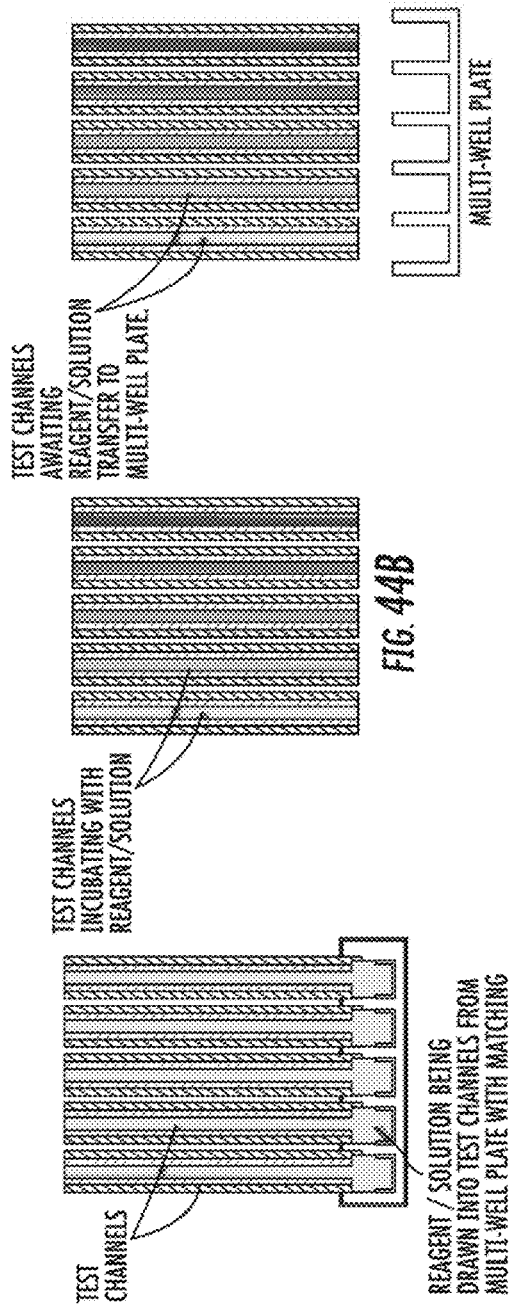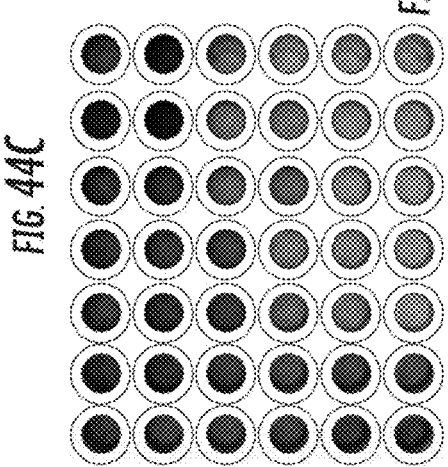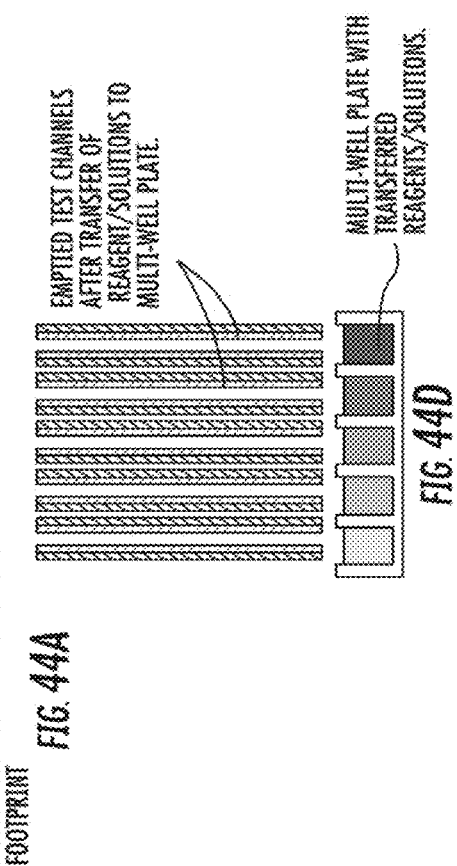

MULTI-PARAMETER THROMBOTIC ASSAY APPARATUS, SYSTEMS, AND METHODS

CROSS-REFERENCE TO RELATED APPLICATIONS

This application is a continuation of International Application No. PCT/US2012/063613, filed Nov. 5, 2012, which claims priority benefit of U.S. Provisional Patent Application No. 61/555,691 filed Nov. 4, 2011. These applications are incorporated herein by reference.

FIELD

The present disclosure relates generally to apparatus, systems, and methods for performing assays, and more particularly to apparatus, systems, and methods for performing multi-parameter thrombotic assays to generate thrombotic profiles for characterizing patients' thrombotic states and/or risks associated therewith.

BACKGROUND

Thrombosis, or blood clotting, can be the pathophysiological basis for a number of undesirable vascular complications. However, the ability to manage a patient's propensity to clot or bleed is currently limited. Efforts have been made toward the development of drugs that modify an individual's thrombotic state. Administration of antithrombotic therapy helps restore blood flow following vascular occlusion. Pro-hemostatic therapy, on the other hand, helps control provoked or spontaneous bleeding. However, some antithrombotic therapies can precipitate bleeding and some hemostatic therapies can result in excessive clotting.

Moreover, the methods used to treat thrombotic conditions have become increasingly complex as newer therapies are developed and combined into disease-specific therapies, increasing the difficulties of assessing patients' conditions. For example, when treating a patient with myocardial infarction, as many as five or six agents targeting different molecular pathways of thrombosis are typically administered, such as aspirin, clopidogrel, and integrillin, which are anti-platelet drugs, and heparin, lovenox, and bivalirtudin, which are anti-coagulant drugs. Chronically, patients may be treated with aspirin, plavix, and/or warfarin, or other oral coagulation inhibitors. The dosing, the timing of administration, and the manner in which novel therapies are to be incorporated (e.g., administering higher doses of clopidogrel or switching to Prasugrel, either of which can increase bleeding risk if applied too broadly) is a matter of debate. In fact, an increasing number of patients are being recruited into expensive clinical trials in an attempt to resolve these questions of proper therapies before the solutions are outdated. Notwithstanding, over 12 million people die each year from heart attacks, which remains the leading, and a still growing, cause of death worldwide.

A similar set of concerns are present in a number of other highly prevalent diseases, such as ischemic stroke, pulmonary embolism, deep vein thrombosis, atrial fibrillation, and dilated heart failure, as well as iatrogenically induced conditions, such as those that follow endovascular device therapy (e.g., placing stents, artificial valves, ventricular assist devices). The treatment of these cardiovascular diseases is made more complex when a patient simultaneously has a known bleeding condition, such as intracranial or gastrointestinal bleed. Clinicians, however, are continually faced with choosing an appropriate management strategy for such cases on a daily basis. Achieving an optimal balance between clotting and bleeding risk is cornerstone in the treatment of many vascular diseases and in the optimization of surgical risk. Notwithstanding these continued efforts, many therapies chosen can be sufficient for some individuals, but sub-therapeutic or supra-therapeutic for others. In other words, clot formation and bleeding risk is highly individual and influenced by a host of environmental and genetic factors which modulate an integrated risk.

The individualized character of thrombotic/bleed risk has led to extensive efforts to understand individual risk and, thus, personalize medical therapy. A variety of assays attempt to gauge a patient's propensity to clot or bleed, yet none offer an accurate, universal method of clinical risk assessment. Genetic testing is limited by the enormous impact environment has on thromboses. In addition, co-existing illnesses, medical therapies, and even trauma itself, greatly affect an individual's propensity to clot. Functional tests that directly measure the clotting process offer a way to integrate genetic and environmental influences. However, current clinical techniques only consider isolated aspects of the complex thrombotic process under contrived exposure conditions. Moreover, while large clinical trials target populations, performing analysis on smaller populations or subsets allows certain risk factors to be identified more specifically. Clinical risk scores have been developed that classify risk based on the number of independent risk predictors a patient may have. However, this methodology works for small populations or subpopulations better than at the individual patient level.

Accordingly, while forming clinical risk scores and/or collecting genetic data allows arriving at a more refined assessment of risk, these approaches can be limited. As one example, by following only the initial risk assessment and selection of therapy, these methods do not allow continued monitoring of any altered risk, such as may occur based on the chosen therapy. In other words, the above-described strategies are essentially "open loop," and are not designed to monitor and/or adjust to changing conditions after the initial therapeutic recommendation is chosen.

A variety of presently practiced functional assays attempt to assess not only a patient's baseline state, but also the patient's changing state in response to therapy, offering the potential for "closed-loop" control. Examples of such techniques include standard blood assays, such as whole blood or light transmission platelet aggregation studies. More complex assays can incorporate blood inducers of aggregation in addition to a reactive surface onto coated surfaces (e.g., fibrinogen-coated beads) to assess platelet function. Still other assays can expose blood to reagents, a surface, and blood flow conditions simultaneously to detect clot formation. Each of the aforementioned tools attempt to find a better predictive assay for an individual's thrombotic risk and response to therapy, and have been applied towards the evaluation of drug resistance patterns.

One observation resulting from these studies is the tremendous variability in the predictions. For instance, the prevalence of aspirin resistance varies between 4% and 60% depending on the assay used. Similarly, clopidogrel resistance can vary between 5% and 30%. Moreover, while these assays may target a specific drug, they do not account for the complex multi-drug environments that are used in real-world clinical practice, nor do they account for the constant flux in practice as new drugs are developed and others phased out. Moreover, these assay tests only consider an isolated aspect of thrombosis, such as platelet response. In reality, however, blood clots result from a complex interplay between platelet activation, aggregation, and adhesion, along with coagulation activation, all of which function in a powerful feed-forward loop. While other testing techniques, such as determining prothrombin time or activated partial thromboplastin time, may detect aspects of coagulation function, these techniques also fail to consider the important, interactive mechanisms that cause clinical blood clotting. Therefore, these isolated assays of specific aspects of clot formation fall short in their effectiveness and clinical utility. Presently, there is no standardized approach to assaying individual drug resistance patterns, nor for determining individual thrombotic risk as a whole.

Accordingly, there exists a need for improved techniques for performing thrombotic assays, and more particularly, for performing multi-parameter thrombotic assays to generate a thrombotic profile and characterizing patients' thrombotic state and/or risks associated therewith.

SUMMARY

In one aspect, an apparatus is provided for use in assessing clot activity in a specimen of blood under various conditions in vitro. In an embodiment, the apparatus includes a plurality of test receptacles adapted to receive a sample of blood, one or more flow generating mechanisms in fluid communication with the plurality of test receptacles, and a clot detector configured to analyze an amount of clot formation, if any, that occurs within the sample of blood in each of the test receptacles. Blood contacting surfaces of a first subset of the plurality of test receptacles are coated with a first surface substrate and blood contacting surfaces of a second subset of the plurality of test receptacles are coated with a second surface substrate which is different from the first surface substrate. The one or more flow generating mechanisms is configured to generate a first blood flow rate through a third subset of the plurality of test receptacles and to generate a second blood flow rate which is different from the first blood flow rate through a fourth subset of the plurality of test receptacles.

In another aspect, a method is provided for exposing blood to multiple conditions to determine clot activity. In an embodiment, the method includes exposing a specimen of blood to one or more blood conditions in vitro to form one or more blood samples, delivering the one or more blood samples into or through a plurality of test receptacles, and analyzing an amount of clot formation, if any, that occurs within each of the test receptacles. The one or more blood samples are delivered at a first blood flow rate through a first subset of the plurality of test receptacles and at a second blood flow rate which is different from the first blood flow rate through a second subset of the plurality of test receptacles. A third subset of the plurality of test receptacles have blood contacting surfaces which are coated with a first surface substrate, and a fourth subset of the plurality of test receptacles have blood contacting surfaces which are coated with a second surface substrate which is different from the first surface substrate.

In yet another aspect, a system is provided for determining one or more thrombotic conditions of a patient. In an embodiment, the system includes at least one memory that stores computer-executable instructions, and at least one processor configured to access the at least one memory. The at least one processor is configured to (i) execute the computer-executable instructions to receive a plurality of patient data points from a device which exposes a sample of the patient's blood to multiple exposure conditions in vitro, each patient data point including an amount of clot formation and one or more exposure conditions; (ii) create a virtual multi-dimensional representation of the plurality of patient data points ; and (iii) determine, based at least in part on the virtual multi-dimensional representation, one or more thrombotic conditions of the patient. The exposure conditions include blood contacting surface substrate, chemical agent addition, and blood flow rate.

In still another aspect, a method is provided for determining one or more thrombotic conditions of a selected patient. In an embodiment, the method includes (i) receiving, by at least one processor configured to access at least one memory, a plurality of patient data points from a device which exposes a sample of the patient's blood to multiple exposure conditions in vitro, wherein each patient data point includes an amount of clot formation and one or more exposure conditions; (ii), creating, by the at least one processor, a virtual multi-dimensional representation of the plurality of patient data points; and (iii) determining, by the at least one processor, based at least in part on the virtual multi-dimensional representation of the plurality of patient data points, one or more thrombotic conditions of the patient.

BRIEF DESCRIPTION OF THE DRAWINGS

FIGS. 17A-17B are schematics, illustrating one embodiment of multiple flow generators using a lever actuating mechanism.

FIG. 19 is a schematic, illustrating one embodiment of an apparatus including test receptacles and flow generators.

FIGS. 23A-23D are schematics, illustrating an embodiment of a flow generator that includes a deformable container.

FIGS. 25A-25B are schematics, illustrating one embodiment of a deformable container.

FIGS. 26A-26B are schematics, illustrating another embodiment of a deformable container.

FIGS. 27A-27B are schematics, illustrating one embodiment of a flow generator that includes multiple deformable containers.

FIGS. 28A-28B are schematics, illustrating another embodiment of a flow generator that includes multiple deformable containers.

FIG. 29 is a schematic, illustrating one embodiment of an apparatus including a flow generator that includes multiple deformable containers in communication with test receptacles.

FIG. 40 is a schematic, illustrating another embodiment of an apparatus including a washing mechanism.

FIGS. 44A-44E are schematics and a photograph, illustrating one embodiment of a technique for analyzing clot formation within test receptacles.

DETAILED DESCRIPTION

Figure 1:
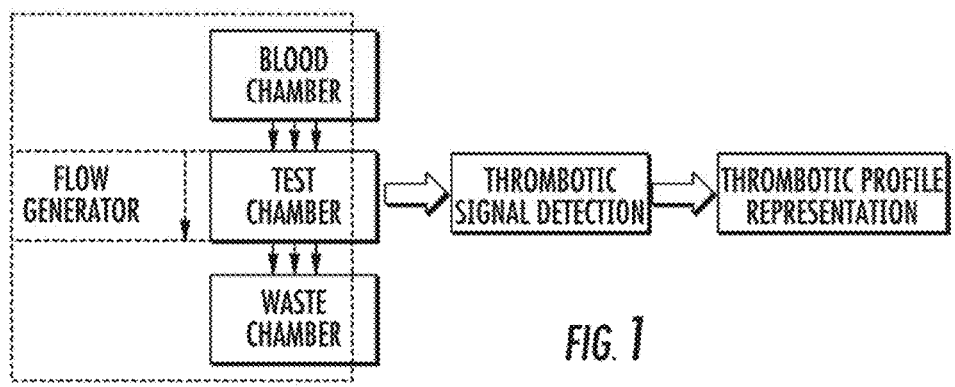
FIG. 1 is a block diagram, illustrating one embodiment of an assay system.

Improved apparatus, systems, and methods have been developed for performing thrombotic assays. According to various embodiments, these apparatus, systems, and methods are utilized to systematically expose blood to a number of different conditions in vitro and to observe the presence and/or the rate of blood clotting that occurs. These exposure conditions include different surface substrates, different blood flow rates, and different chemical agents (e.g., drugs). The apparatus, systems, and methods are useful in real-world clinical practice, as they advantageously enable consideration of the complex interplay between platelet activation, aggregation, and adhesion, along with coagulation activation, i.e. the interactive mechanisms that cause clinical blood clotting. Furthermore, the systems and methods provide a standardized approach to assaying individual drug resistance patterns and for determining individual thrombotic risk as a whole.

By altering the chemical makeup of the blood (also referred to herein as the "blood state"), the contact surfaces to which the blood is exposed, and the flow rates of blood through the testing receptacles, data sets of a vast number of thrombotic patient profiles can be systematically and reliably generated. Upon generation, the data sets can be correlated with specific information regarding the outcome and/or condition or state of the blood samples to generate predictive profiles for use in testing for a number of conditions and/or the development of thrombotic therapies (e.g., risk of clot, risk of bleed, suitability of anti-thrombotic agents, dosage of anti-thrombotic agents). Accordingly, the systems, apparatus, and methods described herein provide an improved solution to many of the above-discussed shortcomings for determining the thrombotic state of a patient, such as by considering a number of interdependent variables by a single test or related tests.

Thrombosis is a function of three interacting parameters: blood flow, blood state, and surface conditions. Therefore, assays that assess thrombosis of blood when exposed to varied flow, blood, and surface conditions allow relevant interactions to take place. In contrast to conventional assay techniques that expose a patient's blood to a limited set of contrived conditions and focus on isolated aspects of a patient's limited thrombotic response to those limited contrived conditions, the systems, apparatus, and methods described herein are provided to measure an individual's overall hemostatic or thrombotic state. Previous techniques fail to reproduce the physiology of in vivo hemostasis and thrombosis. Single or limited measurements lack the degrees of freedom to decode complex pro- and anti-thrombotic states. Given the high dependence of thrombosis on exposure conditions, including the patient's blood chemistry, the vessel wall conditions, and the flow conditions, high inter-assay variability can be expected. However, the multi-parameter assay embodiments described herein provide for the varying of test conditions in a purposeful fashion, allowing the interdependencies that characterize an individual's hemostatic state to be measured.

The multi-parameter assay techniques described herein combine conventional models in order to match relevant, real-world thrombotic states to better understand and predict clinical thrombotic events. For example, models are used to arrive at a number of flow conditions that represent those found in vivo. Similarly, the models permit replication of lesion sites by coating flow surfaces with reactive substrates. Additionally, various chemical agents or drugs can be introduced, as may occur during therapy or to represent a patient's physiological state. These models and varied conditions allowed assessment of the performance of a variety of assay devices and identification of the pro- and anti-thrombotic aspects of such devices, as well as identification of a meaningful set of blood state, blood flow, and substrate surface conditions to more fully represent and detect real-world thrombotic events.

A fundamental biological limitation exists in that the governing functions and quantitative relationships that relate the three parameters are typically unknown. Thus, while thrombosis may be a function of surface condition, blood flow, and blood state, the relationships governing their interactions are typically unknown. Analyzing the output of a single assay test hides the interactions and interdependencies. However, the systems, apparatus, and methods described herein illustrate how analyzing incremental parameter variation allows for the identification of parameter relationships and interdependencies. Therefore, by considering the output of multiple tests simultaneously, as described herein, one can understand not only the outcome of a given set of parameters, but the outcomes as a function of the parameter relationships, which are foundational to modeling principles. By purposefully varying the parameters over a wide, but relevant, range, the meaningful parameter space that captures an individual's thrombotic profile can be identified.

Accordingly, the systems, apparatus, and methods described herein provide for the generation of data underlying the identification of patients' thrombotic profiles based upon a vast number of the parameter relationships underlying thrombosis. Furthermore, understanding the parameter relationships and their impact on, and ability to predict, thrombosis, allows one to generate a useful set of thrombotic profile data and assay testing systems to be used as a point-of-care device to rapidly and accurately identify a patient's thrombotic state and/or other related condition or risk. For example, upon generating one or more thrombotic profiles through these foundational multi-parameter assay tests, reduced data sets can be utilized to analyze an individual patient's thrombotic state, such as to understand an individual's drug resistance patterns, to understand an individual's thrombotic risk, and/or to determine an optimal thrombotic state for a given disease or condition. Thus, by utilizing these systems, apparatus, and methods, complex, anti-thrombotic drug regimens can be monitored and means by which complex, anti-thrombotic drug therapies can be altered can be identified, such that an individual's thrombotic state can be identified and altered to the optimal or otherwise desired state for a given disease or condition.

The multi-parameter assay test systems, apparatus, and methods according to the present invention are described herein below with reference to the non-limiting embodiments illustrated in FIGS. 1-59.

Apparatus—Overview

In one embodiment, the apparatus for use in assessing clot activity in a specimen of blood under various conditions in vitro includes a plurality of test receptacles adapted to receive a sample of blood drawn from a patient, a plurality of flow generators in fluid communication with the plurality of test receptacles, and a clot detector configured to analyze an amount of clot formation, if any, that occurs within the sample of blood in each of the test receptacles. The plurality of flow generators may be induced or initiated with at least one flow generating mechanism. The apparatus may be utilized to expose blood to multiple conditions simultaneously or near-simultaneously, where the conditions include various blood contact surfaces, blood states, and blood flow rates designed to represent altered in vivo blood conditions. The exposed blood may be analyzed for amount of clot formation such that a thrombotic profile of the patient may be generated for use in treatment and risk assessment. Additionally, the apparatus may have the ability to separately detect the amount of thrombus or clotting formed as a result of each condition.

In one embodiment of the apparatus, the blood contacting surfaces of a first subset of the plurality of test receptacles are coated with a first surface substrate, and the blood contacting surfaces of a second subset of the plurality of test receptacles are coated with a second surface substrate which is different from the first surface substrate. For example, the first and second subsets may each include one or more test receptacles. In certain embodiments, additional subsets of test receptacles are coated with additional surface substrates. For example, the apparatus may include two, four, eight, or more different surface substrates.

In one embodiment of the apparatus, a first of the plurality of flow generators is configured to generate a first blood flow rate through a third subset of the plurality of test receptacles, and a second of the plurality of flow generators is configured to generate a second blood flow rate which is different from the first blood flow rate through a fourth subset of the plurality of test receptacles. For example, the third and fourth subsets may each include one or more test receptacles. The test receptacles of the third and/or fourth subsets may overlap with those of the first and/or second subsets. For example, a test receptacle may be in both the first and third subsets, such that the receptacle is coated with the first surface substrate and is exposed to blood at the first blood flow rate. In certain embodiments, additional subsets of test receptacles receive blood flowing at additional blood flow rates. For example, the apparatus may include two, four, eight, or more different blood flow rates.

In one embodiment of the apparatus, one or more blood chambers are provided in fluid communication with the plurality of test receptacles. The blood chambers are configured to introduce a chemical agent into the sample of blood therein. In other embodiments, at least one of the flow generators or at least one of the test receptacles is configured to introduce a chemical agent into the sample of blood therein. For example, the blood chambers may be configured to introduce a drug (e.g., aspirin) into the sample of blood therein.

For example, according to one embodiment, the assay apparatus includes multiple test receptacles that together form a test array through which an isolated portion of blood flows, whereby the blood condition, surface condition, and blood flow in each test receptacle can be varied. While exposed to the unique exposure conditions in the various test receptacles, clotting (e.g., normal hemostatic clot and/or abnormal thrombus) can occur. The level of clotting in each test receptacle is then measured to generate data sets that are utilized to represent the hemostatic state or thrombotic profile. The data sets can be analyzed and/or simplified, or more simply represented, utilizing any number of analytical and/or data mining techniques (e.g., best-fit functions, modeling, supervised learning, unsupervised learning, feature selection) to arrive at a reduced, more useful set of exposure conditions to generate specific thrombotic profile data relevant to a particular clinical state.

For example, testing and analyzing the multi-parameter thrombotic results of a cohort of patients (e.g., utilizing machine learning, such as supervised learning techniques) can enable one to determine certain thrombotic conditions and their associations with the measured thrombotic profile using the assay test systems. Other machine learning techniques, such as, but not limited to, feature selection processes, can be used to determine which of the multiple components of the measured thrombotic profiles provide predictive power of the thrombotic condition in question, thus allowing the number of exposure conditions to be reduced for more specific test applications. This reduced subset of test exposure conditions can be included in a smaller, convenient, and efficient assay test device for detecting one or more specific thrombotic conditions that are predictable by the selected exposure conditions, such as may be utilized in a clinical setting to provide effective patient therapy or identify thrombotic risks.

FIG. 1 is a block diagram representing an illustrative assay system overview, according to one embodiment. A multi-parameter thrombotic assay test system for generating thrombotic profiles, generally includes, but is not limited to: (a) one or more blood chambers in which the blood contained therein can optionally be exposed to different chemical reagents, concentrations of reagents, and/or combinations of reagents; (b) one or more test chambers (also referred to as "test receptacles" throughout the specification) with surfaces that have optionally been treated to represent one or more of the exposure conditions, coated with specific substances, concentrations of substances, and/or combinations of substances; and (c) one or more waste chambers into which the exposed blood is placed after exposure through the test chambers. In addition, the system includes one or more flow generators or flow inducing sources which causes the blood samples (and optionally, other reagents or washing solutions) to flow through the test receptacles.

According to one embodiment, each flow generator can be adapted to provide a different blood flow rate through the test receptacles, thus allowing for the control and variability of blood flow rates through the assay testing system. Though, in other embodiments, the flow generator or generators may themselves initially impart constant blood flow; however, the test chambers or other aspects of the assay test system are adapted to vary the flow of blood through the test chambers. The assay test systems also generally include means for detecting the extent of thrombus formation in each individual conduit of the test chamber, such as colorimetry or fluoroscopy devices described by example in more detail herein, and a means for representing the results from the individual conduits in a consolidated thrombotic profile that subsequently can be utilized to make clinical determinations and/or to generate subsets of exposure conditions and/or thrombotic profile data for identifying targeted thrombotic conditions.

The test receptacles may be configured as test conduits, test wells, or a combination thereof. According to various embodiments, the number of test conduits or test wells in each apparatus may vary. As a non-limiting example, the number of receptacles may range between 25 and 1000 conduits or wells, whereby some or all of those individual conduits or wells are exposed to different surface, blood, and/or flow conditions. However, any number of conduits or wells can be provided, which may depend upon the number of exposure conditions and/or the number of redundancies provided by the assay apparatus.

These test receptacles may generally be defined as either "open" test receptacles allowing blood flow though individual test conduits via an inlet and an outlet, or "closed" test receptacles into which blood is placed and flow is generated by agitation or inducing flow within test wells. In open test receptacles, the blood can move through the test conduits (and optionally into separate waste chambers) by the flow generator(s). In closed test receptacles, blood may move into the test wells and may be actively transferred (e.g., via pipette transfers) from the test wells into the waste chambers following blood exposure, rather than by continuous flow as may be possible with open test receptacles. The apparatus may include a combination of one or more open test conduits operating in parallel or series with one or more closed test wells.

For assay test systems having open test receptacles, blood flow may be generated using positive or negative pressure and/or positive or negative displacement flow devices. For example, blood flow may be generated by a pressure source, such as a positive pressure head or a vacuum source, that is provided across the test receptacles to drive the flow of blood. A positive pressure source would "push" blood through the test conduits, while a vacuum pressure source would draw or pull blood through the test conduits. Differential flow can be accomplished by any number of means, such as by providing a number of different pressure sources, each operable to provide different levels of positive or negative pressure, and/or by varying the resistance in a particular section of the assay test system (e.g., the test receptacle and/or separate resistance inducing chambers upstream and/or downstream of the respective test receptacles), such that the flow rate in any given conduit differs dependent upon the resistance (e.g., cross-sectional geometry). Capillary force and/or gravity may also be harnessed by the apparatus to drive or augment fluid flow through the system. The characteristics of the resistance sections can vary in aspects such as diameter and or length in order to vary resistance.

In other embodiments, blood flow is driven by positive or negative displacement flow generators, such as, but not limited to, pumps, syringes, syringe pumps, deformable chambers, compressible bags, or any other displaceable volumes, and a corresponding means for displacing the volume, such as, but not limited to, linear actuators, pistons, hydraulic systems, and the like. Embodiments using positive displacement create forward flow, "pushing" blood flow through the test conduits, while embodiments using negative displacements create reverse flow, "pulling" blood flow through the test conduits. In cases utilizing forward flow, the blood chambers (i.e., the chamber in which blood is exposed to a chemical agent) may be incorporated with, or be the same as, the flow generator, such as if the flow generator includes a chamber or piston to contain blood prior to expulsion.

According to one embodiment, varied blood flow is generated by incorporating multiple flow generators, each creating distinct blood flow rates, thus exposing the different sets of conduits to the different flow rates. For example, if one flow generator pumps at 1 ml/min and another pump pumps at 10 ml/min, and each flow generator is connected to 10 otherwise identical conduits, then each conduit connected to the 1 ml/min flow generator will experience an approximately 100 µl/min flow rate and each conduit connected to the 10 ml/min flow generator will experience an approximately 1 ml/min flow rate. Alternatively, by altering the number of conduits that are exposed to a given flow rate, the flow rate in any one conduit may be altered. For instance, if two flow generators (e.g., syringe pumps, deformable chambers) are pumping at or near the same rate, and one pumps through twenty conduits while the other pumps through 10 conduits, the 20 conduits, if otherwise identical, will have ½ the flow rate compared to the 10 conduits.

In yet other embodiments, the conduit cross-sectional geometries may be altered (e.g., within the test chamber or at any other point upstream or downstream of the test chambers) to cause a different flow rate. For example, each of the third set of the plurality of test receptacles may have a first diameter, while each of the fourth subset of the plurality of test receptacles has a second diameter different than the first diameter, and the first and second blood flow rates are dependent upon the first and second diameters, respectively.

Moreover, in some embodiments, varying flow rates may a result of a different flow generator driving mechanism or actuator, such as, but not limited to, a faster moving piston or screw, or a linear actuating mechanism that displaces syringes at different rates. In other embodiments, blood flow rates are altered by providing different displacement volumes displaced at or near the same rates, such as by varying the cross section of the flow pump chamber that is perpendicular to the direction of displacement (e.g., a syringe diameter). For example, 10 different flow rates can be provided by 10 different diameter syringe flow generators when the plungers are displaced at or near the same given linear rate. In one embodiment, the flow generators are syringe pumps and the blood flow rates are dependent upon the volumes of the pistons and/or the rates of actuation of the syringe pumps. In another embodiment, the flow generators are deformable chambers and the blood flow rates are dependent upon the volumes and/or the rates of compression of the deformable chambers.

As described, in some embodiments, blood chambers are provided for exposing the contained blood to a chemical agent. Illustrative chemical agents or reagents may be activators and inhibitors of thrombosis, platelet function, coagulation, fibrinolytic system, and/or endothelium, in addition to drugs, antibodies, and/or other small molecules, such as, but not limited to, adenosine diphosphate ("ADP"), epinephrine, thrombin, collagen, ristocetin, anti-platelet drugs, aspirin, $P1Y_{12}$ inhibitors (e.g., cangrelor), IIB/IIIa inhibitors (e.g., Eptifibatide), von Willebrand factor inhibitors, ARC1779, PAR-receptor inhibitors, cephalexin, PPACK, corn trypsin inhibitor, heparin, bivalirudin, argatroban, hirudin, activating snake venom, other anticoagulants, tissue plasminogen activator ("tPA"), urokinase, streptokinase, tenecteplase ("TNK"), and/or any combination thereof.

In various embodiments, between approximately 5 and approximately 50 different blood chambers are provided, or a smaller number of blood chambers that allow exposing the blood to approximately 5 and approximately 50 different chemical agents or combinations of agents. These chambers may be disposable chambers, for example the test tubes or vaccutainers from which blood is drawn, in fluid communication with the test receptacles via connecting pathways. In other embodiments, the blood chambers may be incorporated with or the same as the flow generator devices, such as when utilizing syringes or deformable bags or chambers to provide blood flow. According to various embodiments, the blood chambers will initially contain the reagents to which a particular batch of blood is to be exposed; though, in other embodiments, reagents may be supplied to the blood chambers after receiving the blood. In some embodiments, blood chambers include valves such that blood can be loaded into the chamber through an inlet, after which an outlet valve is opened to expel the blood therefrom. In some instances, conduits connect multiple blood chambers to allow filling from a single inlet port.

Figure 2:
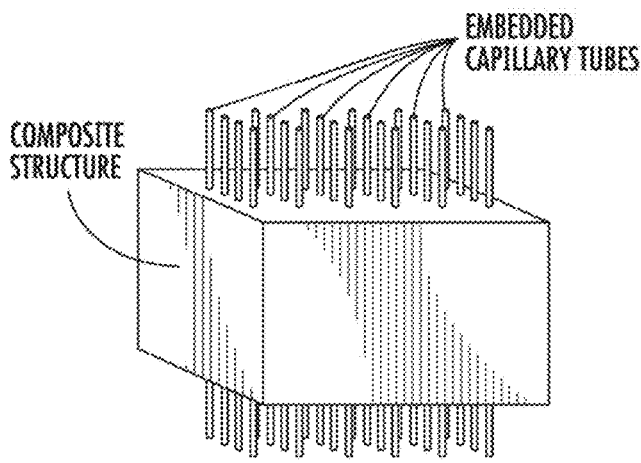
FIG. 2 is a perspective view, illustrating one embodiment of a plurality of test receptacles.
Figure 3:
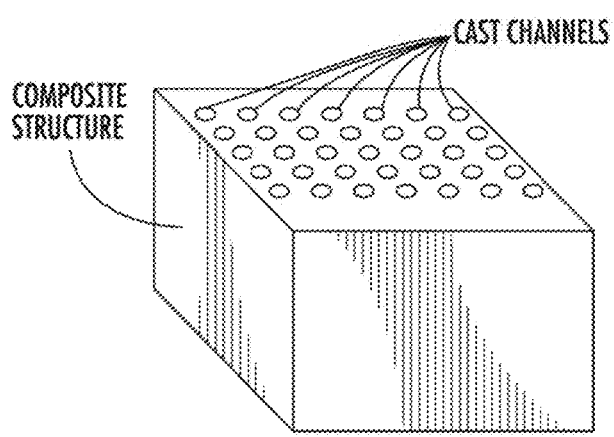
FIG. 3 is a perspective view, illustrating another embodiment of a plurality of test receptacles.

FIGS. 2 and 3 represent different embodiments of apparatus and associated conduits. FIG. 2 represents an apparatus wherein the conduits are formed as capillary tubes that are optionally embedded in a composite structure such as a silicone or plastic. FIG. 3 represents an apparatus having conduits cast directly into a composite structure, such as, but not limited to, silicone, plastic, glass, or metal. For example, casting may be accomplished using rods having an outer geometry that represents the desired inner shape profile of the conduits. The rods are cast into the moldable material and, after curing, the rods are removed leaving the individual conduits formed in the moldable/castable material. Alternatively the conduits may be extruded, such that the desirable conduits remain within the structure.

According to various embodiments, the conduits may have any cross-sectional geometry, such as, but not limited to, circular, square, rectangular, hexagonal, any other polygonal, or any other symmetric or asymmetric shape. In one embodiment, an inner cross-sectional diameter may vary between approximately 0.1 mm and approximately 1 mm, which allows multiple shear rates (some of which may be as high as up to 5000 liters/s) to be represented using a clinically practical quantity of blood, assuming that a test run lasts between approximately 30 seconds and less than approximately 10 minutes. In one embodiment, each individual test chamber conduit has a length between approximately 0.5 cm and approximately 20 cm. The conduits (or wells), and/or any other component of the assay test systems described herein, may be made from glass, plastic, metal, and/or any combination thereof, and are held together, such as shown in FIGS. 2 and 3.

As described above, the blood contacting surface of the conduits (or test wells) are coated with different substances, different concentrations of substances, and combinations of different substances to create the desired representative substrate exposure conditions. These substances, or substrates, may include thrombotic reactive species and adhesion molecules, such as, but not limited to, collagen, fibrinogen, fibronectin, thromboplastin, von Willebrand factor, cryoprecipitate, tissue factor, or other proteins. Conduits may alternatively, or additionally, be coated with endothelial cells that have been exposed to different conditions. Moreover, according to some embodiments, the conduits or test wells can be blocked with albumin to prevent non-specific surface interactions from occurring within the conduits or wells.

Apparatus—Flow Generators

Figure 4:
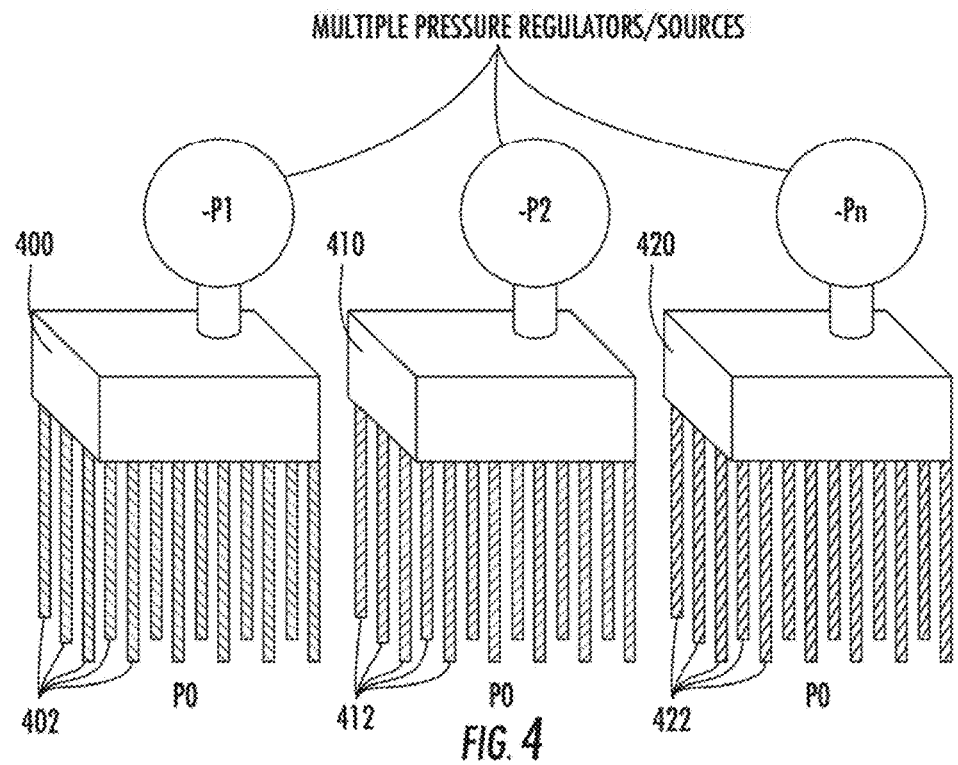
FIG. 4 is a schematic, illustrating one embodiment of an assay test system utilizing pressure sources to generate flow.

FIG. 4 illustrates an assay test apparatus embodiment representing conduits in communication with multiple flow generator devices provided as pressure sources (e.g., multiple vacuum sources) generating varying levels of pressure. By providing different levels of pressure (e.g., vacuum), the blood flow rate through a given conduit or set of conduits can be varied. In an example in which the pressure source is a vacuum pressure source, the pressure gradient is measured with respect to a reference pressure P0, such as at atmospheric pressure. In other embodiments, the pressure sources may be positive pressure sources and in communication with the test conduits at a location upstream to allow pushing or forcing the blood therethrough. Moreover, although three pressure sources are provided, any number of pressure sources can be provided.

Figure 5:
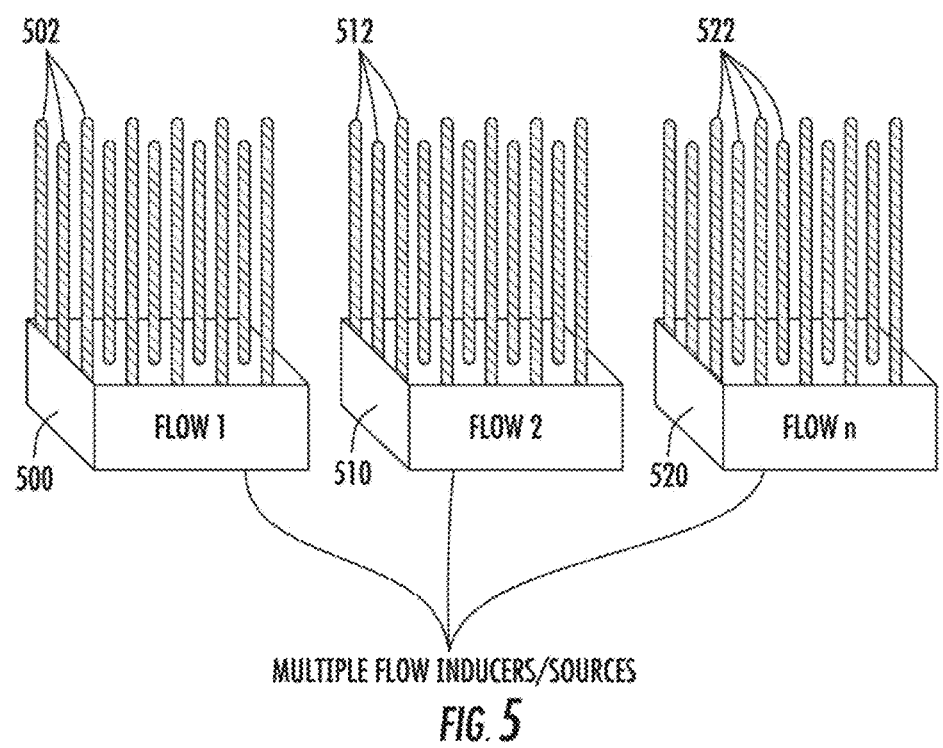
FIG. 5 is a schematic, illustrating one embodiment of an assay test system utilizing a flow source to generate flow.

FIG. 5 illustrates an assay test apparatus embodiment representing test conduits in communication with multiple flow generator devices that are provided as volume displacement devices. The test conduits are subject to different blood flow and, thus, different blood shear rates, by flow generators creating different displacement flows. As previously described, the volume displacement flow generator devices may be any suitable displacement devices, such as, but not limited to, pumps, syringes, syringe pumps, compressible bags, or any other displaceable volumes, and a corresponding means for displacing the volume, such as, but not limited to, linear actuators, pistons, hydraulic systems, and the like.

Figure 6:
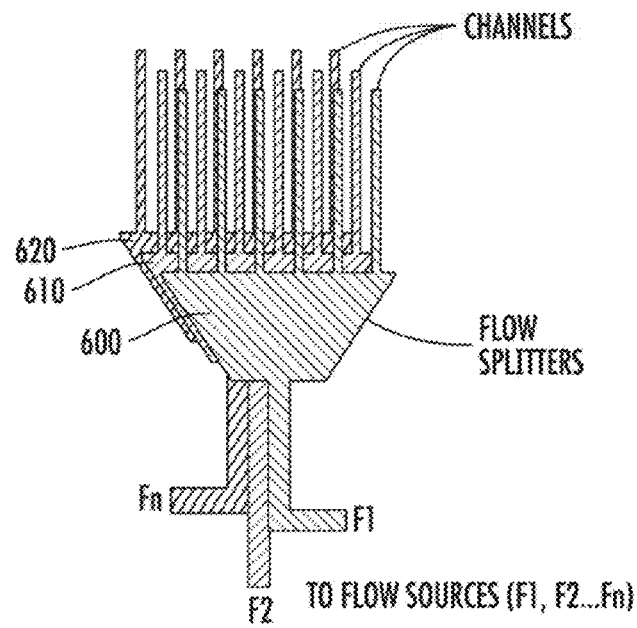
FIG. 6 is a schematic, illustrating one embodiment of an assay test system having multiple sets of test receptacles, with each set in communication with a different flow generator.

FIG. 6 illustrates one embodiment of an assay test apparatus having three subsets of test conduits (i.e., "channels"), with each test chamber in communication with a different flow generator operable to generate a different blood flow rate. According to this embodiment, each subset includes a flow splitter 600, 610, 620 that divides the blood flow through the multiple individual conduits within the subset. According to some embodiments, the flow generators can be displacement flow generators, which can either drive blood flow forward through the test receptacle or withdraw blood flow in retrograde fashion depending on the configuration of the displacement flow generator. In other embodiments, a flow splitter may operably be combined with a positive or negative pressure flow generator. Thus, the apparatus may include one or more flow splitters configured to direct blood flow from a single flow generator to a plurality of test receptacles.

Figure 7:
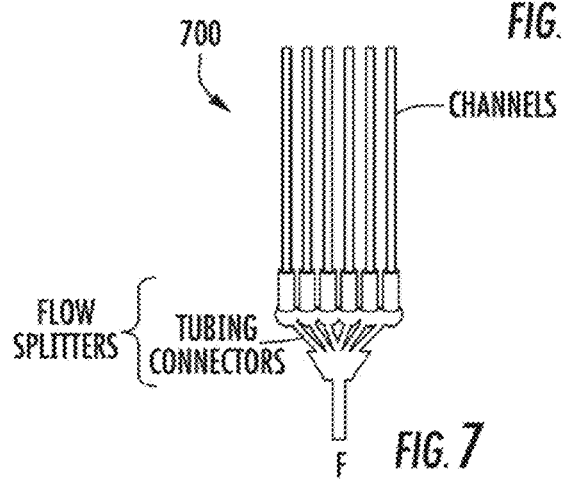
FIG. 7 is a schematic, illustrating one embodiment of a flow splitter.
Figure 8:
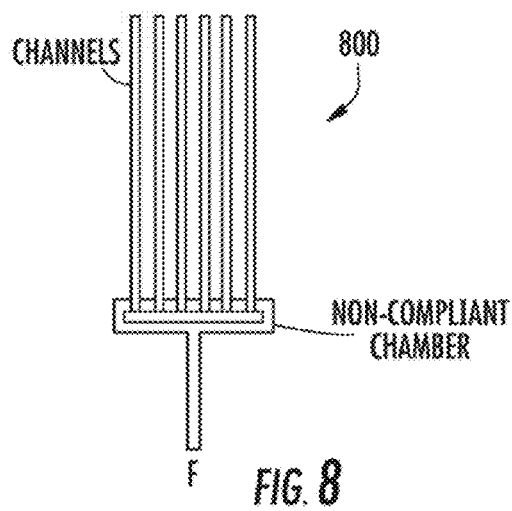
FIG. 8 is a schematic, illustrating another embodiment of a flow splitter.

FIGS. 7 and 8 illustrate schematic diagrams of illustrative flow splitters, according to various embodiments. With reference to the embodiment 700 illustrated by FIG. 7, a flow splitter includes individual tubing connectors each in fluid communication with corresponding conduits. The tubing connectors converge to a single connector in fluid communication with the corresponding flow generator. With reference to the embodiment 800 illustrated by FIG. 8, a flow splitter includes a common, non-compliant chamber or reservoir in fluid communication with each of the individual conduits. The flow generator provides blood flow into the common chamber. Upon filling the common chamber, blood exits equally through the conduits. In any of these embodiments, connections between the flow generator and the individual conduits can have a significantly larger diameter than the conduits to minimize their resistance to the flow of the blood. In yet other embodiments, the flow spitting mechanism may be a combination of the mechanisms shown in FIGS. 7 and 8, such that multiple tubing connectors connect to multiple flow splitting chambers that further divide the flow of the blood.

Figure 9:
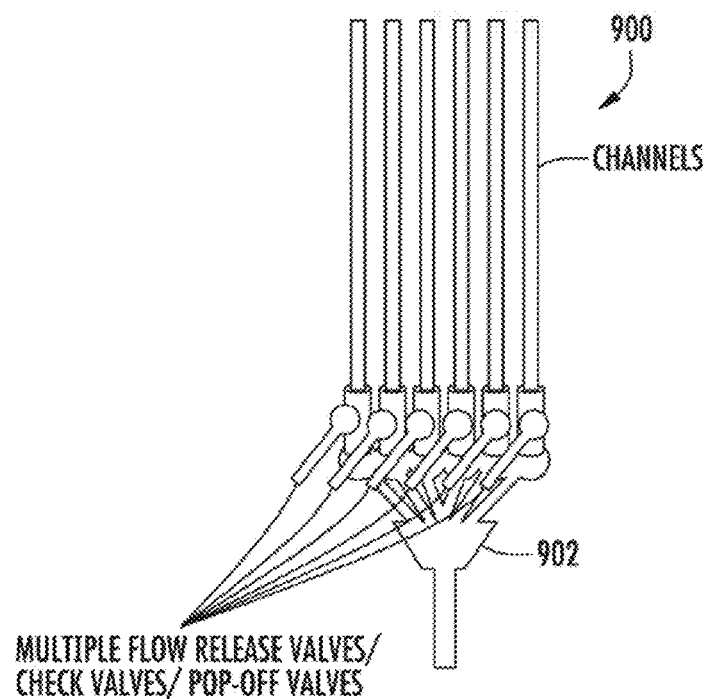
FIG. 9 is a schematic, illustrating one embodiment of a flow splitter having release valves.
Figure 10:
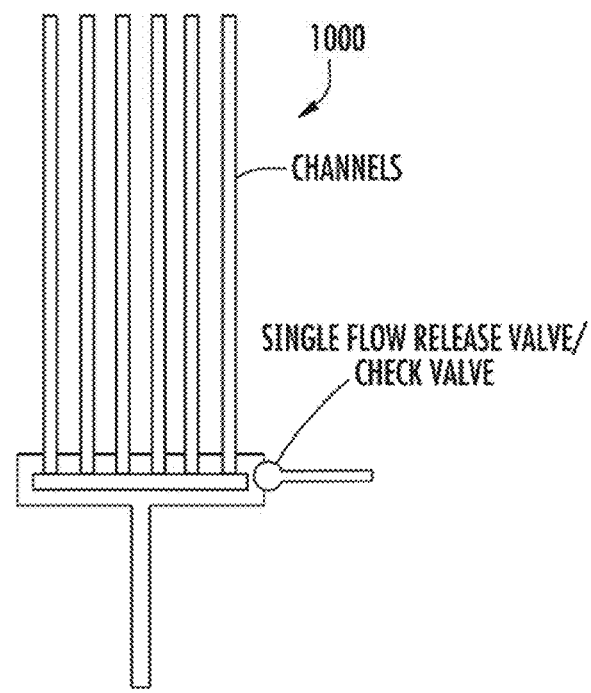
FIG. 10 is a schematic, illustrating another embodiment of a flow splitter having release valves.

FIGS. 9 and 10 illustrate flow splitters that include release valves, according to various embodiments. Release valves can serve as release, check, or pop-off valves to prevent pressure and/or flow build up and to maintain constant blood flow/resistance when particular conduits or groups of conduits become blocked, such as due to clotting. By diverting the blood flow upon occlusion of the conduits out a valve, the flow to the remaining conduits can be maintained at or near a steady rate. According to this embodiment, each valve may be monitored for the open or closed state as an indicator of whether or not the corresponding conduit has formed a clot. In some embodiments, the time to valve opening may be used as a measure to quantify individual test conduit thrombus formation. With reference to the embodiment 900 illustrated by FIG. 9, a flow splitter 902 includes multiple individual release valves with each individual flow splitter associated with each conduit. If a single conduit is blocked, the corresponding valve will divert blood flow. In one embodiment, each test conduit includes a valve configured to divert blood flow therefrom when the test conduit is occluded. With reference to the embodiment 1000 illustrated by FIG. 10, the flow splitter includes a single valve to prevent pressure build up if all conduits of the test chamber are blocked.

Figure 11:
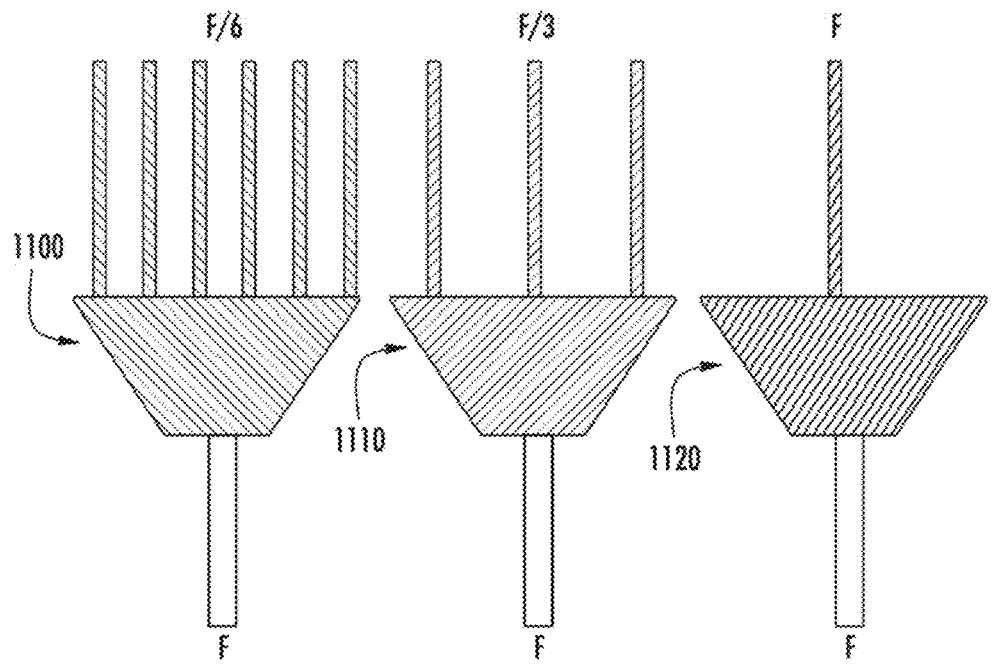
FIG. 11 is a schematic, illustrating various embodiments of flow splitters.
Figure 12:
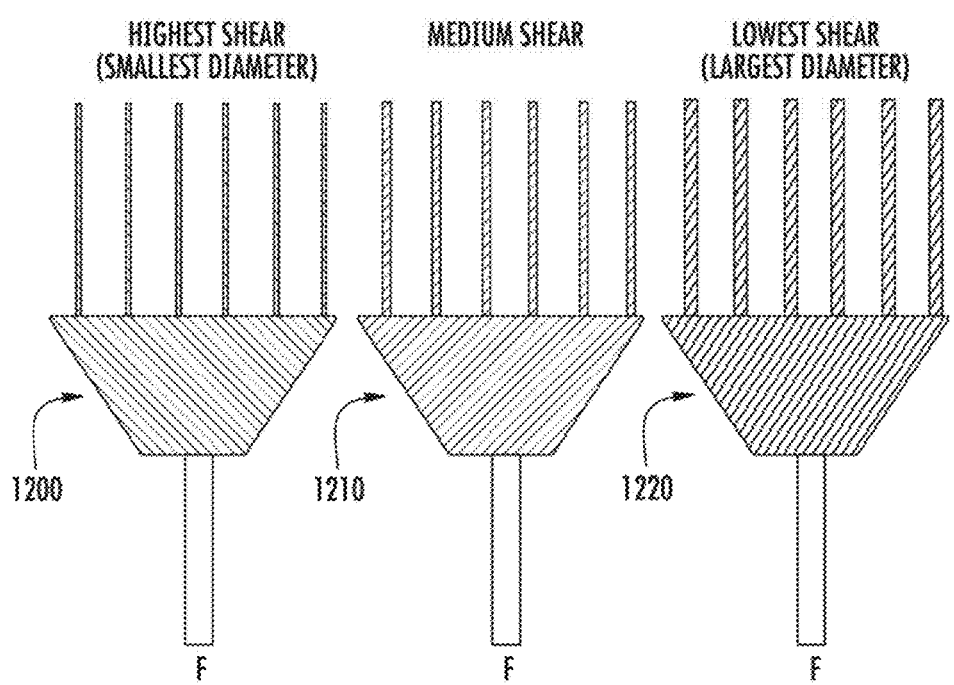
FIG. 12 is a schematic, illustrating further embodiments of flow splitters.

FIGS. 11 and 12 illustrate the flow principles associated with test conduits, according to various embodiments. With reference to FIG. 1, the test chambers 1100, 1110, 1120 include a different number of similarly dimensioned parallel conduits to alter the blood flow rates therein. Assuming that a constant blood flow is provided to each test chamber (e.g., via multiple individual devices providing constant flow rates), the greater the number of conduits associated with the flow generator device, the lower the flow rate will be. For example, as illustrated, the first test chamber on the left having six conduits will each experience a blood flow rate that is approximately one-sixth the blood flow rate through the single conduit in the test chamber on the right. Any number of conduits can be provided with the test chambers and/or flow generators, and the examples provided by FIG. 11 are for illustrative purposes only.

Similarly, FIG. 12 illustrates test chambers 1200, 1210, 1220 in which the number of conduits associated with each is approximately the same and the flow generator device is consistent, but that the cross-sectional diameters of the conduits in each of the test chambers differ (or differ within a single test chamber). The blood flow rate varies inversely with the cross-sectional diameter of a conduit. Thus, assuming constant flow by the flow generator device(s), larger conduits experience lower flow rates and lower shear rates.

Figure 13:
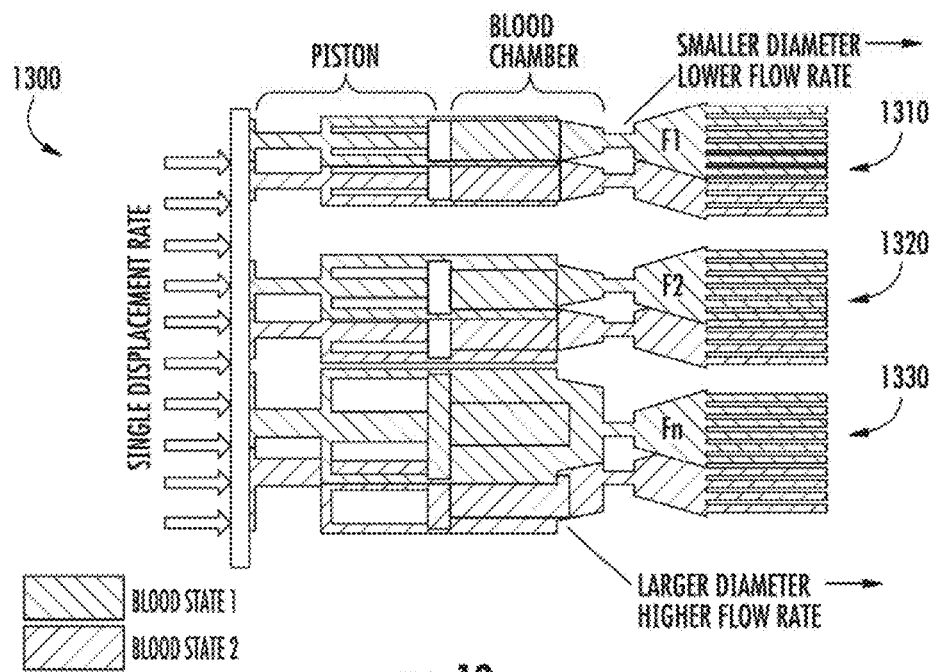
FIG. 13 is a schematic, illustrating one embodiment of an apparatus having multiple flow generators.

FIG. 13 illustrates one embodiment 1300 of flow generators and test chambers 1310, 1320, 1330 adapted to adjust blood flow rates based on the configuration of the flow generators. According to this embodiment, the flow generators are multiple syringe pumps having different cross-sectional diameters of the syringe piston. Accordingly, the greater the cross-sectional area, the greater the volume (assuming constant piston length) and the greater the blood flow rate if actuated at or near the same rate. Thus, according to one example, a single syringe pump actuator may be provided that actuates all of the syringe pumps at or near the same rate (e.g., within 1%, 2%, 5%, or 10% of the same rate). However, in other embodiments, multiple actuators may be provided that are adapted to actuate the respective syringe pumps at or near the same rate. In this example, multiple syringe pumps having the same cross-sectional diameter are shown to generate similar blood flow rates through different test chambers, such as may be desirable for testing differently treated blood. Although only two blood states or conditions are depicted in FIG. 13, any number of blood conditions may be provided.

Figure 14:
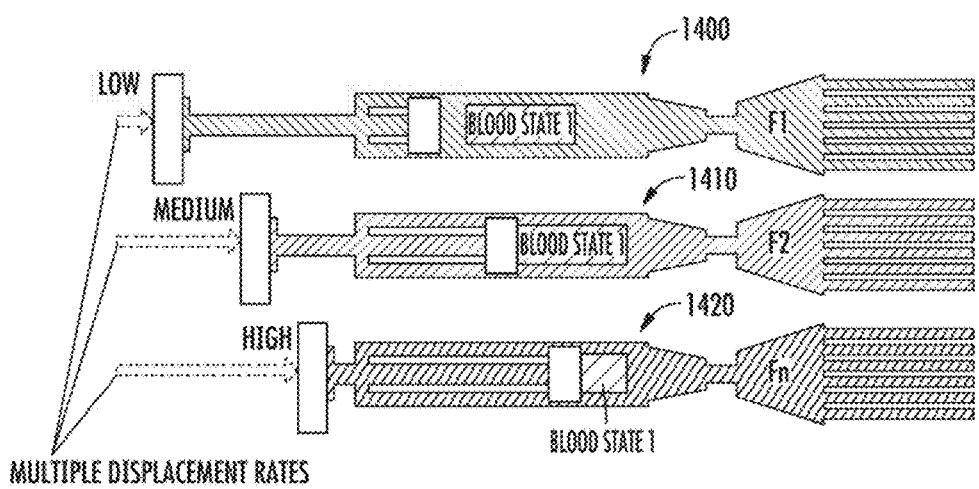
FIG. 14 is a schematic, illustrating another embodiment of an apparatus having multiple flow generators.

Conversely, FIG. 14 illustrates one embodiment of flow generators 1400, 1410, 1420 adapted to adjust blood flow rates based on the rate of actuation of the flow generators. According to this embodiment, the syringe pumps may have the same or similar cross-sectional diameter and piston volume, but may be actuated at different rates, thus resulting in different blood flow rates through the respective test chambers.

Figure 15:
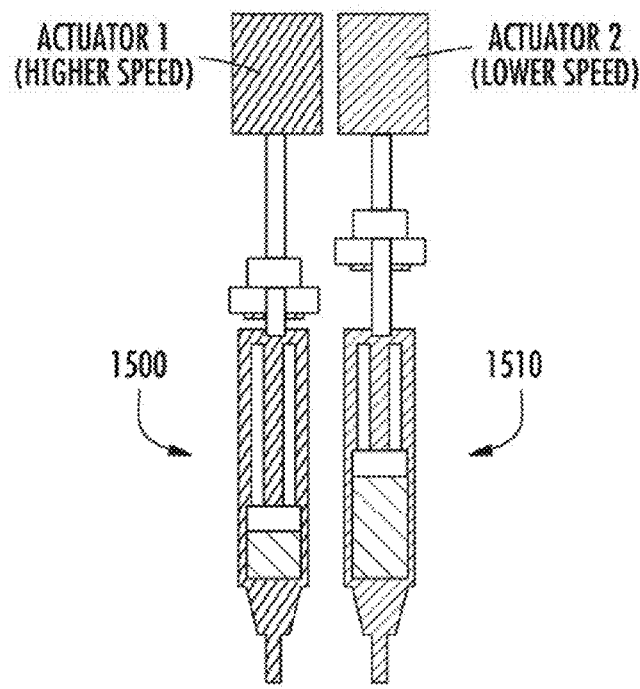
FIG. 15 is a schematic, illustrating one embodiment of flow generators configured for producing flow rates.
Figure 16:
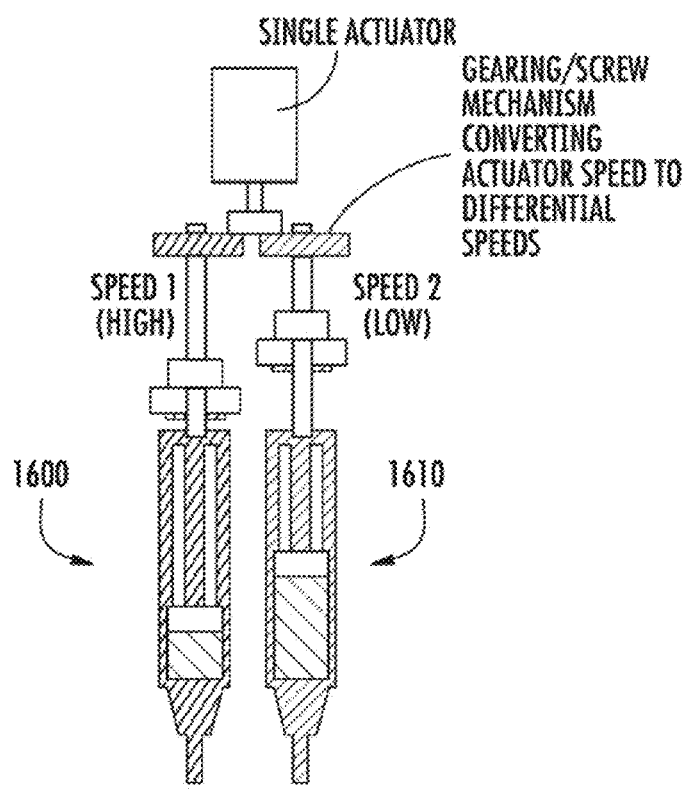
FIG. 16 is a schematic, illustrating another embodiment of flow generators configured for producing different flow rates.

FIGS. 15 and 16 illustrate means for altering the actuation rate of different flow generators, according to various embodiments. With reference to FIG. 15, different actuators operating at different rates in operable communication with the multiple syringe pumps 1500, 1510 (or other flow generator devices) are provided. For example, the actuators may be motor driven, whereby each motor is configured to operate at a different speed. In some embodiments, the motor speeds may be adjustable to allow easily altering the blood flow test conditions. With reference to FIG. 16, a single actuator is provided in mechanical communication with the multiple syringe pumps 1600, 1610 (or other flow generator devices). A conversion or differential mechanism is provided with to alter the actuation rate of different syringe pumps when driven by the same actuator. A conversion or differential may include, but is not limited to, conventional gearing, a worm drive, belt and pulley system, etc. Any number of conversion or differential mechanisms may be adapted to provide any number of actuation rates.

FIGS. 17A-17B illustrate one embodiment of a plurality of flow generators 1700 adapted to adjust blood flow rates based on the rate of actuation of the flow generators. According to this embodiment, a mechanical lever/pinion mechanism is provided with syringe pump flow generators to create differential syringe piston displacements. Each of the syringe pistons is filled with a different volume of blood, depending upon the expected blood flow rate therefrom. Thus, the farther the distance the syringe is from the fulcrum of the lever, the greater the volume of blood is contained in the piston, given that the lever will actuate the connected syringe piston at a greater rate, relative to those closer to the lever fulcrum. Accordingly, as the lever is pivoted about the fulcrum, the blood flow rates vary in direct relation to the distance from the fulcrum—the greater the distance from the fulcrum, the greater the blood flow rate through the respective syringe pump. According to various embodiments, any number of lever/pinion mechanisms may be provided. In addition, each syringe pump may be in communication with one or with multiple test conduits.

Figure 18:
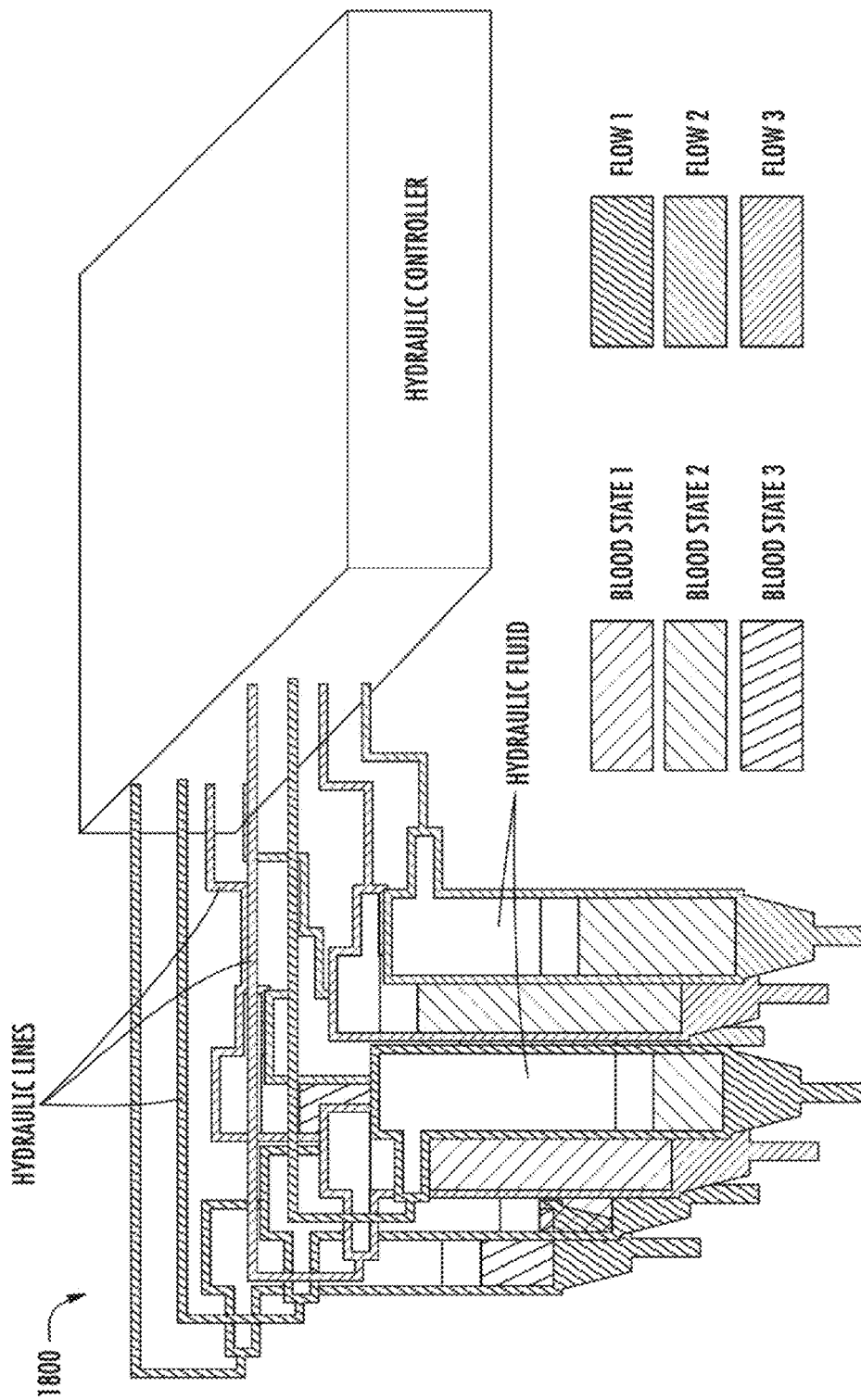
FIG. 18 is a schematic, illustrating one embodiment of multiple flow generators using a hydraulic actuating mechanism.

FIG. 18 illustrates one embodiment of a plurality of flow generators 1800 adapted to adjust blood flow rates utilizing a hydraulic controller or pneumatic controller. According to this embodiment, a hydraulic controller is provided in operable communication with each of the flow generators, which are shown as syringe pumps, but which may be any other flow generator device suitable for hydraulic or pneumatic operation (e.g., deformable bags, etc.). The hydraulic or pneumatic controller may control each flow generator device individually, or may control multiple flow generator devices together, such as if groups of flow generator devices are configured for delivering the same or similar blood flow rate.

FIG. 19 illustrates a schematic overview of an assay test apparatus showing an illustrative arrangement of test chambers 1525, conduits 1515, and flow generators 1535, and their respective arrangement, according to one embodiment. In this example, the flow generators are embodied as syringe pumps. Accordingly, the syringe pumps also serve as the initial blood chambers where the blood is exposed to varied reagents or other representative blood conditions. Each of the syringe pumps is associated with multiple conduits in a test chamber, such that each conduit in fluid communication with the same syringe pump will receive blood that is treated according to the same blood condition.

In this simplified example, four different blood states 1505a-1505d are represented, with each test chamber 1525 configured to deliver a single blood state 1505 through the associated conduits. Three different blood flows 1510a-1510c are provided, which each pump syringe 1535 that is associated with a single test chamber 1535 configured to deliver blood at a different flow rate 1510. Each of the six conduits 1515 associated with a single pump syringe 1535 may further represent different surface conditions (not labeled). For example, with reference to the upper right test chamber 1525, all of the blood delivered therethrough has the same blood state 1505c, which is different from each of the other test chambers. Three pump syringes 1535 are shown, each associated with and operable to deliver blood through six different conduits 1515, each of which represent different surface conditions. Each pump syringe 1535 is adapted to deliver blood at a different flow rate 1510a-1510c. In the illustrated example, each horizontal row of six conduits 1515 receives the same blood state 1505c delivered at a different flow rate 1510a-1510c, and each conduit 1515 in each row represents a different blood state. Accordingly, it is possible by this simplified arrangement to represent seventy-two different conditions. This arrangement, however, is provided for illustrative purposes only, and any number of blood states, blood flow rates, and/or surface conditions may be provided by altering one or more of the flow generator and/or conduit configuration and/or blood samples, as further discussed herein. Moreover, although a syringe pump flow generator device is illustrated in FIG. 19, any other flow generator described herein may be similarly supplied.

Figure 20A:
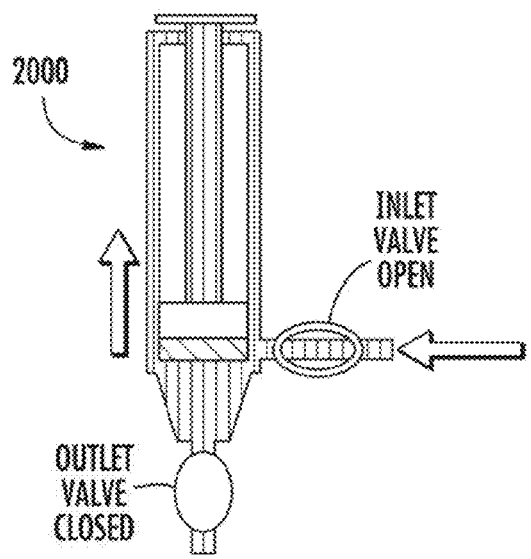
FIGS. 20A-20B are schematics, illustrating one embodiment of a flow generator device having an inlet valve and an outlet valve.
Figure 20B:
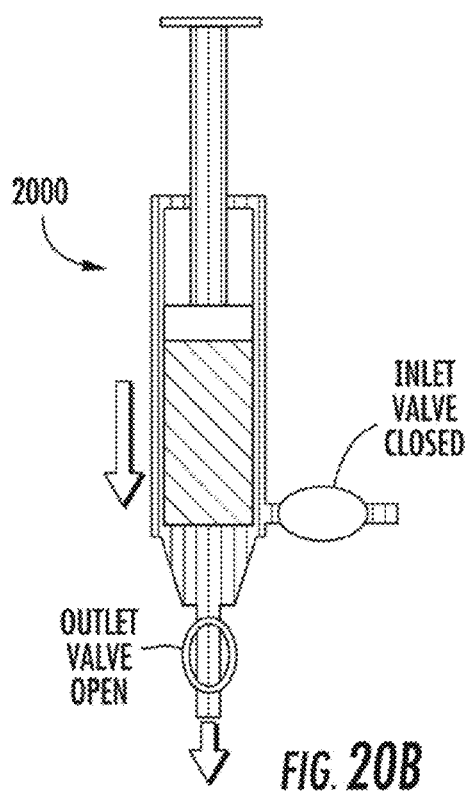

FIGS. 20A-20B illustrate schematic representations of valves provided with a flow generator 2000, according to one embodiment. In this embodiment, a flow generator, which is illustrated as a syringe pump, but can instead be any other flow generator device described herein (e.g., deformable bag, etc.), includes an inlet valve and an outlet valve, either of which may optionally be a one-way valve. Thus, the inlet valve may allow filling each syringe piston chamber (or other device chamber) with blood prior to delivery through the assay test system, as described above. While filling each syringe piston chamber, the outlet valve may remain closed, as depicted in FIG. 20A. When delivering blood through the test receptacles for testing, the inlet valve will be closed and the outlet valve opened as blood is forced therethrough, as depicted in FIG. 20B. Valves may be provided with any of the flow generator devices described herein as a means to selectively fill or otherwise provide a blood supply to the flow generator devices and/or to selectively restrict outflow of blood therefrom. Similar valve mechanisms can be provided to fill blood chambers that retain blood prior to delivery, such as when the flow generator device embodies a negative or positive pressure source, for example. Moreover, in some embodiments, multiple flow generators can be filled via a valve system from a single blood supply. In some embodiments, the valves are adapted to allow filling flow generator devices of different volumes (e.g., different sized deformable bags or piston chamber volumes). Moreover, in some embodiments, valve systems further allow for incorporating different reagents into different flow generator chambers prior to filling such that blood and reagent mixing occurs during filling.

Figure 21:
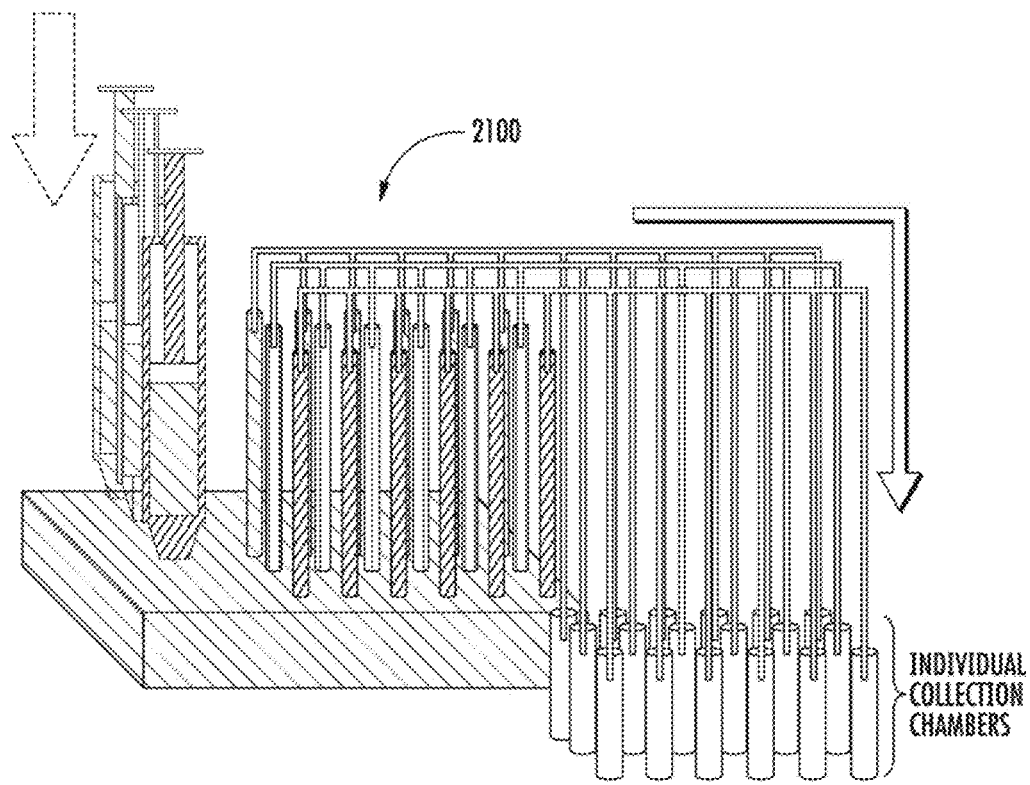
FIG. 21 is a schematic, illustrating one embodiment of an apparatus having multiple blood chambers, flow generators, and collection chambers.
Figure 22:
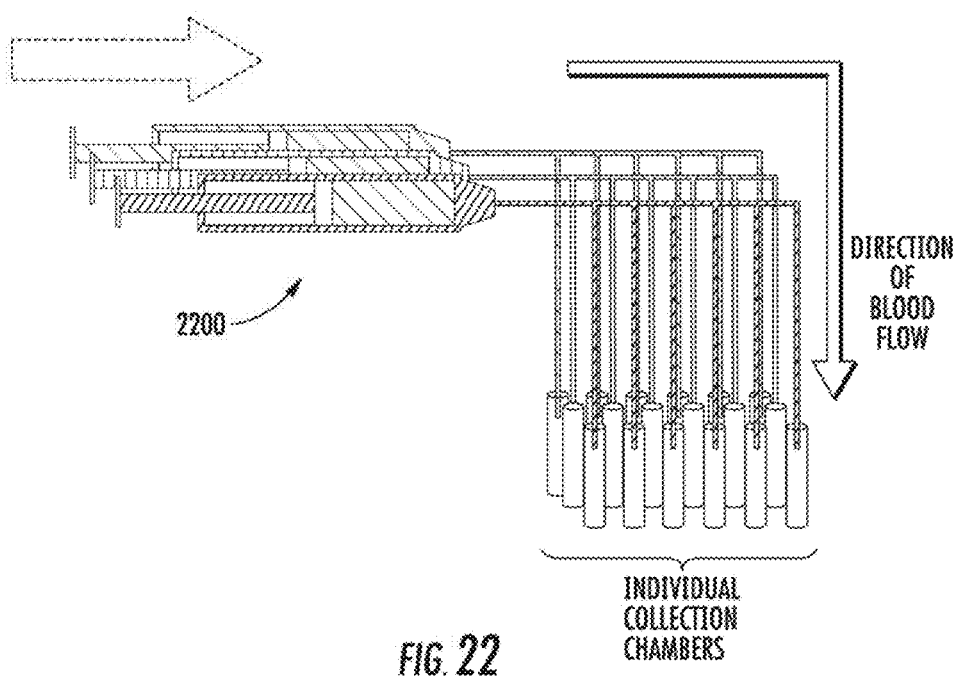
FIG. 22 is a schematic, illustrating another embodiment of an apparatus having multiple flow generators and collection chambers.
Figure 24A:
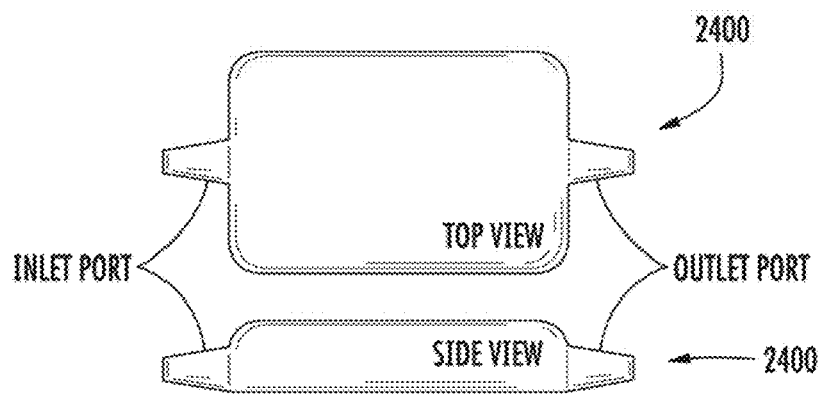
FIGS. 24A-24D are schematics, illustrating another embodiment of a flow generator that includes a deformable container.
Figure 24B:
Figure 24C:
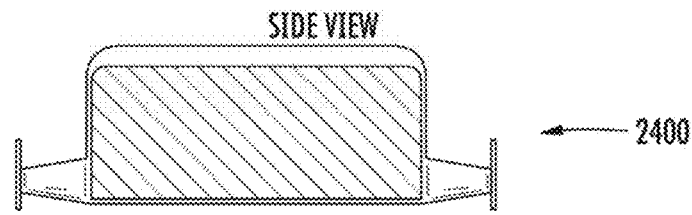
Figure 24D:
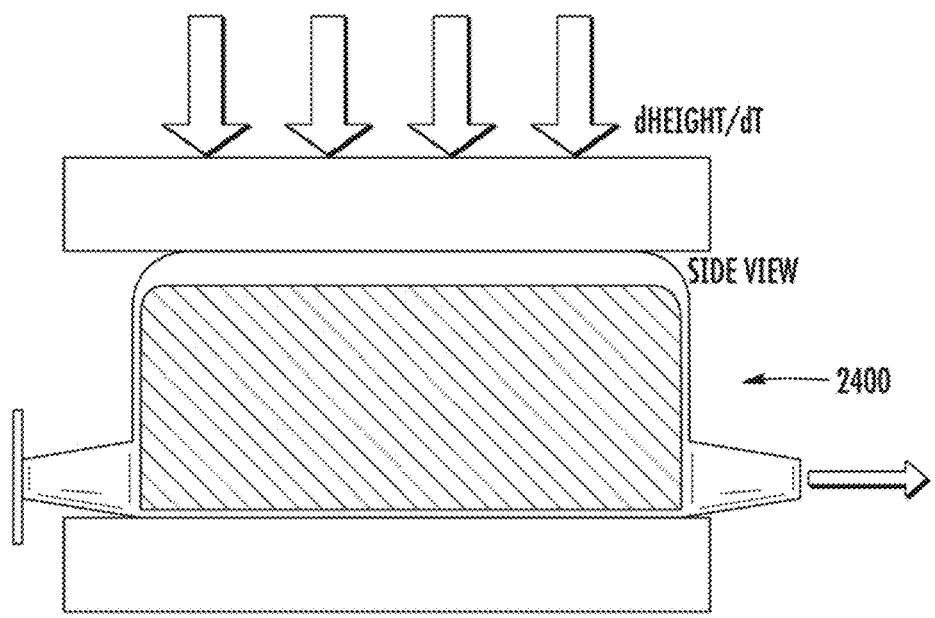

FIGS. 21 and 22 illustrate schematic overviews of assay test apparatus 2100, 2200 showing ways to deposit exposed blood in separate chambers, such as for subsequent assay analysis, according to various embodiments. After blood passes through the respective test conduits, the blood is further collected in individual collection chambers. With reference to FIG. 21, one or more flow generator devices (e.g., syringe pumps, deformable bags, etc.) deliver blood from the bottom and upward into the individual conduits for exposure to the surface conditions therein. After being exposed to the individual conduit surface conditions, the flow generators continue to pump the blood through pathways connecting each test conduit to a respective individual collection chamber. FIG. 22 illustrates a different configuration, whereby the blood is delivered down from the top through the individual test conduits utilizing one or more flow generator devices, and then directly from the bottom (or outflow if positioned horizontally, etc.) of the test conduits into corresponding individual collection chambers. Therefore, each of the individual collection chambers can be further analyzed to determine the clotting or other thrombotic state indicators present with respect to the specific conditions represented by the combination of the blood state, the blood flow rate, and the surface conditions of the respective test conduit. In other embodiments, the collection chambers and the test conduits may be integrated, such that the blood is retained in the test conduits for subsequent analysis and need not be transferred, which may be possible if the test conduits are configured as a "closed" system.

FIGS. 23-29 illustrate embodiments of flow generators that include one or more deformable chambers or other compressible containers, according to various embodiments. With reference to FIGS. 23A-23D, a flow generator device may generally be embodied as a pump chamber configured as a fillable, fixed volume compartment that is deformable or otherwise compressible. When filled with blood and subsequently compressed, a blood is ejected from an outlet port generated the desired blood flow. In one embodiment, the deformable chamber is highly compliant at low filling volumes and essentially non-compliant, or at least significantly less compliant relative to its state at low volumes, when at high filling volumes, such as when the volume is at or near the target volume. In the example of FIGS. 23A-23D, the deformable chamber has a single port which serves as both an inlet and outlet through which blood in injected and expelled. FIG. 23A illustrates a top view and side view of the deformable chamber empty. FIGS. 23B-23C illustrate side views of the chamber when filling and fully expanded, respectively. According to one embodiment, a deformable chamber may be formed such that as it is filled, the chamber only deforms in the direction of the displacement, such as increasing only in height. FIG. 23D illustrates a system by which the deformable chamber is compressed at a prescribed rate to generate blood flow through the outlet port. Also, according to one embodiment, the deformable chamber has a rectangular profile, the volume defined by the product of the chamber length times the width times the height. The flow rate according to this embodiment is calculated as the product of the chamber length times the width times the height divided by the change in time during which the height changes (assuming that height is the only changing dimension).

According to one embodiment, a deformable chamber can be filled with blood using one or more filling syringes (or other filling devices) in fluid communication with an inlet port. Similar to the syringe pumps described above, different deformable chambers can be utilized to hold different reagents for mixing with blood during filling.

FIGS. 24A-24D illustrate an embodiment of a deformable pump chamber having multiple ports, one of which is an inlet port for filling the chamber with blood and the other an outlet port for ejected blood to generate the desired blood flow through the assay test system. In some embodiments, the inlet and/or outlet ports may be open or closed, depending on the filling and emptying cycle. These ports may include one-way flow valves.

FIGS. 25A-25B and 26A-26B illustrate different relative deformable pump chamber configurations, according to two embodiments. In the two embodiments, both deformable chambers have the same or similar collapsed heights and lengths, but the embodiment illustrated in FIG. 26A has a greater collapsed width than the chamber illustrated in FIG. 25A. In addition, during filling, both deformable chamber embodiments expand in one direction (height), as shown in FIGS. 25B and 26B. Accordingly, deformable chambers having the same or similar heights and lengths, but different widths, will cause blood to be expelled at different flow rates (assuming compression at or near the same rate). The deformable chamber illustrated by FIGS. 26A-26B would generate a greater blood flow rate than the chamber illustrated by FIGS. 25A-25B given its relatively larger volume.

FIGS. 27-28 provide illustrative flow generator systems that include multiple deformable chambers together to provide multiple flow rates even by a single displacement mechanism. With reference to FIG. 27A, the flow generator 2700 illustrated includes at least four different deformable chambers, each having a different filled volume due to the different widths. Having the same filled height and length defines a contact area by the displacement mechanism, which allows each deformable chamber to fill and expel as a unit, but vary flow due to the different individual chamber's widths, as shown in FIG. 27B. With reference to FIG. 28A, deformable chambers may be stacked in the height dimension, still maintaining a constant height and optionally a constant length, but varying in width. As shown in FIG. 28B, a flow generator 2800 having this arrangement can be utilized to define an array of varying blood state (e.g., different blood within each chamber) and blood flow (varying by chamber width). In some embodiments, instead of varying the width of the deformable chambers, their length may be varied, resulting in a symmetric array of outlet ports, while still achieving variable flow rates.

FIG. 29 illustrates a schematic of an assay test system utilizing multiple deformable chambers as a flow generator, according to one embodiment. According to this embodiment, multiple deformable chambers, each having approximately the same or similar height and length, but varying widths, are stacked. An outlet valve from each of the deformable chambers is provided in fluid communication with one or more test conduits of the test chamber or chambers. Thus, varying blood state, blood flow rates, and surface conditions can be achieved. Any number of chambers, blood states, and/or test conduits with different surface conditions can be provided to achieve the desired exposure conditions.

Apparatus—Test Receptacles

As described above, blood flow is generated from the blood chamber or other blood supply either through open test conduits or into closed test wells. The open or closed test receptacles are coated with different surface substrate treatments to create the desired representative exposure conditions. The coating substances may include thrombotic reactive species and adhesion molecules, such as the chemical agents and reagents described above. Blood may be exposed to the surface coating substances for any duration of time, which may be consistent between all test conduits or test wells, or may vary between test conduits or wells. In certain embodiments, the first and second surface substrates and/or the first and second blood flow rates are selected through a quasi-random process. As used herein, the term "quasi-random" refers to low-discrepancy mathematical sequences, as known in the art. For example, the surface substrates may be selected through a Sobol sequence.

Figure 30:
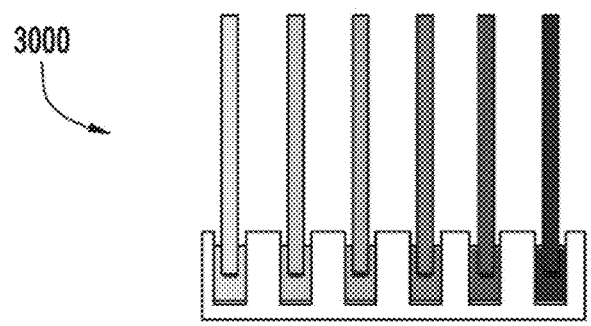
FIGS. 30-32 are schematics, each illustrating an embodiment for coating the blood contacting surfaces of test receptacles with a surface substrate.
Figure 31:
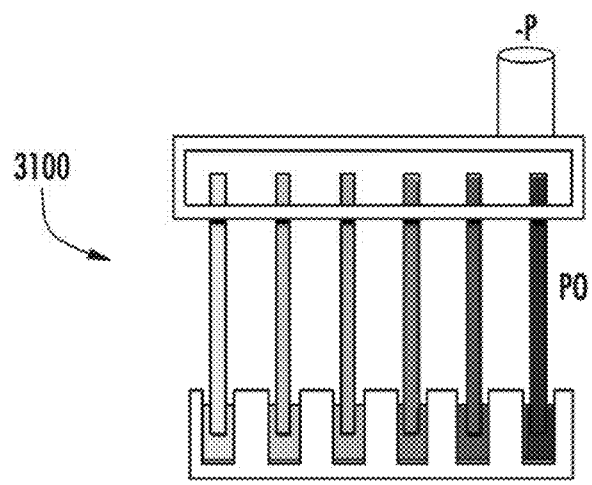
Figure 32:
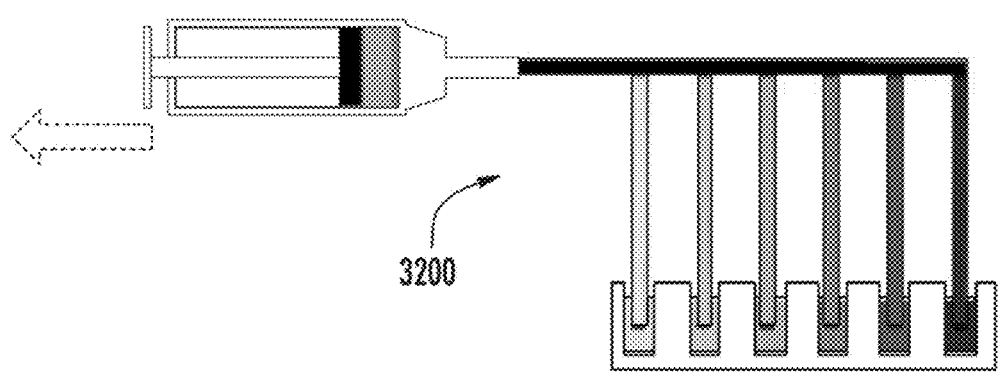

FIGS. 30-32 illustrate some of the various means that may be used to coat or treat the blood contacting surfaces of the test chambers. Given the multitude of test wells and/or conduits that will be utilized, for example, at least one conduit or well per unique set of flow, surface, and surface condition combination, it is desirable to provide a relatively efficient, high-throughput method of coating the test chamber surfaces. According to one embodiment for coating test conduits of the test chambers, such as in an "open" system, wells may be provided that correspond to each of the multiple conduits and that have the same or similar footprint or layout as the array of test conduits. Each well is then filled with the desired coating substance or substances in solution, such as by automated means (e.g., a robotic pipette, etc.) or manually. The test conduits are then lowered into the corresponding wells and the solutions drawn into the test conduits. FIGS. 30-32 illustrate different examples for drawing solutions from the wells into the test conduits. FIG. 30 illustrates the solutions being drawn into the test conduits from the wells utilizing capillary action. FIG. 31 illustrates an embodiment in which a pressure differential is generated, such as via a vacuum source in communication with the opposite ends of the test conduits. Thus, the pressure differential is great enough to retain a column of the solution in the test conduits. FIG. 32 illustrates an embodiment by which a volume displacement means, such as, but not limited to, a syringe pump, bag, etc., is utilized to direct the solution from the wells into the corresponding test conduits. The volume displacement means may generate positive or negative displacement. After the test channels are coated, non-adherent substances may optionally be flushed by inducing some nominal flow rate/wash rate using washing buffer using a flow or pressure source set to run at the nominal condition. According to some embodiments, the test conduits may be first coated before being included within the test chambers, such as those embodiments in which the test conduits are cast into a composite structure.

Figure 33:
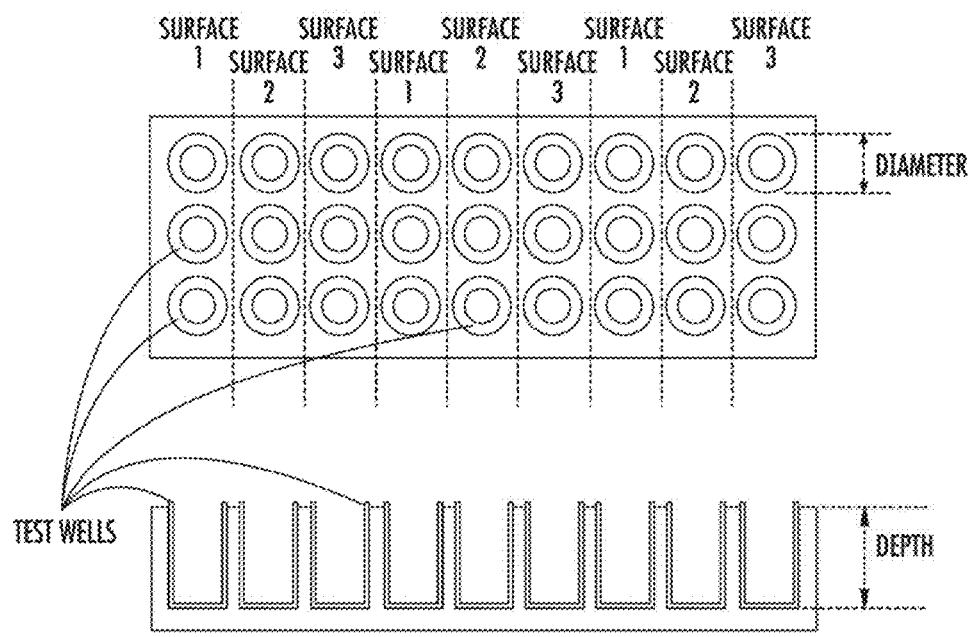
FIG. 33 is a schematic, illustrating one embodiment of an apparatus containing multiple test wells and their corresponding surface substrate conditions.

FIG. 33 illustrates a schematic diagram of an apparatus containing multiple closed wells, according to another embodiment. In this embodiment, one or more multiple wells are provided instead of conduits having an inlet and outlet. Each of the well walls is coated with different substances, concentrations of substances, and/or combinations of substances to create the desired representative exposure conditions. As illustrated in FIG. 33, the wells may be provided as one or more multiple well plates, such as, but not limited to, conventional 24, 48, or 96 well plates, or special made plates having any desired number of wells. According to one embodiment, each well has a diameter of approximately 1 mm to approximately 10 mm and a well depth of approximately 1 mm to approximately 10 mm. However, larger or smaller diameters and/or depths may be provided in other embodiments. Despite the larger diameters relative to the other test conduit configurations described herein (e.g., 0.1 mm-1 mm), the volume of blood is limited because each chamber is a closed unit with fixed volume rather than an open unit with flow. Accordingly, wells may be coated in a simplified manner by dispensing the desired solution or solutions into the respective wells, such as by automated means (e.g., a robotic pipette) or manually. After initially coated, a washing step is performed to wash the non-adherent substances from the wells. In some embodiments, the wells optionally can be blocked with albumin or other similar material to prevent unwanted interactions with the coating solutions and/or blood content.

Figure 34:
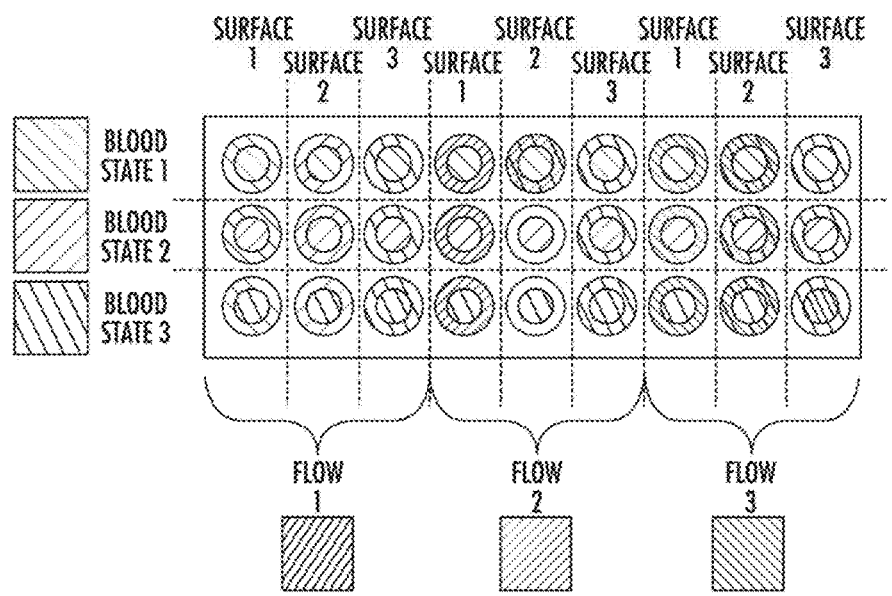
FIG. 34 is a schematic, illustrating one embodiment of an apparatus having multiple test wells and their corresponding blood state, blood flow rate, and surface substrate conditions.

Accordingly, in the example illustrated by FIG. 33, three different surface conditions are applied to the twenty-seven wells. This will allow testing a number of surface, blood flow, and blood condition combinations. For example, FIG. 34 represents one embodiment in which twenty-seven different conditions are tested—three surface conditions, three blood states, and three flow rates. Replicated surfaces allow for the same surface to be tested under different blood and flow conditions. The embodiment depicted by FIG. 34 serves as a simplified illustrative example of the manner in which patterns and groupings of test conditions may populate the multi-parameter thrombotic assay test system, irrespective of whether test wells or open test conduits are utilized. Moreover, while the example shows a three-by-three arrangement, the assay test system arrange need not be symmetric, nor limited to twenty-seven different conditions. For instance there may be more blood conditions than flow conditions, surface conditions than flow conditions, or blood conditions than surface conditions. Accordingly, the multiple parameter assay test system can be constructed and arranged according to the desired exposure conditions and testing techniques.

Figure 35:
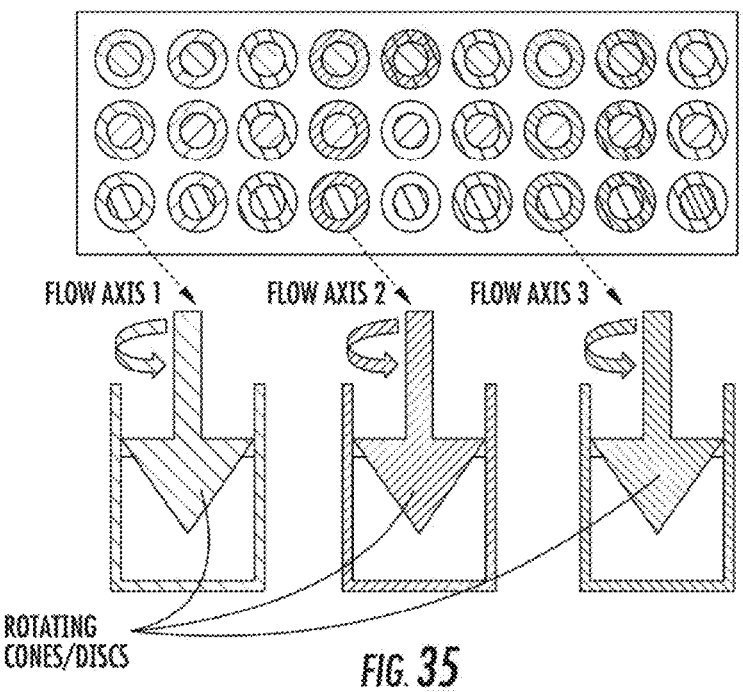
FIG. 35 is a schematic, illustrating one embodiment of an apparatus in which test wells each include a stirring device.
Figure 36:
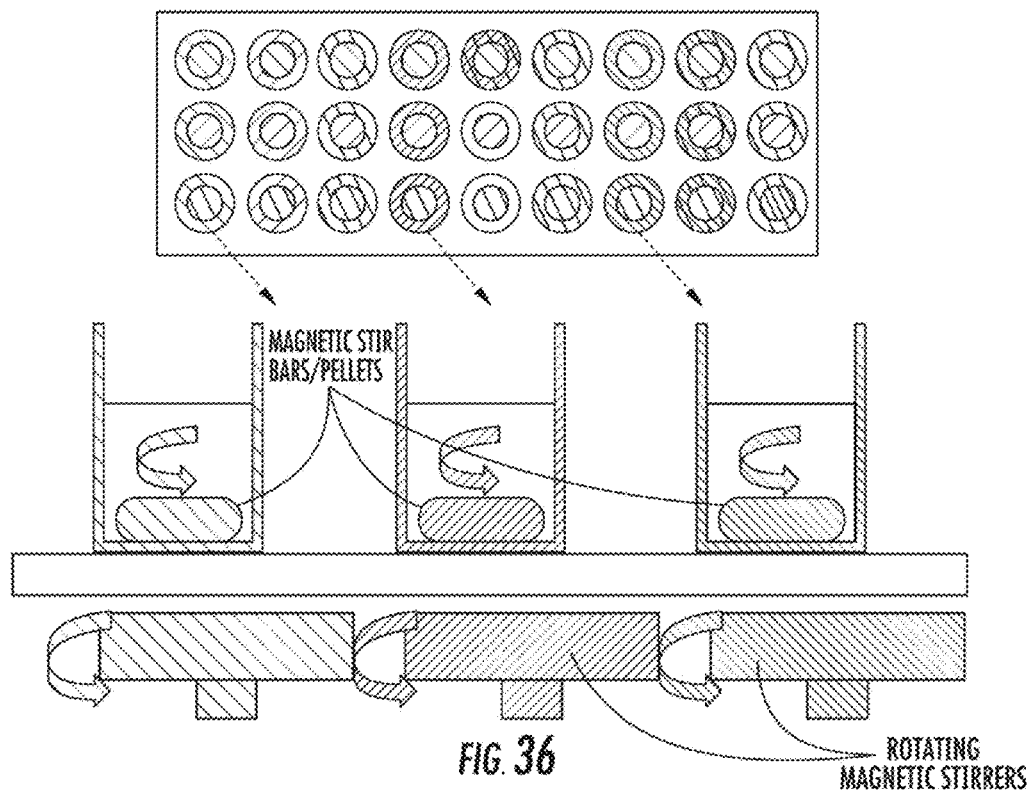
FIG. 36 is a schematic, illustrating another embodiment of an apparatus in which test wells each include a stirring device.

Each test receptacle may include a stirring device operably associated with it to agitate the fluids therein. FIGS. 35-36 illustrate schematic diagrams representing different methods to induce or otherwise represent blood flow in a closed assay test system, according to various embodiments. With reference to FIG. 35, one or more rotating a discs or cones are placed on the top surface of the blood contained in a test well. Each of the discs or cones are rotated to induce a cuvette-type flow within each well, similar to the techniques employed by a multi-axis cone-plate viscometer. According to this embodiment, each test well and rotating disc or cone requires a different axis of rotation to be applied thereto, which can be provided by separate motors in operable communication with each rotating disc or cone and/or by gearing mechanisms in operable communication with one or more motors. FIG. 36 illustrates an embodiment in which one or more magnetic stir bars or pellets are placed into each well, which are rotated by a rotating magnet positioned underneath the respective well, in a manner similar to a standard stir mechanism configured for a multiple-well plate. The stir bar dimensions are smaller than the well diameters to avoid contact of the stir bars with the sides of the wells, which otherwise would undesirably dislodge adherent clot. In some embodiments, each stir bar is coated with a non-reactive, or non-stick, surface, such as polytetrafluoroethylene (PTFE). The blood flow rates may thus be simulated in these embodiments by the rate of rotation or agitation. Accordingly, one or more motors operating at different speeds or one or more rotating magnets rotating at different speeds may be provided to simulate the varying blood flow rates and represent the shear conditions within the closed wells.

Clot Analysis

Following the test run, after the blood has been allowed to interact with the surface in the test conduits or test wells at the prescribed flow conditions, the amount of clot formation or activity is quantified by the clot detector. Three different techniques to quantify clot formation include: (a) detecting and/or quantifying the amount of adherent thrombus formation on the test surface; (b) assaying the blood for the level of clot progression; and (c) measuring time-to-clot formation. To perform assaying on the exposed blood in this second technique, such as utilizing conventional thrombus assay measurements, all blood samples passing through the individual test conduits or wells are stored individually in test chambers instead of pooling into a single or multiple waste chambers. FIGS. 21-22, described above, illustrate various embodiments for collecting exposed blood in individual chambers after being passed through test conduits. In some embodiments utilizing a closed assay test system, the wells into which the blood is deposited may be utilized for analyzing clot formation. However, in other closed assay test system embodiments, the exposed blood may be transferred to other individual chambers, such as according to techniques similar to those techniques for coating conduits described with reference to FIGS. 30-32.

For example, the clot detector may be configured to analyze each test receptacle directly for clot formation. Alternatively, the clot detector may be configured to transfer at least a portion of clot formation that occurs within a test receptacle to a detector chamber and to analyze the amount of clot formation in the detector chamber.

Figure 37:
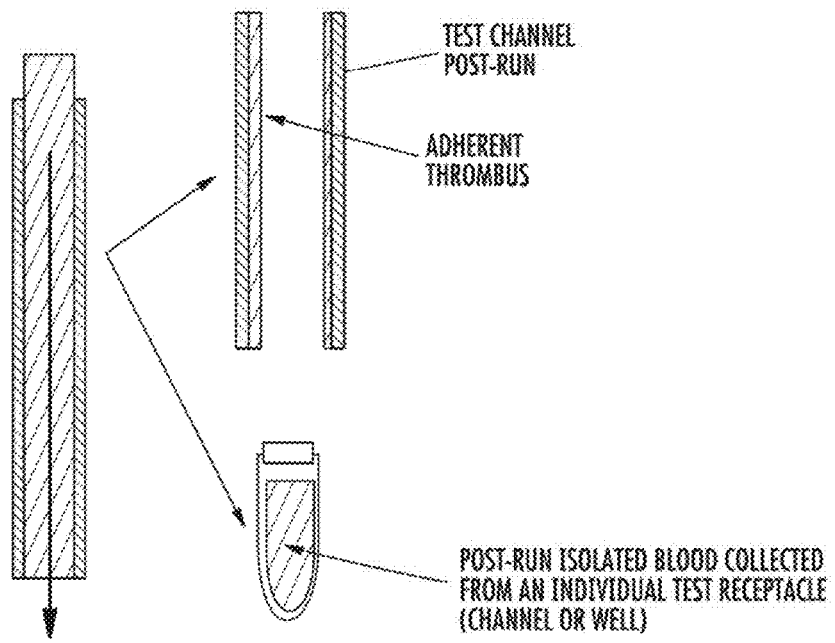
FIG. 37 is a schematic, illustrating one embodiment of a test conduit in which blood flows through the conduit and clot formation remains adhered to the blood contacting surfaces of the conduit after the blood subsequently has passed from the test conduit.
Figure 38:
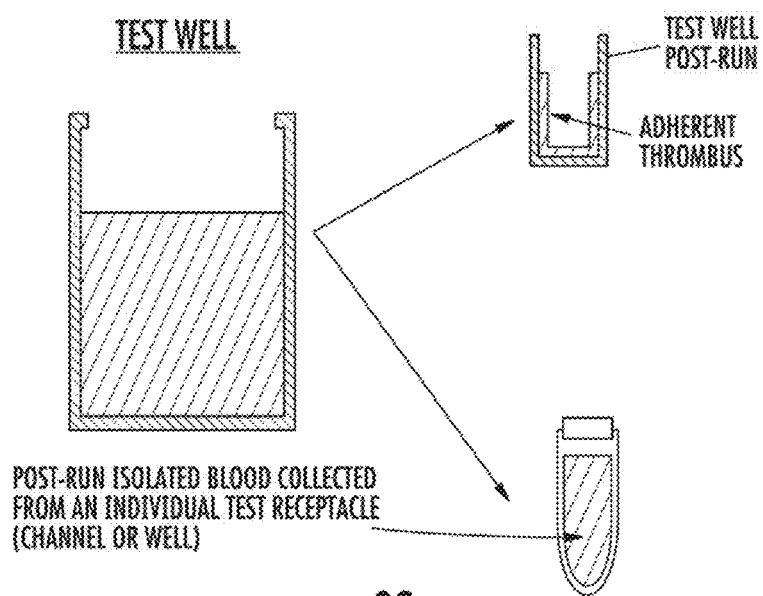
FIG. 38 is a schematic, illustrating one embodiment of a test well in which blood is introduced into the well and clot formation remains adhered to the blood contacting surfaces of the well after the blood subsequently is removed from the test well.

FIGS. 37-38 illustrate schematic diagrams of test conduits and test wells, respectively, at various stages of quantifying clot formation, according to various embodiments. FIG. 37 illustrates a test conduit, such as would be utilized in an open assay test system. In the first diagram, blood is flowing through the test conduit and subjected to the specific surface conditions of the test conduit. The second two diagrams show the test conduit after the exposed blood has been passed therethrough and thrombus adhered to the sides of the test conduit, and an individual chamber into which the exposed blood may be deposited after passing through the test conduit, respectively. Accordingly, the adherent thrombus remaining in the test conduit can be measured, and/or the exposed blood within the individual chamber can be assayed according to conventional thrombus assay techniques to quantify clot formation. FIG. 38 similarly illustrates a test well in a closed system with exposed blood contained therein, and an empty test well with adherent thrombus and a separate individual chamber containing the exposed blood after exposure to the test conditions within the test well. Like FIG. 37, adherent thrombus can be analyzed that remains in the test well, and/or the exposed blood within the individual chamber can be assayed to quantify clot formation.

When the test receptacle itself (test conduits or test wells) is analyzed directly to quantify adherent thrombus, the conduits or wells may undergo a washing stage to wash free non-adherent blood. When utilizing test wells, such as in a closed system, washing may be performed by a series of suctioning to remove the exposed blood and filling and emptying the wells with washing buffer. Any number of wash cycles may be performed, such as, but not limited to, between 2 and 10 repeated cycles. Similarly, the wash buffer may be retained within the test conduits or wells for any duration of time, such as, but not limited to, between approximately 30 second and approximately 10 minutes. Washing may be performed with or without agitation in the wells (e.g., rotating disc or cone, stir bars or pellets, vibration, etc.). Wash buffer can be passed through the test conduits utilizing any of the previously described flow generator devices (e.g., pressure, displacement, etc.), delivering the wash buffer in lieu of blood. However, according to an embodiment, each test conduit experiences the same wash conditions (e.g., buffer flow rates, buffer concentration, number of cycles, exposure time, etc.) to maintain constant at the wash stage, rather than the test conduits being exposed to different flow conditions as in the blood exposure stage.

Accordingly, in embodiments in which the flow generators provide varied flow rates, alterations are made to provide a consistent flow rate across all test conduits. For example, if different pressure sources are utilized to generate the variable blood flows, the pressure sources may be adjusted or switched to a single pressure source during the wash stage. In embodiments in which the blood pathway experiences different resistance, such as additional resistance sections in series with the test conduits, the resistance sections may be removed or replaced to provide consistent resistance across all conduits during washing. In embodiments in which a volume displacement flow generator is utilized (e.g., syringe pump, deformable bag, etc.) to generate a differential blood flow across test conduits, the flow generators may be adjusted to generate the same or similar flow rate when utilized for washing (e.g., adjusting the speed of the driving mechanism or using a separate driving mechanism), or they can be replaced by one or more flow generator devices operable to deliver the wash buffer at the same or similar flow rate.

Figure 39:
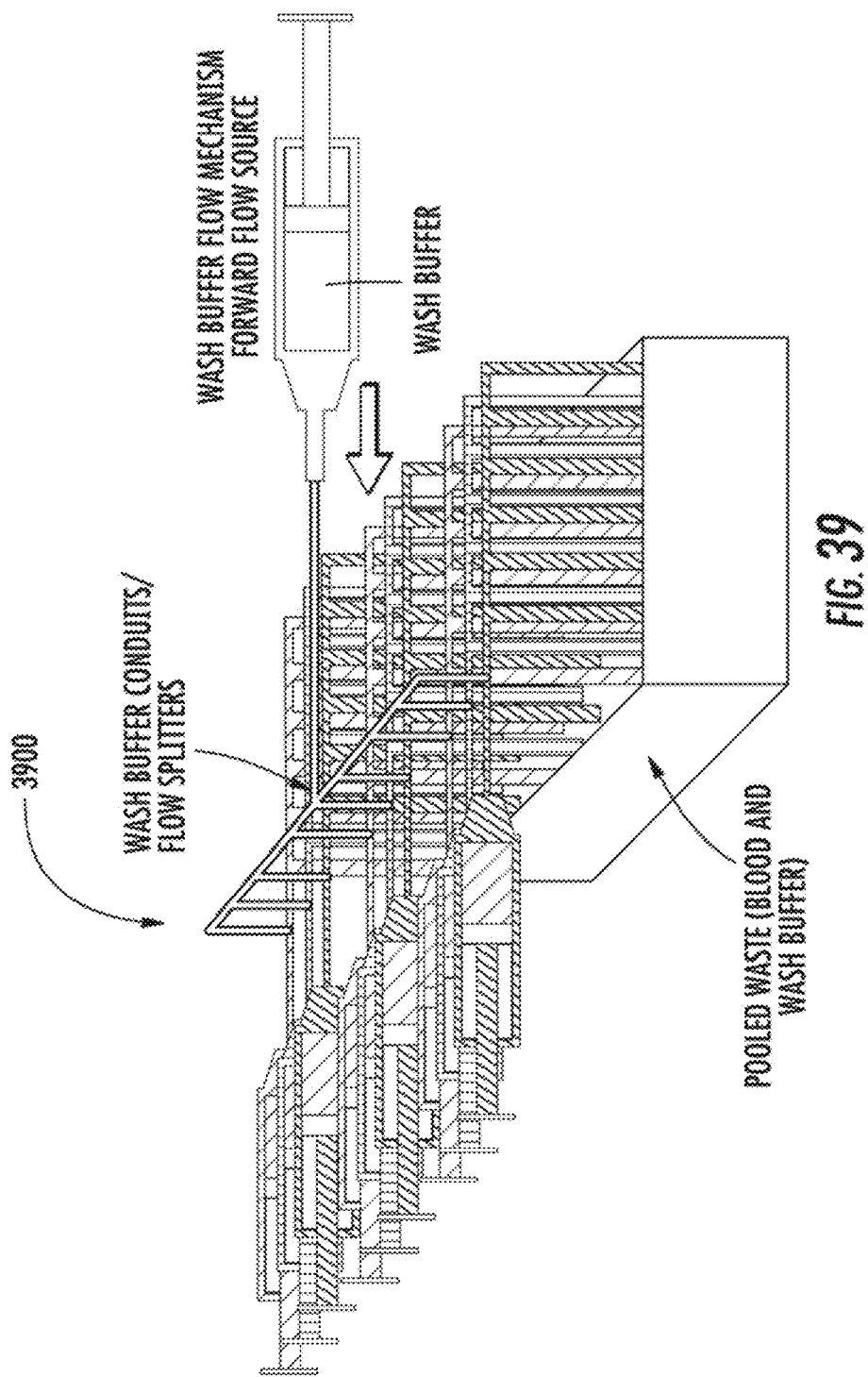
FIG. 39 is a schematic, illustrating one embodiment of an apparatus including a washing mechanism.

FIGS. 39 and 40 illustrate schematic diagrams of two embodiments to facilitate switching between generating a blood flow and running wash buffer through test conduits. According to these embodiments, a valve system, such as one or more directional valves, are placed in-line with the test conduits to allow switching the test conduit pathway from the blood source to the wash buffer source. According to one embodiment, the wash buffer delivery mechanism may be one or more volume displacement devices, such as one or more syringe pumps. The volume displacement device is thus connected to the valve system and operable to eject the wash buffer through the valve system and into the test conduits at or near the same flow rate. In the embodiment 3900 shown by FIG. 39, a single volume displacement device is in fluid communication with the multiple test conduits via a flow splitter and optionally a valve system. The volume displacement device of this embodiment is configured eject the wash buffer from the piston chamber of the syringe, causing forward flow through the test conduits and into a waste chamber or chambers. In the embodiment 4000 shown by FIG. 40, a single volume displacement device is similarly adapted for fluid communication with the multiple test conduits via a flow splitter and valve system. However, according to this embodiment, the volume displacement device is operated in reverse direction, causing a vacuum drawing the wash buffer solution from a basin or basins through the test conduits and into the volume displacement device. In another variation of this embodiment, instead of a separate volume displacement device, flow splitter, and valve system, the original flow generator device or devices can be utilized in a similar manner to draw a wash buffer solution from a separate basin through the test conduits.

Figure 42:
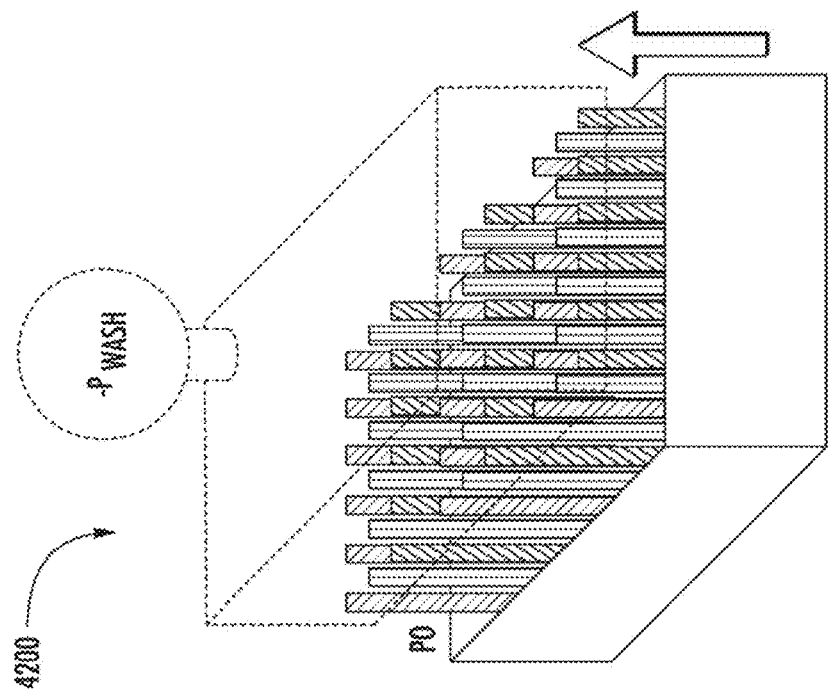
FIG. 42 is a schematic, illustrating still another embodiment of an apparatus including a washing mechanism.
Figure 41:
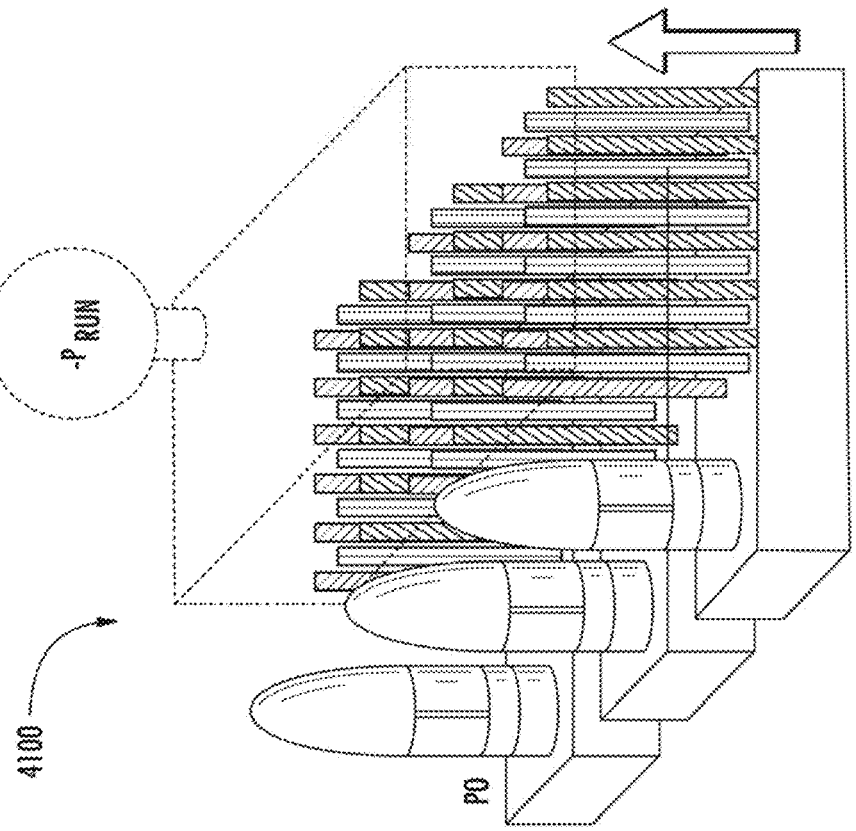
FIG. 41 is a schematic, illustrating yet another embodiment of an apparatus including a washing mechanism.

Other flow generators described herein may similarly be adapted to provide wash buffer flow through the test conduits. For example, FIGS. 41 and 42 illustrate embodiments utilizing a negative pressure flow generator device to create blood flow through test conduits and subsequently to draw wash buffer solution through the test conduits. In the example shown, after drawing blood through the test conduits utilizing one or more negative pressure heads (Prun) shown in FIG. 41, a single pressure head (Pwash) is provided to generate consistent buffer flow through the test conduits shown in FIG. 42. In other embodiments, the blood flow generator pressure head or heads may not be replaced but altered to provide a constant pressure across the test conduits.

Figure 43A:
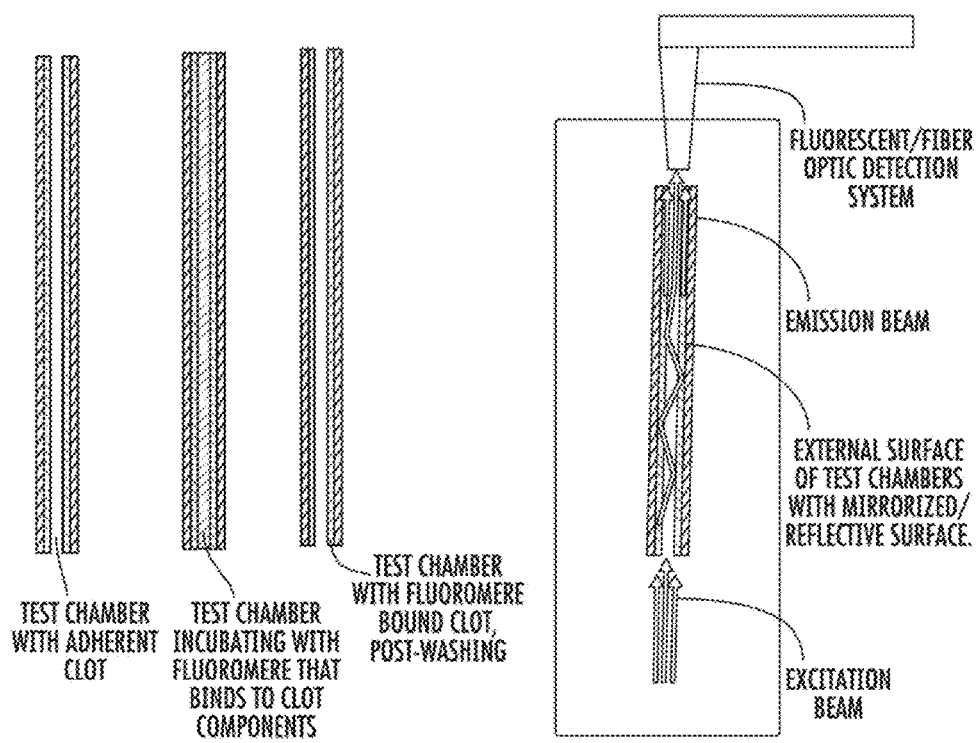
FIGS. 43A-43B are schematics and photographs, illustrating one embodiment of a technique for analyzing clot formation within a test conduit.
Figure 43B:
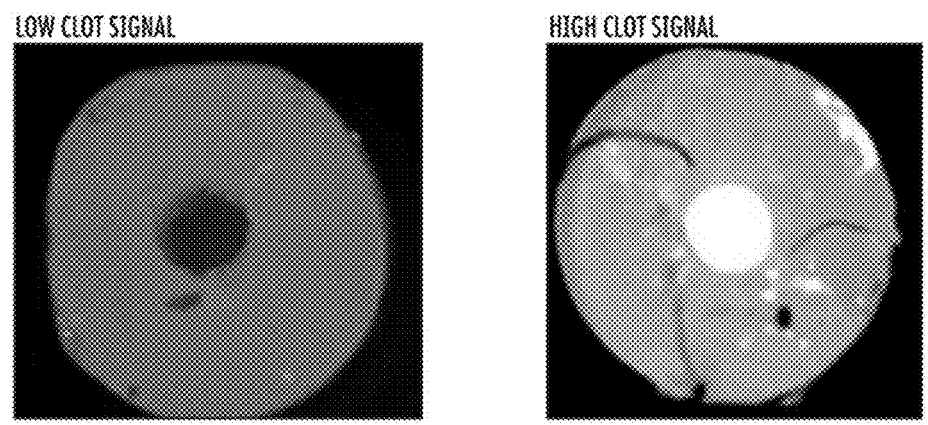

FIGS. 43A-43B illustrate a technique for analyzing thrombus formation within test conduits, according to one embodiment. In this embodiment, fluorescence detection is utilized to detect one or more fluoromeres that adhere to a blood clot, which have been added to the test conduit. In one example, as shown in FIG. 43A, fluoromeres can adhere to blood clot through antibody conjugation, thus permitting detecting of the relative levels of clot within the test conduits utilizing a fluorometer. Accordingly, after each test conduit has been exposed to blood flow, a fluoromere is introduced into the chamber through any flow generating techniques described herein, such as, but not limited to, those described with reference to coating test conduits. After being held within the test conduits for a specified period, and optionally incubated, the test conduits are washed according to any of the aforementioned wash techniques, resulting in fluoromere bound clot remaining within the test conduits. The test conduits are then analyzed by a fluorescence detection system, which excites the fluoromere at its specified wavelength and detects the wavelength emitted from each test conduit. Thus, the level of fluorescence is proportionate to the amount of clotting experienced in the respective test conduits. In one embodiment, to improve detecting fluorescence from the test conduits, a mirrored surface can be applied to the outer surface of the test conduit to cause light emission to be directed in a generally axial direction out of the test conduit for detection. Light directed axially from the test conduit can be detected by a multi-axis fiber optic detection system, for example. FIG. 43B illustrates on-end views of capillary channels showing the optical detection of a low clot signal and high clot signal. Fluorescence is but one of many suitable techniques that can be utilized to measure thrombus formation within the test conduits after exposure to blood flow. In another embodiment, colorimetric assay techniques utilizing a spectrometer can be utilized to measure thrombus formation in a similar manner.

FIGS. 44A-44E illustrate one technique for transferring adhered thrombus, or components of the thrombus, to separate individual chambers for further thrombotic analysis, such as utilizing conventional thrombus assay techniques (e.g., colorimetric assays utilizing a spectrometer or fluorometric assays utilizing a fluorometer) according to one embodiment. In some embodiments, the components present in a thrombus are enzymes, such as lactate dehydrogenase ("LDH"), which degrade a substrate and induce a colorimetric of fluorometric change. In these cases, a substrate may be incubated directly with the clotted test surface in solution and after a given incubation time (e.g., from about 5 minutes to about 1 hour) placed into an individual chamber for assay analysis. In one example, as shown in FIG. 44A, a reagent or wash fluid is drawn into the post-run test conduits to react with and/or release some component of the clot formed therein. According to various embodiments, the solution may include a substrate, such as is described above, or a cell permeabilizer (e.g., Triton-X, etc.). The fluid is provided in on one or more chambers and may be drawn into the test conduits according to any flow generator means described herein, such as those for coating test conduits. FIGS. 44B-44C illustrate the reagent or wash fluid retained within the test conduits for a period of time prior to transfer to individual chambers for subsequent analysis. In one embodiment, the test conduits may be incubated prior to washing into the individual chambers. As shown in FIG. 44D, after the reagent or wash fluid has had time to react with the thrombus within the test conduits, the contents of the test conduits are transferred to individual collection chambers (e.g., a multiple well plate having a configuration and layout matching the test conduit arrangement, such as is shown in FIG. 44E). In one embodiment, this transfer is performed utilizing a multiple-channel pipette-like technique.

In some embodiments, an extra stage of binding is performed, whereby enzyme-linked antibodies are added to the test conduits. In these examples, the antibody antigen is directed towards some aspect of the clot, such as the platelet (e.g., through CD61, CD62, CD42b, CD110, p-selectin, activated IIb/IIIa receptors, platelet-leukocyte aggregates, PAC-1, or other standard markers of the platelet) or fibrinogen. After washing, the enzyme-linked antibodies' reactive substrate is transferred to a multi-well format for measurement. In another embodiment, after the clotted test conduits have been washed, fluoromere-conjugated molecules, such as conjugated-antibodies, or other agents, such as fluoromere conjugated phallocidin, are added to the individual chambers, which are directed towards some aspect of the clot, such as the platelet, fibrinogen, or actin. Multiple different conjugated antibodies having antigens that are different components of a clot are utilized to allow a different fluorometric or colorimetric substance to be used for the different clot components, thus, allowing for differential detection of different clot components.

Accordingly, once exposed blood, thrombus, and/or other substrate is delivered to individual chambers corresponding to each test conduit (or similarly removed from test wells), conventional thrombus assay techniques (e.g., colorimetric assays utilizing a spectrometer or fluorometric assays utilizing a fluorometer) can be performed to measure the level of clot formation. The individual chambers containing the washed contents of the test conduits optionally may be incubated.

In some embodiments, exposed blood is assessed for clot progression. For example, standard blood-borne markers of thrombosis activation, such as, but not limited to, activated platelets, leukocyte platelet aggregates, fibrin degradation products, and/or prothrombin fragments can be detected. In one example, these markers can be detected utilizing standard flow cytometry techniques in combination with the addition of fluorometric antibodies to the samples of blood, and/or a fluorescence-activated cell sorting ("FACS") machine, or utilizing standard enzyme-linked immunosorbent assay ("ELISA") techniques.

Figure 45:
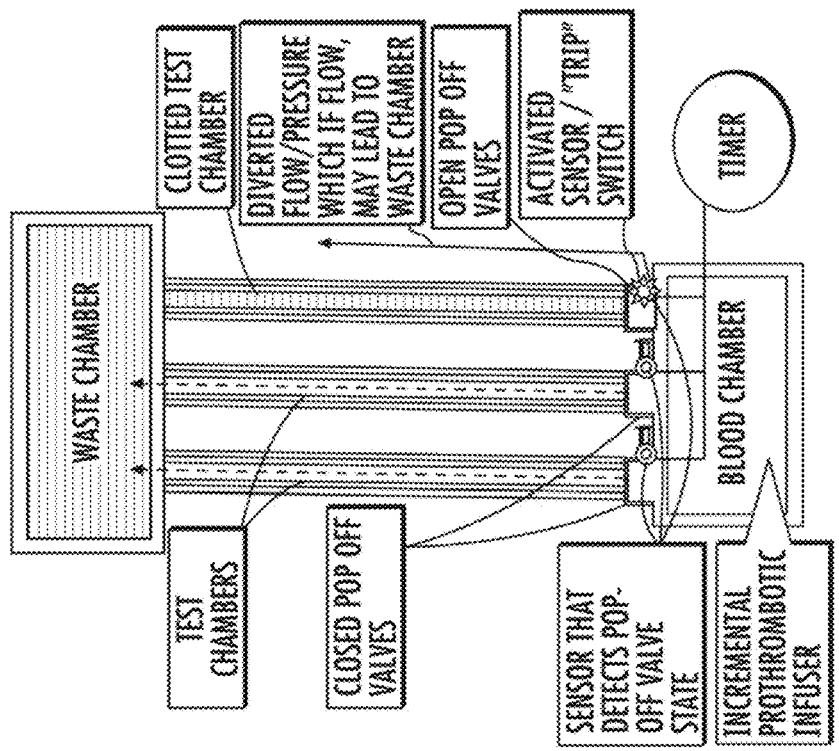
FIG. 45 is a schematic, illustrating one embodiment of a system for performing time-to-clot analysis.

As described above, other clot detection techniques may be utilized. For example, FIGS. 45-56 illustrate various embodiments utilizing the time-to-clot detection technique. A time-to-clot detection technique allows monitoring each test conduit for reduction and/or cessation of blood flow therethrough. In some embodiments, pro-thrombotic agents are added in small, incremental quantities to further accelerate clot formation. This may be needed given that some of the blood states may contain anti-thrombotic agents as part of the designed test conditions. FIG. 45 illustrates a schematic diagram of one embodiment in which multiple test conduits are analyzed using a time-to-clot detection technique. In this embodiment, the blood generally flows through the individual test conduits from the blood chamber toward the waste chamber (bottom to top in this representation) according to any of the previously described flow generator devices. Each test conduit includes a valve (e.g., a pop-off valve) that is operable to change state upon occlusion. For example, upon significant clot formation, the flow conduit becomes occluded and the valve switches from closed to open to allow redirecting the blood flow from the test conduit to a diverted waste chamber. Sensors or other state detection means are included with each valve to detect a change in the state (e.g., from closed to open), thus indicating the time of complete clot formation. As mentioned, a pro-thrombotic agent may be incrementally added to the blood flow upstream from the test conduits, such as via the flow generator devices utilized to cause blood flow. Pro-thrombotic agents can include, but are not limited to, procoagulants, such as thrombin, thromboplastin, PTT reagent, cephalexin, snake venoms, etc., or platelet activators, such as ADP, thrombin, ristocitin, collagen, epinephrine, etc. As one example, approximately 10 µl of a given concentration of a pro-thrombotic agent will be added to each blood chamber every 30 seconds until clot formation.

Figure 46:
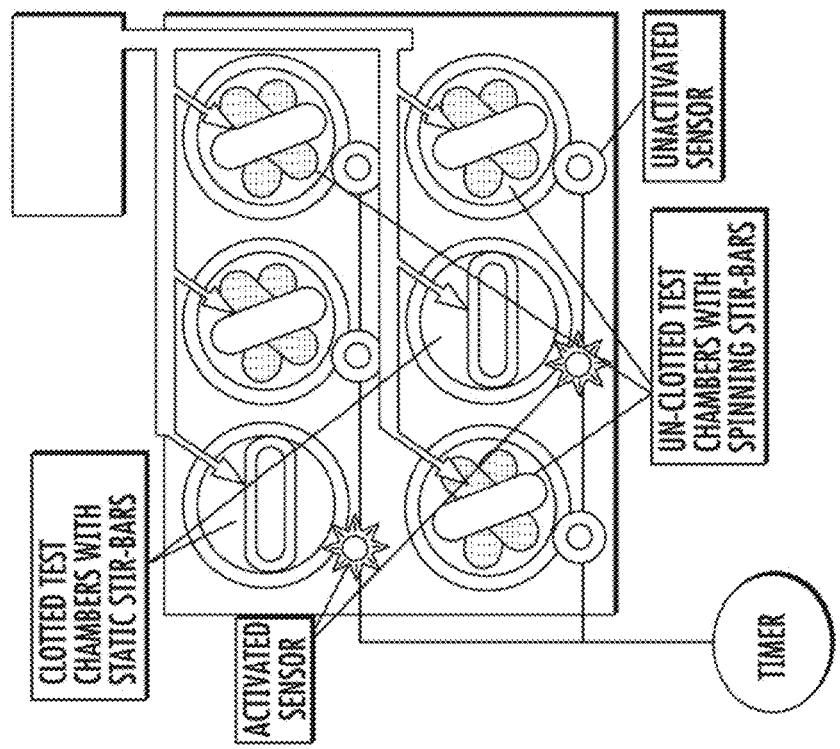
FIG. 46 is a schematic, illustrating another embodiment of a system for performing time-to-clot analysis.

FIG. 46 illustrates another embodiment utilizing a time-to-clot detection technique with a closed system containing test wells instead of test conduits. In this embodiment, the slowing or cessation of magnetic stir bars within each test well indicates the stage of clot formation. Like the embodiment described with reference to FIG. 45, a pro-thrombotic agent may also be added to the test wells to accelerate clot formation. According to one embodiment, one or more sensors associated with each test well (e.g., light, sonic, magnetic sensors, etc.) to differentiate between a rotating stir bar and a stationary stir bar. Comparing the total time-to-clot (or incremental clot stages) can indicate the level of clot formation or clot formation characteristics in each of the individual exposure conditions.

Figure 59:
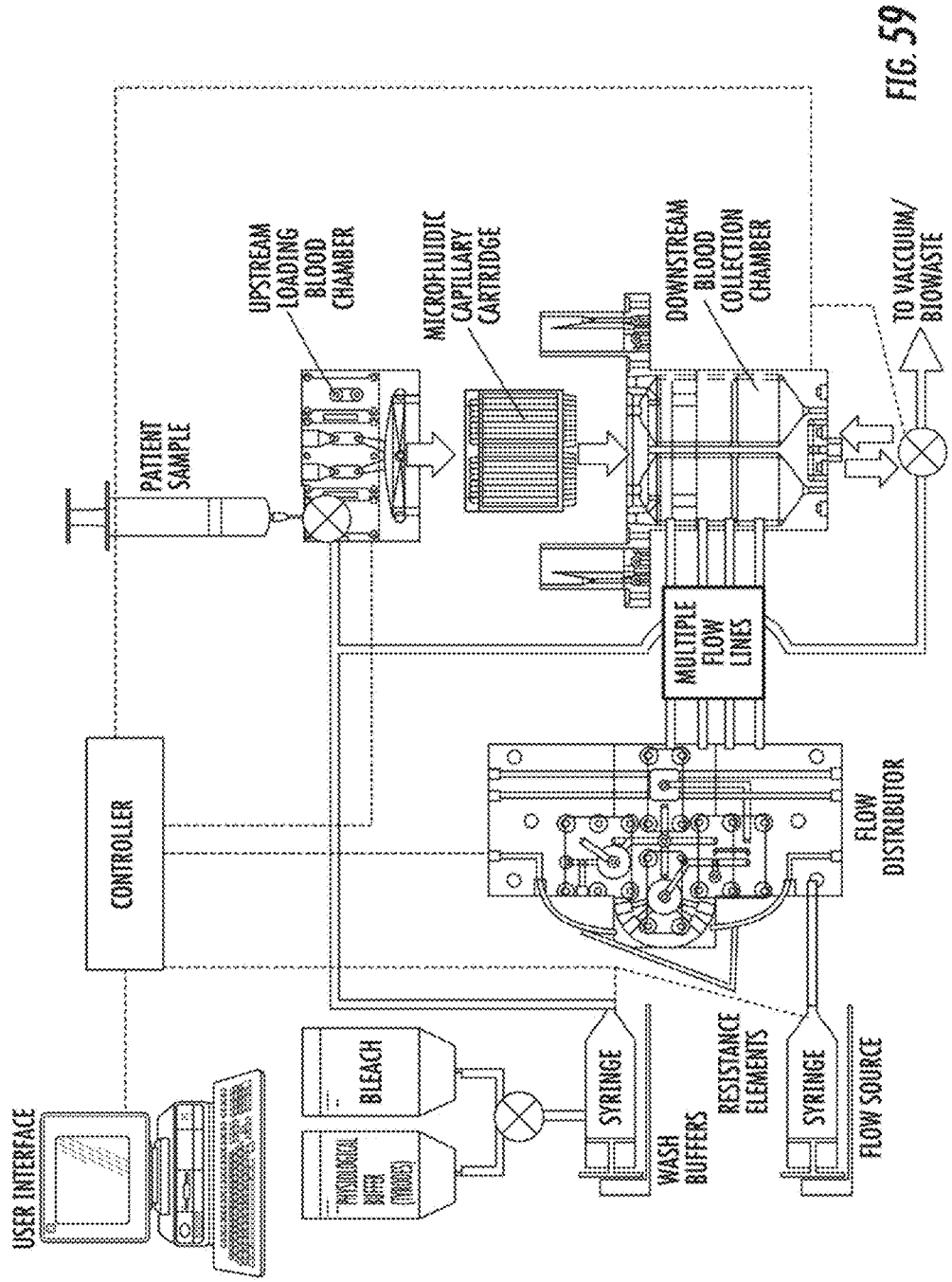
FIG. 59 illustrates an apparatus and system according to one embodiment of the invention described herein.

A preferred embodiment of the apparatus and system is shown in FIG. 59. In this embodiment, a patient's blood sample is loaded, via a syringe, into an upstream blood loading chamber and passed through a microfluidic capillary cartridge into a downstream blood collection chamber in which the clot formation of the blood is analyzed. The capillary cartridge has a plurality of test conduits, and may be in the form of a replaceable (e.g., single-use disposable) cartridge having a array of test conduits with different, pre-selected substrates for assessing the thrombotic state of a particular patient type. A flow source (i.e., flow generator) is provided and flow is distributed to provide varied blood flow rates. A washing mechanism is also provided to clean the blood chamber, conduits, and collection chamber. The blood collection chamber is connected to a vacuum/biowaste collector via which waste from the apparatus is disposed. The system includes a controller to control the timing and/or operation of the apparatus, and a user interface which allows a user to control the apparatus, including initiating a test run and/or a wash run. The user interface may also provide a virtual representation of the plurality of patient data points obtained by the apparatus, and it may show a generated treatment plan for the patient based on the analysis of the patient's blood and thrombotic state.

Methods

Methods for exposing blood to multiple conditions to determine clot activity are also provided herein. In certain embodiments, the methods include, exposing a specimen of blood to one or more blood conditions in vitro to form one or more blood samples; delivering the one or more blood samples into or through a plurality of test receptacles; and analyzing an amount of clot formation that occurs within each of the test receptacles. The blood conditions, test receptacles, and clot formation analysis may include any of the embodiments described herein.

In one embodiment, the one or more blood samples are delivered at a first blood flow rate through a first subset of the plurality of test receptacles and at a second blood flow rate which is different from the first blood flow rate through a second subset of the plurality of test receptacles. A third subset of the plurality of test receptacles has blood contacting surfaces which are coated with a first surface substrate, and a fourth subset of the plurality of test receptacles has blood contacting surfaces which are coated with a second surface substrate which is different from the first surface substrate. For example, at least one of the test receptacles of the first or second subset may also be in the third or fourth subset.

In one embodiment, the one or more blood samples are delivered into or through the plurality of test receptacles using a plurality of flow generators, wherein a first of the plurality of flow generators generates the first blood flow rate through the first subset of the plurality of test receptacles, and a second of the plurality of flow generators generates the second blood flow rate through the second subset of the plurality of test receptacles.

In one embodiment, the one or more blood samples are delivered into or through the plurality of test receptacles in parallel.

Data Analysis

Accordingly, the embodiments described above provide advantageous techniques for collecting vast amounts of raw data related to clot formations in response to graded adjustments in surface substrate condition, blood state, and blood flow rates. The aforementioned systems, devices, and methods can be modified to produce any number of different test conditions, which, when increased, generates a greater amount of raw data for subsequent analysis and application to useful clinical settings.

For example, analyzing the amount of clot may include generating a plurality of patient data points, each patient data point comprising an amount of clot formation and at least one exposure condition selected from blood contacting surface substrate, chemical agent addition, and blood flow rate. In one embodiment, each patient data point includes two exposure conditions. In another embodiment, each patient data point includes all three exposure conditions. Exposure conditions may be selectively varied by degree (rate, concentration), type (chemical agent or agents), and in some cases duration (time).

Figure 47:
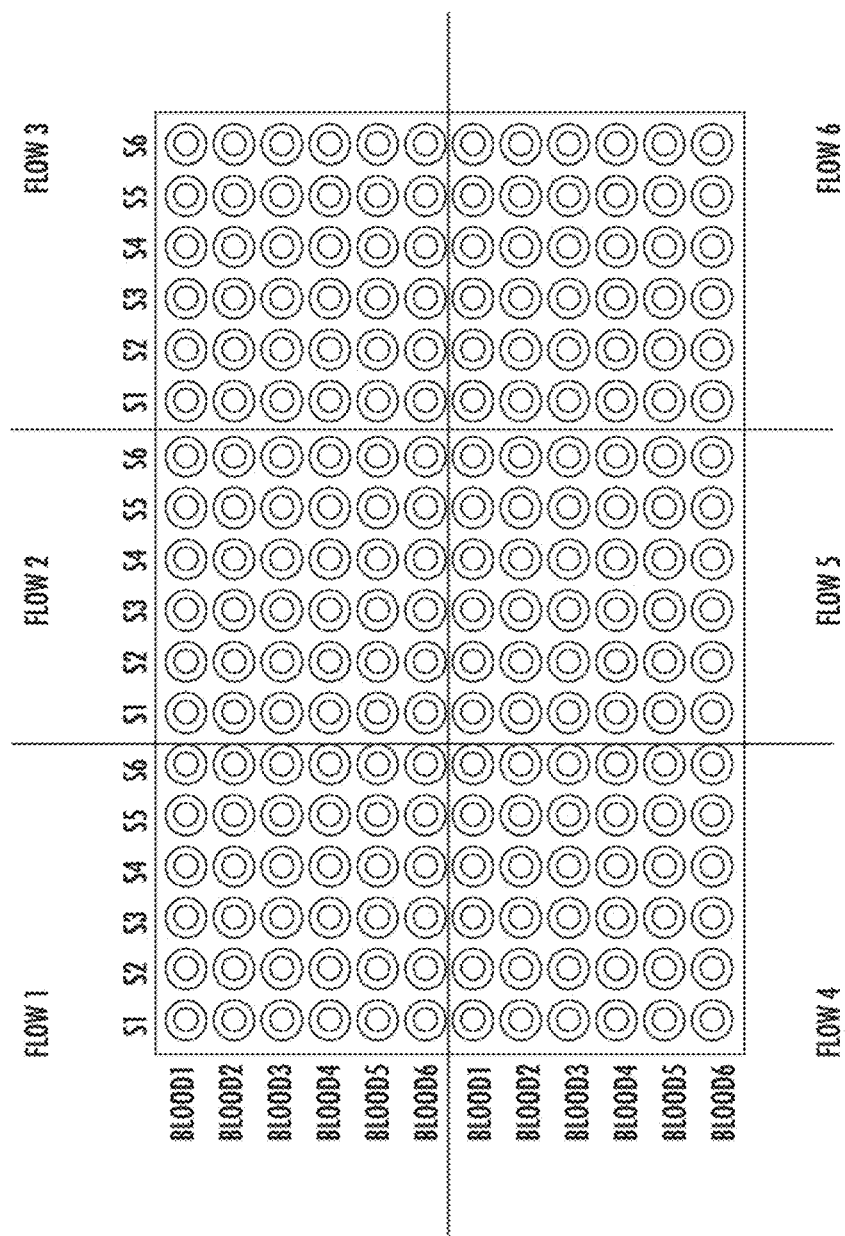
FIG. 47 is a schematic, illustrating one embodiment of a test receptacle array for testing blood samples under an array of exposure conditions.

FIG. 47 is a schematic representation of an array of exposure conditions (test receptacles) providing the ability to test up to 216 conditions (utilizing an 18 by 12 array); although, any number of conditions and/or redundancies may be provided by differently sized arrays. For example, in some embodiments, some or all of the exposure conditions may be repeated one or more time to increase precision of any one exposure condition output through redundant testing. This schematic representation of FIG. 47 also illustrates the manner in which test channels may be arranged, such as grouping different conditions to facilitate overall system layout. For example, grouping similar flows together may facilitate the generation of different flow profiles and possibly minimize the number of flow generator devices utilized. Similarly, similar blood states are shown as grouped together, which may serve to reduce or otherwise simplify the number of blood supply chambers. In general, the more blood state and flow conditions that can be grouped, the more the resultant device may be simplified. Notwithstanding, in situations when conditions cannot be advantageously grouped, conduit systems can be operably adapted to provide fluid communication as needed between the blood chambers, test chambers, flow generator devices, and waste chambers.

In some embodiments, different test conduits (or wells) may be run simultaneously or near simultaneously; while, in other embodiments, all or a subset of the test conduits (or test wells) can be exposed to blood flow for different amounts of time. In some instances by which blood exposure time varies between test conduits or wells, a wash buffer may be delivered upon the cessation of blood flow while the remaining test conduits or wells continue to experience blood flow. The blood exposure time may be varied for any duration, such as, but not limited to, exposure time variations between approximately one minute and approximately ten minutes.

Although symmetric arrays are illustrated by FIG. 47 and in other illustrative figures discussed herein, the arrangements of variations between surface conditions, blood state, and flow conditions need not be symmetric. For example, some conditions may have more variations than others; thus, requiring asymmetric array arrangements. In addition, each combination of conditions is not necessarily required to be tested together.

Mapping a multidimensional blood exposure space requires a large number of data points to be collected. As new blood exposure conditions are considered (e.g., as new drugs are developed), the number of data points required for full mapping grows exponentially. To make this tractable, a quasi-random method (e.g., a Sobol sequence generator) may be used to select the test conditions that would obtain the best representation of the underlying shape or "topology" of the thrombotic and hemostatic profiles, with the fewest number of tests. For example, as shown in FIGS. 55A-55E, an optimized condition set of 192 conditions is represented by four axes (flow, collagen, fibrinogen, and tissue factor), of which a reduced set of data (e.g., a "slice") may be represented based on the conditions of interest.

Moreover, the variations in exposure conditions may differ over time, as further analysis of the determined thrombotic profile as it relates to the exposure conditions may indicate some conditions are redundant or not overly informative. Thus, in some examples, after repeated testing, the exposure conditions may be reduced as the individual parameter relationships and interdependencies are better understood through systematic testing and analysis, such as through unsupervised clustering methods or feature selection methods. In addition, the number of exposure conditions and tested parameters tested may also be reduced from the initial multiple parameter tests because the larger, or more significant, outputs or results are correlated with particular clinical conditions, such as through machine learning techniques (e.g., supervised learning methods, etc.).

Accordingly, different assay test devices may be generated to test for different clinical conditions by reducing or otherwise selecting less than the full set of parameters and exposure conditions. These discretely focused assay test systems also serve to reduce the volume of blood drawn from an individual patient. However, these discretely focused assay tests will likely be application-specific, and less likely to be adapted for more general formulation. Furthermore, while the multi-parameter tests may include data generated solely from the multi-parameter device itself, in some embodiments, the final data-set may incorporate, at least in part, data generated from one or more standard clinical tests such as, but not limited to, prothrombin time tests, partial thromboplastin time tests, platelet counts, hematocrit tests, platelet aggregometry tests, coated bead-type tests, thromboelastography, fibrinogen concentration tests, d-dimer level tests, factor activity tests, and the like, which can provide additional information for use in the overall analysis and diagnosis.

In some embodiments, the final patient data-set may incorporate one or more additional patient data sources, such as, but not limited to, patient genotype data (e.g., single-nucleotide polymorphisms, other polymorphisms, etc.), age, gender, current medication, past medication, or medical history details, such as previous bleeding events (e.g., previous intracranial hemorrhages, previous gastrointestinal bleeding, or other previous bleeding events, etc.) or previous clotting events (e.g., myocardial infarction, embolic stroke, venous thrombosis, pulmonary embolism, or other clotting events, etc.). Incorporation of data from any one or more of the aforementioned additional tests or other data sources may be achieved through conventional data-mining and/or machine learning techniques to limit redundancy and reduce the number of total tests to those that contribute to outcome prediction.

FIG. 48A represents an extraction of the raw test data from an assay test run, according to one embodiment. As shown, there are 1 through n conditions (represented as Z1 through Zn) that are tested by the assay test system, which generate an equal number of data points. These n data points can be mapped in an n-dimensional space (or hyperspace), whereby each individual data point is mapped on a different axis, representing the thrombotic state at each different exposure condition. When running the assay test for an individual, a thrombotic profile of the individual will be deduced from the output of the multiple parameter thrombotic assay test. Thus, the individual's thrombotic profile can be represented in this multi-dimensional (e.g., n-dimensional space) space as shown in FIG. 48B, representing the individual's thrombotic state according to the thrombotic performance under each of the exposure conditions.

Figure 49:
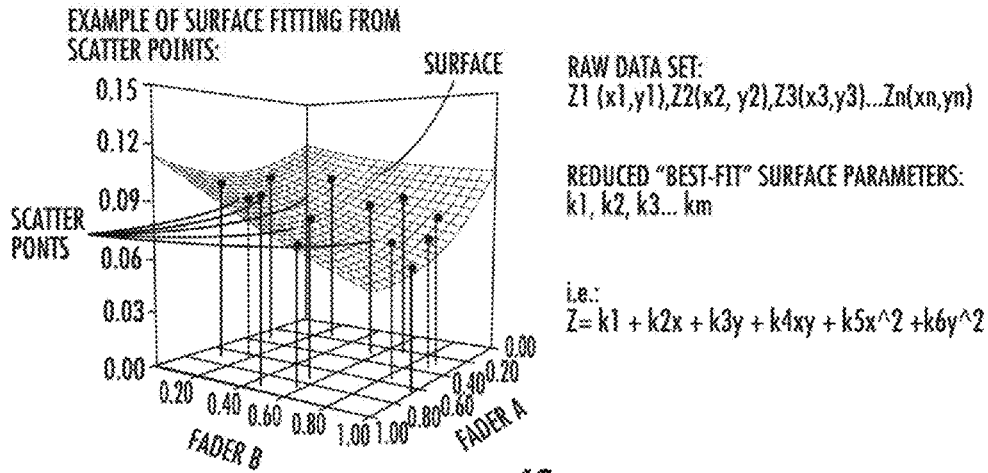
FIG. 49 is a multidimensional representation of one embodiment of an extraction of raw patient test data from an assay test run.
Figure 50A:
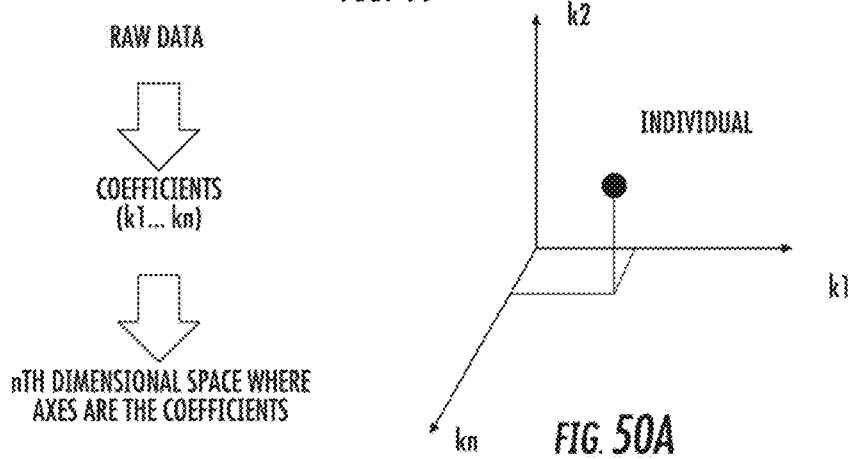
FIGS. 50A-50B are multidimensional representations of one embodiment of an extraction of raw patient test data from an assay test run.
Figure 50B:
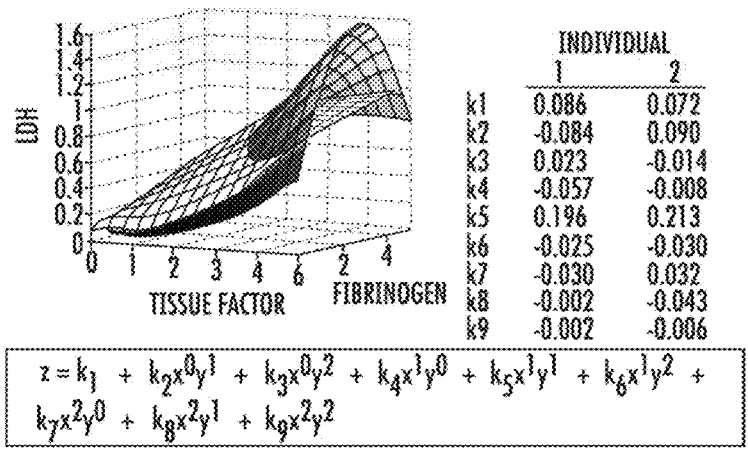

As mentioned, in some embodiments, the exposure condition data set and testing parameters may be reduced to allow for a simpler, more efficient application. According to one embodiment, an exposure condition data set is reduced using best-fit curves, surfaces, and spaces. Accordingly, as shown in FIG. 49, the raw data is mapped to a two or three dimensional representation of the varying conditions. Because the parameters are related, the outputs representing the exposure condition data set can vary smoothly. For example, incrementally varying blood flow, surface conditions, or blood state will result in a smoothed but continuously varying surface, like that shown in FIG. 49. It some instances, the exposure condition data set, once obtained, is rearranged in a different pattern than the test channel layout to facilitate surface fitting. Upon fitting the data set to a curve, surface, or space, the data set can be reduced to a set of equations mathematically representing the curve, surface, or space, and which are characterized by multiple equation coefficients (e.g., a total of m coefficients, represented in the equations by coefficients "k"). Therefore, as shown by FIGS. 50A-50B, an individual's thrombotic profile can be represented by the reduced set of n number of k coefficients instead of the total number of z raw coefficients, providing simpler and more efficient analysis. Instead of each axis represented using the raw data set, each axis can be represented using a reduced data set, such as the set of k coefficients of the best-fit curves, surfaces, and spaces. FIG. 50A shows the data reduced to a set of best fit coefficients which form a representation of the patient's thrombotic profile in a reduced multidimensional space. FIG. 50B shows two different patient's thrombotic profiles represented by reduced data and best-fit polynomial surfaces.

In some instances, the entire set of raw exposure condition data may not be represented by a single continuous surface, but represented by several disjointed surfaces, each of which is represented by a specific best-fit relation. Accordingly, these methods of data reduction imbed functional relationships into the data as the coefficients describe how the parameters vary in relation to one another.

Figure 52:
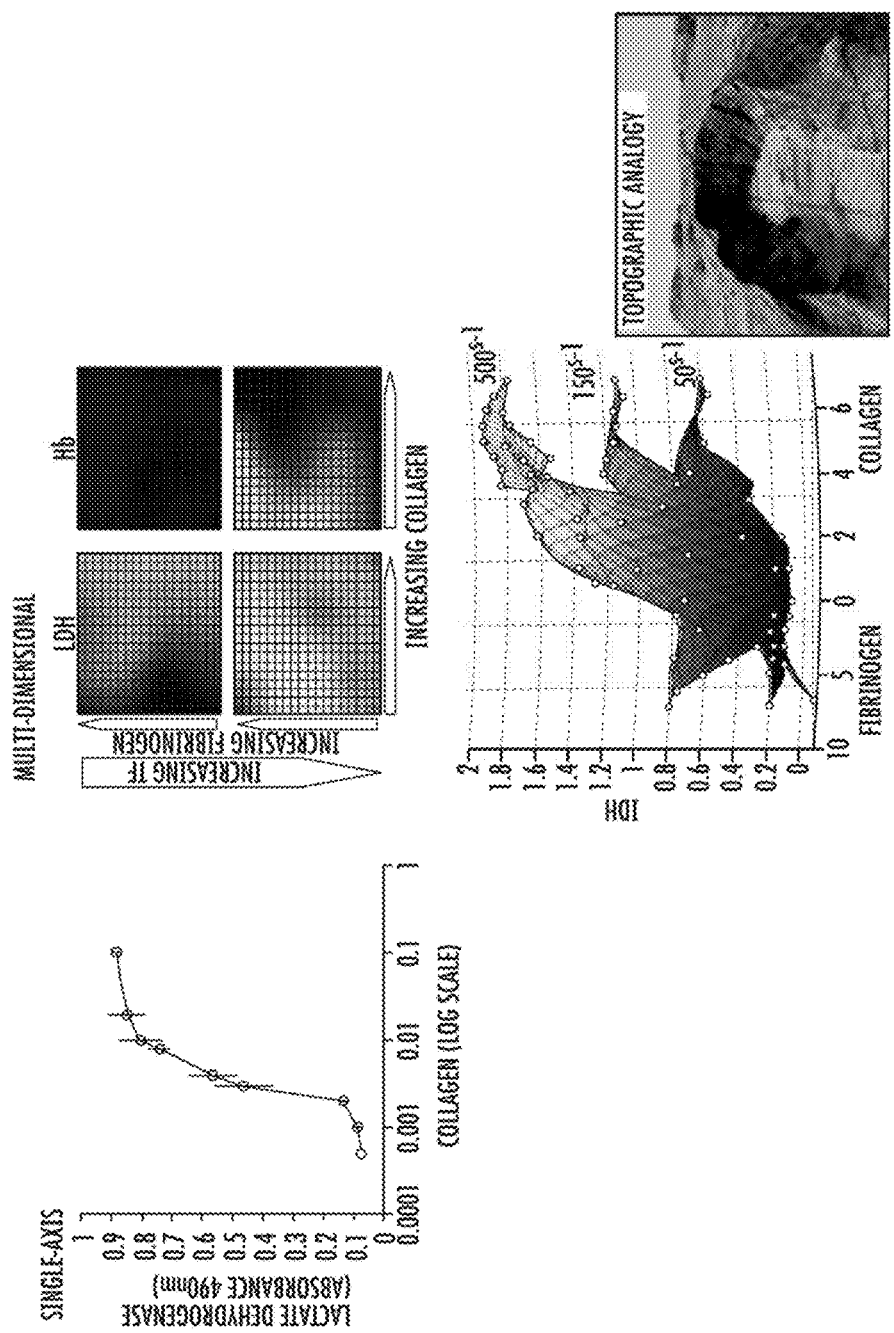
FIG. 52 illustrates various representations of one embodiment of an extraction of raw patient test data from an assay test run.

As shown in FIG. 52, by collecting information on condition-dependent clot formation, the apparatus, systems, and methods described herein are able to map a patient's multidimensional hemostatic/thrombotic state. A single axis, such as surface collagen concentration fails to capture the richness underlying thrombosis, while the disclosed multidimensional representation captures rich, high dimensionality hemostatic "topographic" states of patients, providing a rich phenotypic tool.

While the embodiments described with reference to FIGS. 38-41 and 52 describe reducing the exposure condition data sets, in some embodiments, the exposure condition data may be further simplified using data-mining methods, such as unsupervised learning methods. Unsupervised learning methods may include, but are not limited to, data clustering, independent component analysis, self-organizing maps, and adaptive resonance theories. Unsupervised learning methods can also be used to perform hierarchical cluster analysis. Additional techniques to regularization or normalize may also be utilized to reduce redundancy in the data analyzed and/or gathered.

Figure 51A:
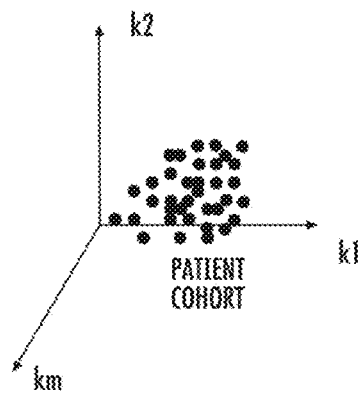
FIGS. 51A-51C are graphical representations of one embodiment of a predictive thrombotic data set in reduced multi-parameter spaces.
Figure 51B:
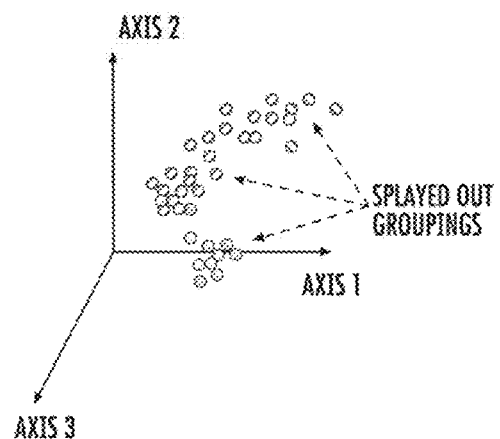
Figure 53:
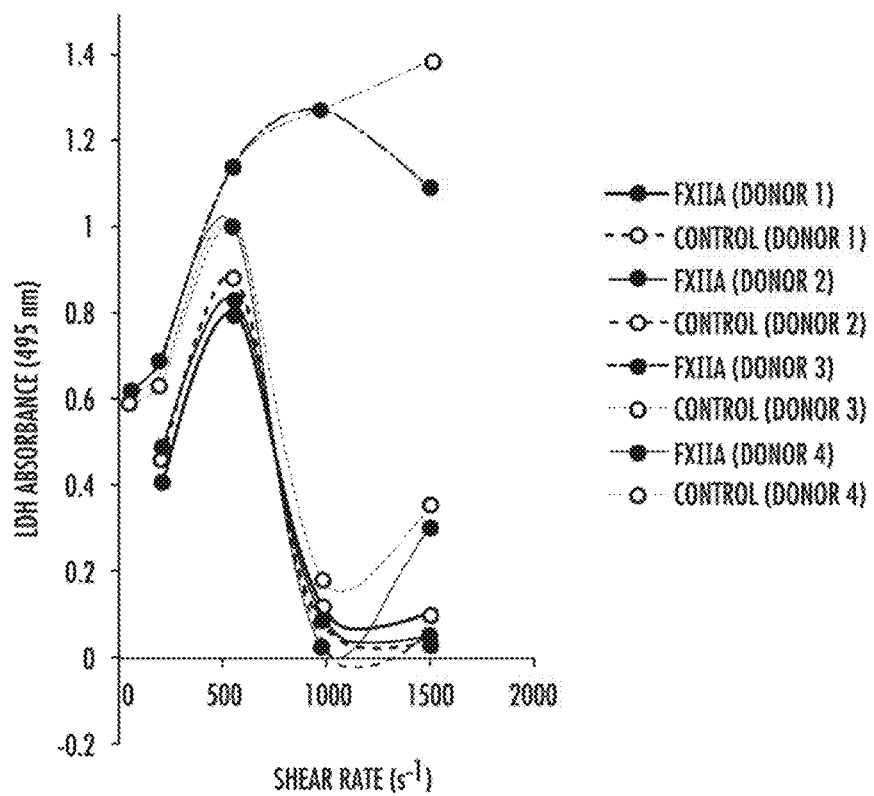
FIG. 53 is a graph, illustrating one embodiment of a multidimensional multi-donor clot formation analysis.

Principle component analysis methods may also be performed to further reduce the data, as another example of data mining techniques. Principle component analysis transforms the data to determine variation, whereby the transformed axes represent degrees of variation. For example, the first axis represents the most variation, the second axis the second most variation, and so forth. Typically, as data sets are reduced in this manner, the axes that do not contribute to variation, or contribute only a minor amount, can be removed from the data set, resulting in a further reduced data set of exposure conditions. Reducing or otherwise re-analyzing exposure condition data using the principle components analysis methods can be performed to identify distinct groupings of patients within a larger set. For example, one or more cohorts of patients can be assessed to generate their thrombotic profile, as shown in FIG. 51A. Subsequently, the thrombotic profile can be transformed by the method of principle components analysis to further identify distinct groups within the cohort of patients by emphasizing variation among the cohort, as shown in FIG. 51B. For example, as shown in FIG. 53, distinct thrombotic profiles are observed between patients. As can be seen in FIG. 53, donor 3 exhibits significantly higher clot formation at higher flow rates than the other donors. At low flow rates, donor 4 is similar to donor 3, but at higher flow rates, performs like donors 1 and 2. These results demonstrate the varying impact of procoagulant at different flow rates and in different individuals, and more generally show the usefulness of identification of distinct groups within a cohort of patients for predictive purposes.

By reducing the raw data set, a simplified assay test system can be developed that tests only the reduced data set, eliminating testing extraneous conditions or at best marginally useful conditions.

Figure 48:
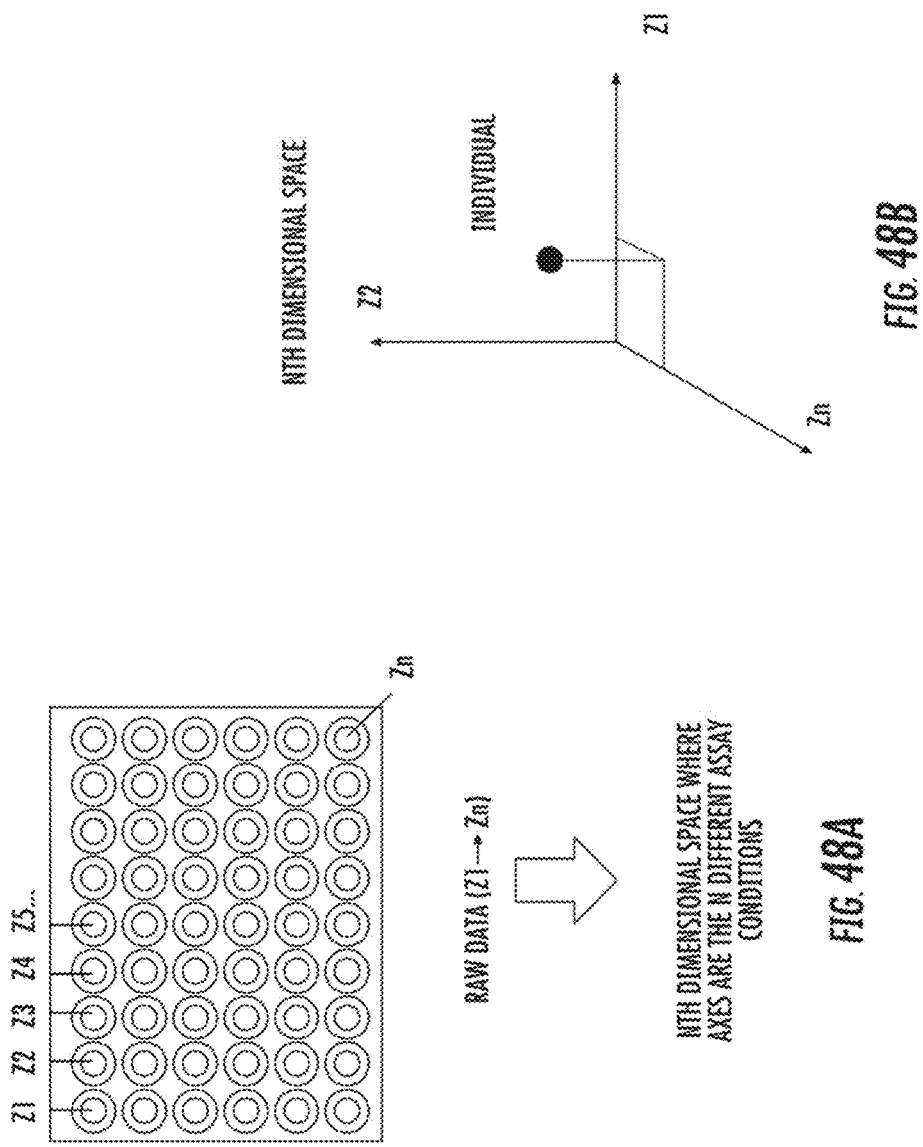
FIGS. 48A-48B are representations of one embodiment of an extraction of raw patient test data from an assay test run.

The varied utility of generating a patient's thrombotic profile can readily be seen using these multi-axis parameter spaces, as shown in FIGS. 48 and 50. In particular, the multi-axis parameters spaces can be utilized to associate the data (e.g., the regions defined in the n-dimensional space or hyperspace) with particular clinical outcomes such as, but not limited to, thrombotic events, bleeding events, drug resistance patterns, thrombotic phenotypes, genetic polymorphisms, and the like. In some clinical uses, the effect of therapeutic drugs can be determined by monitoring, through administering multiple assay tests, where in the multi-axis parameter space an individual receiving the drug is moved after receiving the drug. Moreover, the vast number of degrees of freedom provided by these multiple-dimensioned testing allows distinct drug interactions to be identified to analyze the effectiveness of complex multi-drug regimens. Similarly, these assay tests can be utilized to analyze drug resistance and alternate therapies. For example, resistant individuals can be identified and alternate therapies can be administered, all while performing assay testing to determine movement within the multi-axis space and, thus, the impact on thrombotic activity.

These multiple-parameter assay tests can also be utilized to improve the clinical characterization or "phenotype" of a patient. For example, individuals with specific polymorphisms will exist in one or more different locations in the multi-axis parameter space compared to normal individuals. The ability to locate these phenotypes in the parameter space allows identifying patients that may require differential monitoring, treatments, etc. The usefulness of facilitating identifying and treating phenotypes is tremendous, considering the number of known platelet and coagulant polymorphisms that confer increased risk for thrombotic outcomes such as, but not limited to, heart attack, stroke, or pulmonary embolism.

Figure 51C:
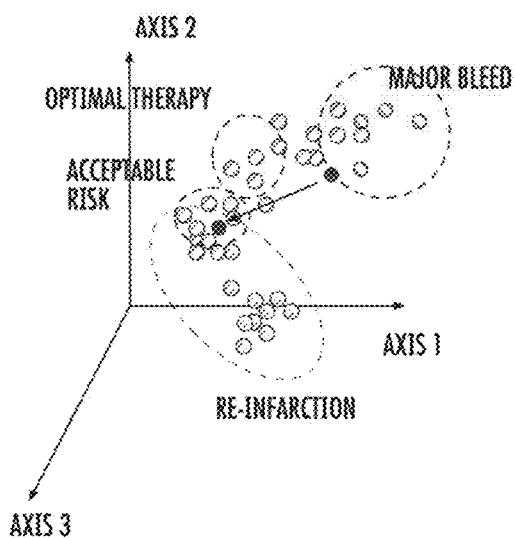
Figure 54:
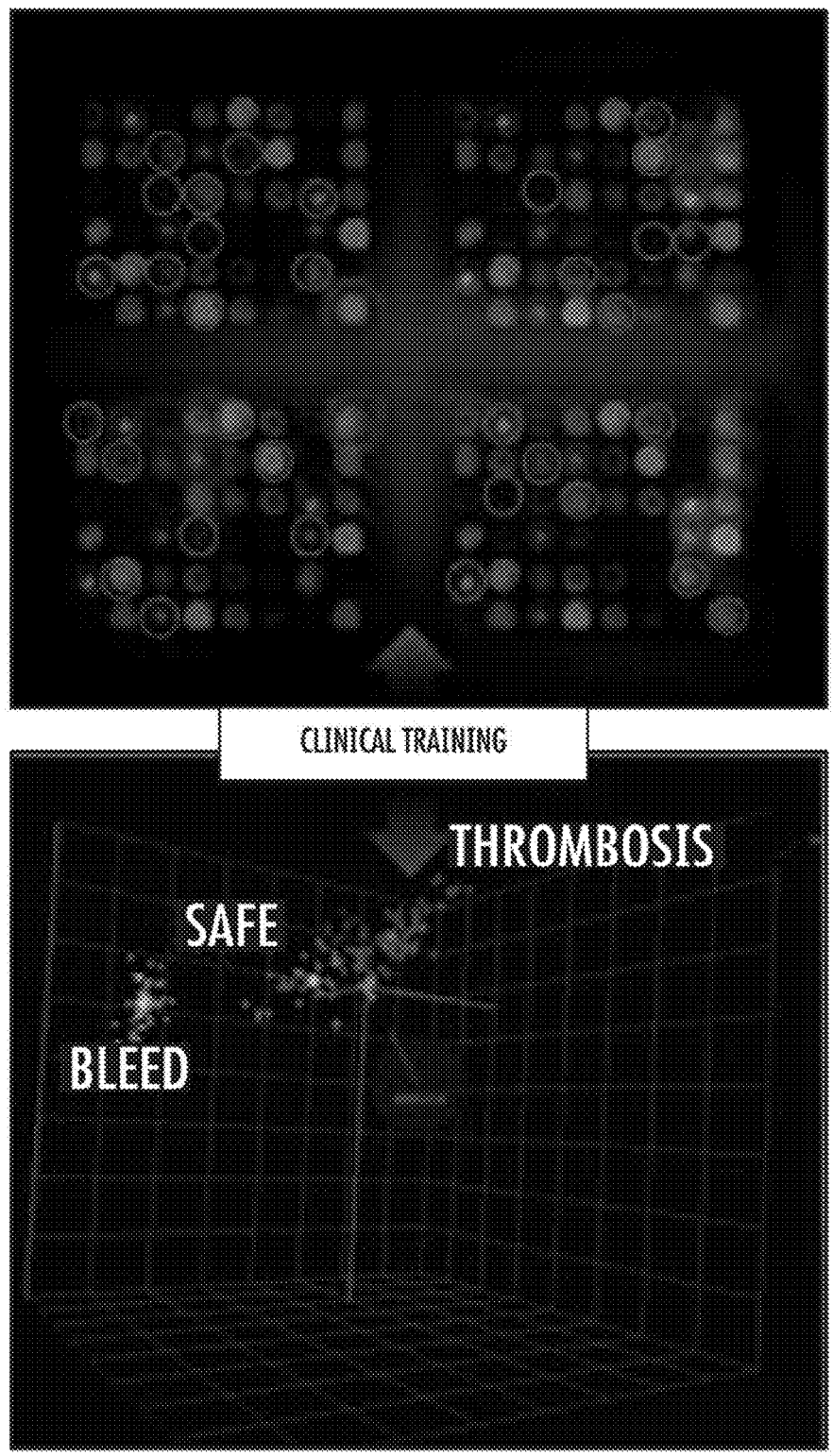
FIG. 54 illustrates one embodiment of a clot risk determination based on a patient's raw data and a set of predictive data.
Figure 55A:
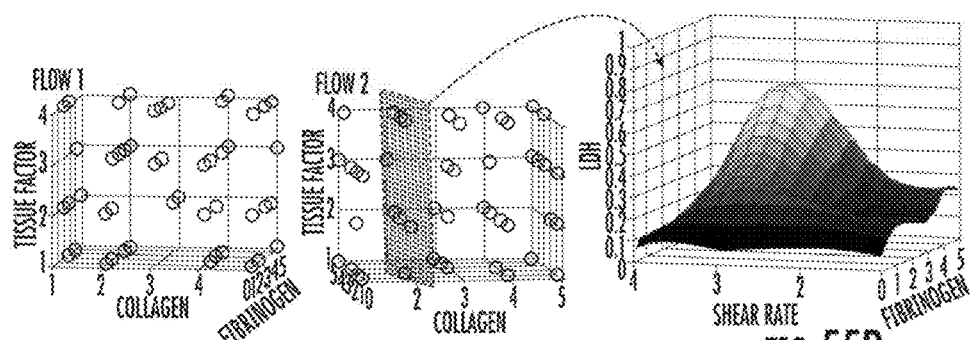
FIGS. 55A-55E are graphs, illustrating one embodiment of an extraction of raw patient test data from an assay test run.
Figure 55B:
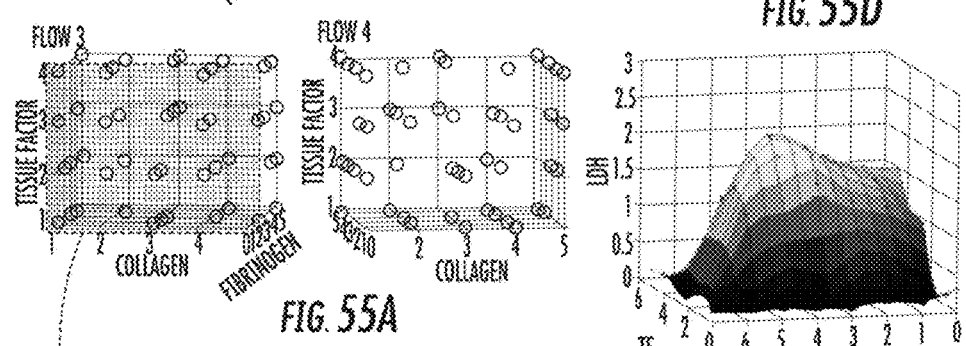
Figure 55C:
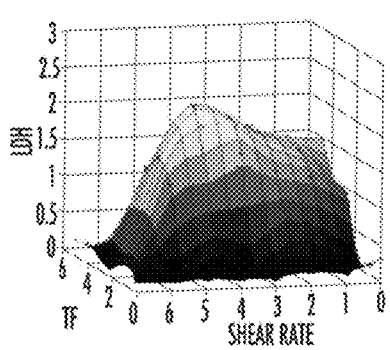
Figure 55D:
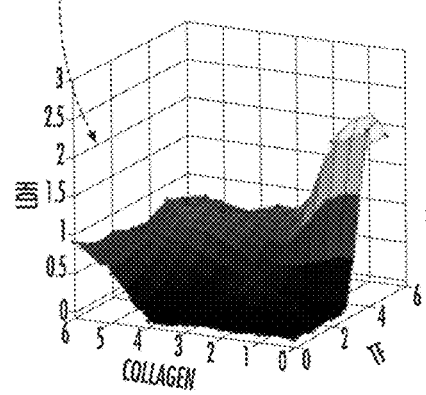
Figure 55E:
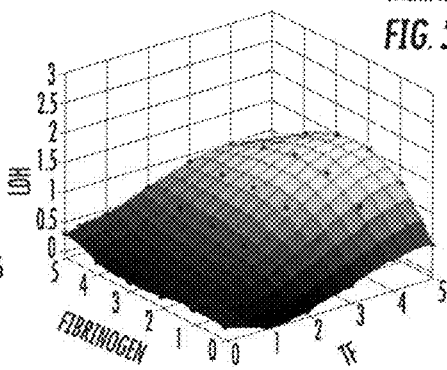

In another example of predicting thrombotic and/or hemmorhagic conditions, the thrombotic profiles of one or more patient cohorts will be determined reduced through any number of the described data reduction techniques. The cohorts may then be followed over time to determine their clinical condition (e.g., therapy outcome, complications, etc.). In this manner, the regions of the reduced parameter space that are associated with different outcomes can be identified, such as in an outcome or condition map, as shown in FIG. 51C. For example, regions at risk for bleeding may be distinguished from regions that are at high risk for thrombotic outcomes, such as re-infarctions. These regions may, thus, generate novel outcome maps. Furthermore, optimal thrombotic profiles that lead to optimal outcomes can be determined from these maps and incorporated in thrombotic therapy and/or the subsequent generation of thrombotic assay test devices. For example, the outcome maps generated from following cohorts of patients to detect clinical outcomes, as shown in FIG. 51C, can then be used prospectively by determining the thrombotic profile of new patients and giving them drug therapies that cause the patients to move to regions of the thrombotic parameter space associated with optimal outcomes. It is likely that different individuals will need different therapies to move to a desired outcome region, depending upon their initial thrombotic state represented by their initial location within the parameter space. Similarly, an outcome map as shown in FIG. 51C allows further optimization of therapy for patients at particularly high risk for a given undesired outcome (e.g., a patient known to have had a recent GI bleed). The thrombotic profile of such a patient may be moved to a region of the parameter space that is in an "acceptable risk" location, rather than the expected "optimal" location, to further reduce the risk of bleeding at an acceptable increased risk of adverse clotting outcomes. FIG. 54 also shows a risk assessment performed by representing a patient's individual thrombotic/hemostatic state as a vector in a multidimensional space where predictive data has been collected.

To generate predictive models between the data sets (or the reduced data sets) and the measured/observed outcomes (e.g., thrombotic outcomes, clinical outcomes, etc.), a variety of machine learning approaches may be used. Supervised learning methods may include, but are not limited to, nonlinear or linear methods (e.g., polynomial response surface models, Kriging, radial basis function approximations, Gaussian process modeling using both Bayesian and non-Bayesian approaches, etc.). In addition, methods including cubic splines, multi-quadric, inverse multi-quadric, quintics, thin plate splines, and many others can be applied when utilizing radial basis function approximations. Other methods of forming predictions between the data-sets and outcomes include, but are not limited to, support vector machines, nearest neighbor methods, artificial neural networks, genetic programming, linear regression, partial least squares projections, decision trees, probabilistic learning methods, instance-based learning logistic regression, and/or any combination thereof.

According to other embodiments, feature selection methods may be used to further reduce the data sets to those aspects or parameters that contribute to the prediction of the particular condition in question (e.g., a thrombotic condition, clinical condition, etc.). Any number of feature selection and/or data-reduction methods may be used to minimize the data-set to facilitate generating a reduced, clinically useful assay. These approaches include, but are not limited to, orthogonal partial least squares discriminate analysis, filtering techniques (e.g., entropy-based, correlation-based, rule-based filtering, information gain filtering, etc.), wrappers, which use the predictive accuracy of a learning method to drive feature selection, such that the collection of features that best form the best predictive model are kept, meta-learning (e.g., ensemble of embedded-based methods, etc.), main-effects analysis, null-hypothesis testing, unsupervised clustering algorithms (e.g., hierarchical clustering, etc.), and/or any combination thereof.

Again, by reducing the initial multi-parameter data set, a simplified assay test system can be developed, which includes only a subset of the entire data set, which are determined to be predictive parameters and/or conditions. Reducing the data set according to any of the aforementioned techniques thus avoids or minimizes testing extraneous conditions or at best marginally useful conditions.

Figure 56A:
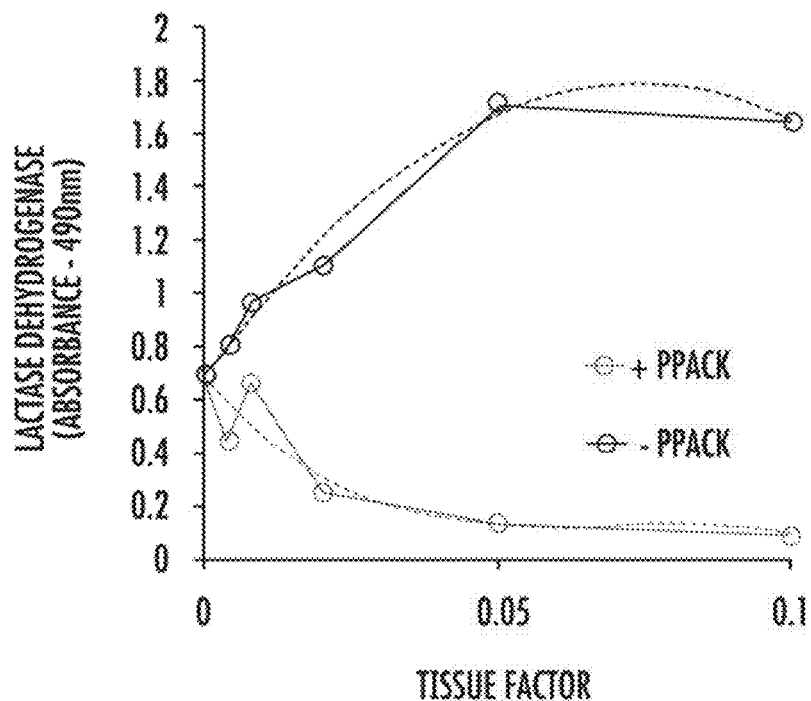
FIGS. 56A-56D are graphs, illustrating one embodiment of an extraction of raw patient data and determination of thrombotic conditions of the patient.
Figure 56B:
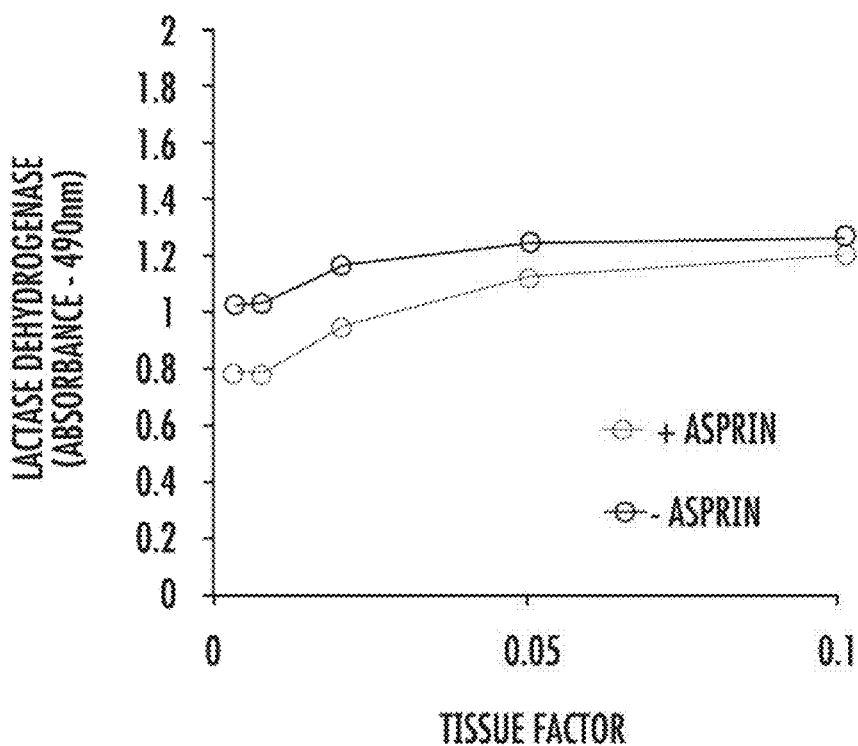
Figure 56C:
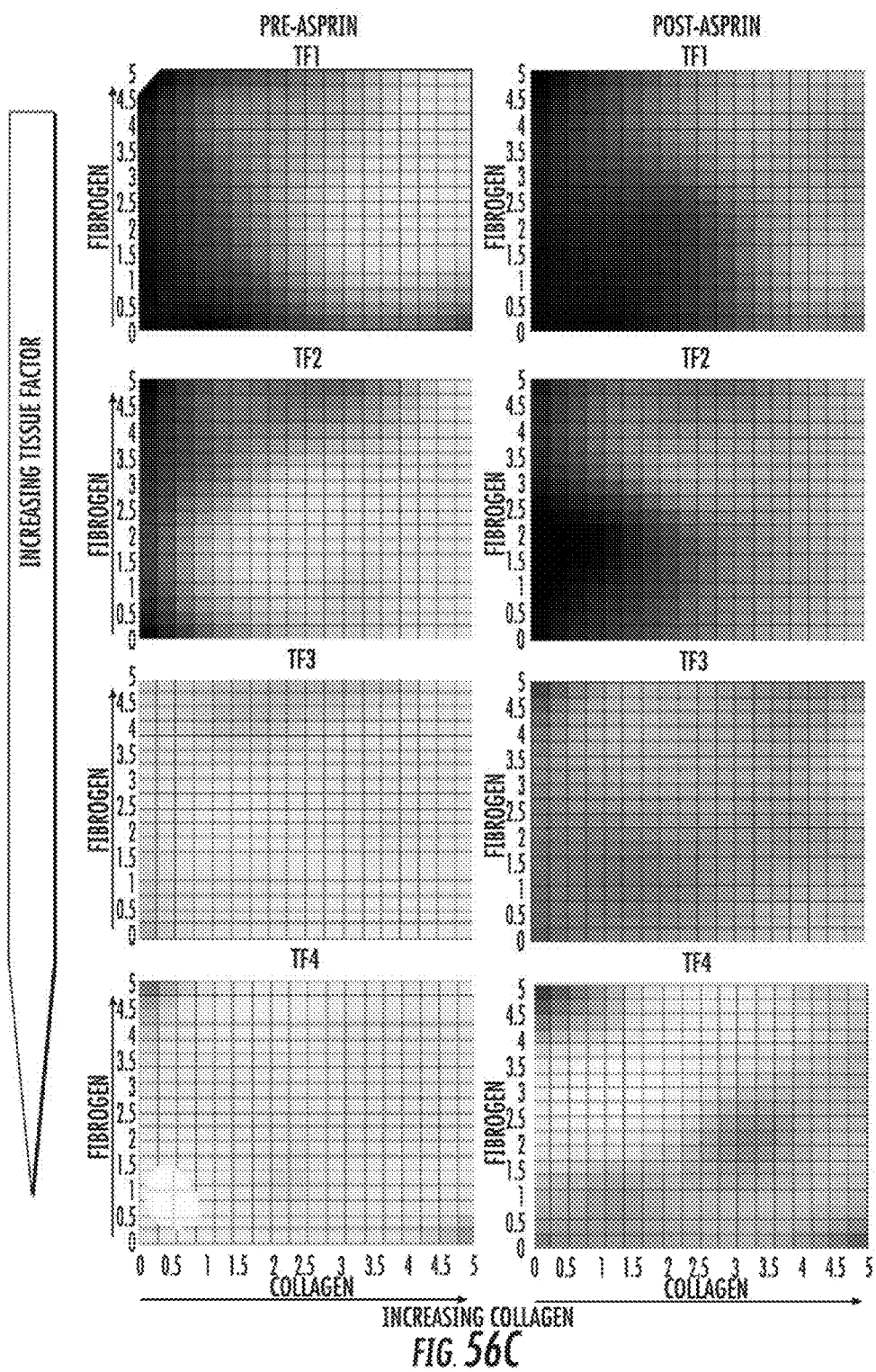
Figure 56D:
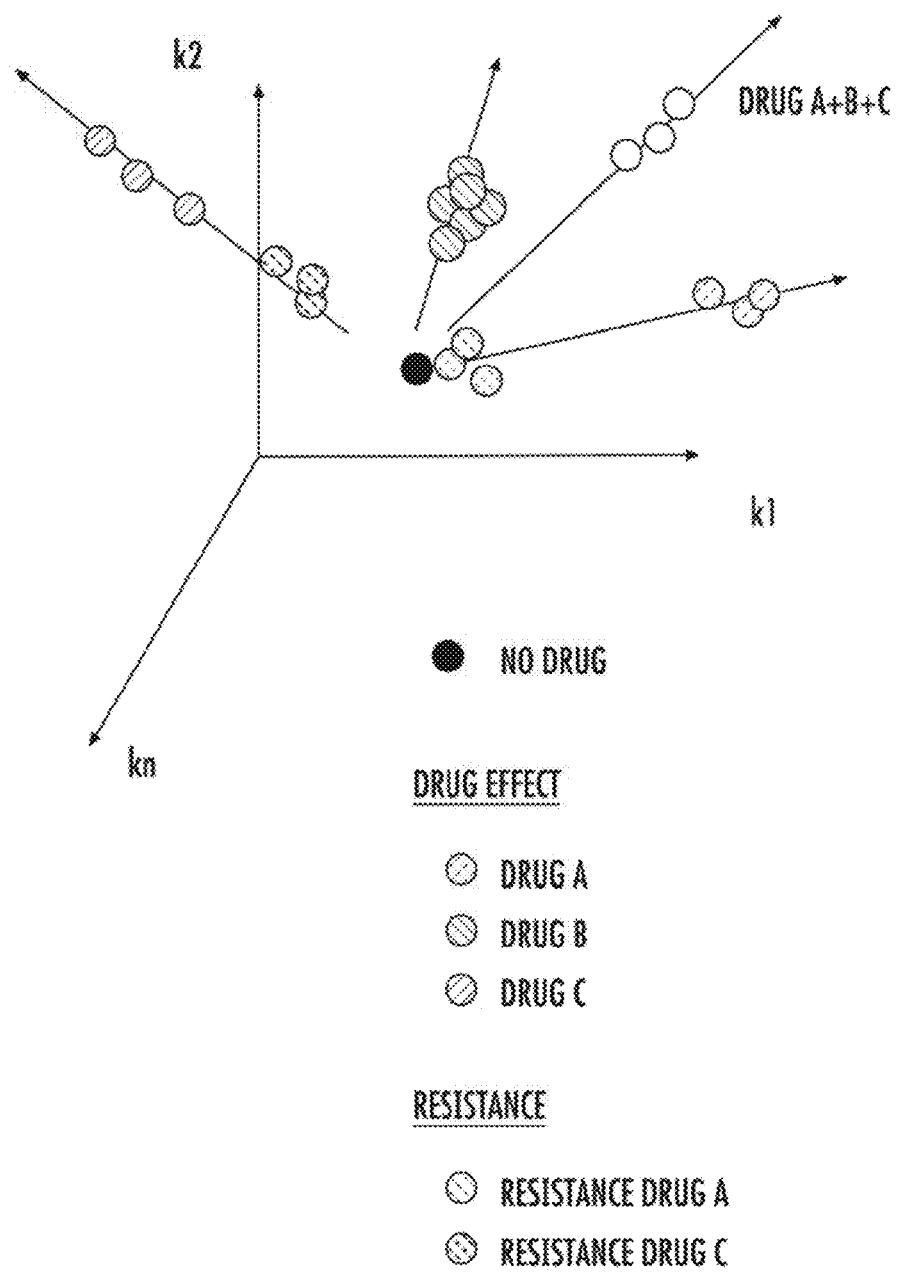

As shown in FIGS. 56A-56D, in addition to providing a rich phenotypic tool, the systems described herein can also be used to track drug responses of individuals. The ability to differentiate different types of drug's effects on hemostatic state may be represented. In FIGS. 56A and 56B, the effect of anticoagulants and antiplatelet agents are graphed. In FIG. 56C, a rich drug state is provided as an alternative to a single readout of drug effect. The rich drug state may be correlated with clinical outcomes and predictive models. FIG. 56D shows a treatment analysis for a patient that takes into account the complex drug regimen and the presence of drug resistance detected in the blood. Such an analysis allows for therapeutic adjustments to be made for an individual patient, based on the predictive models.

In certain embodiments, after analyzing the amount of amount of clot formation in a blood specimen obtained from a patient, the patient is treated to adjust the patient's thrombotic state based on the analyzed amount of clot formation. For example, the assay test systems, apparatus, and methods described herein can be utilized to clinically detect and/or treat any number of thrombotic diseases or other conditions, such as, but not limited to, myocardial infarction, ischemic/embolic stroke, pulmonary embolism, intravascular coagulation, deep vein thrombosis, cancer, peripheral vascular disease, atrial fibrillation/flutter, low ejection fraction, pulmonary hypertension. Additionally, hemorrhagic diseases or conditions can be detected and/or treated, such as, but not limited to, GI bleed, retroperitoneal bleed, femoral hematoma, intra-cranial bleed, pulmonary hemorrhage, or intra-abdominal bleed. Iatrogenically induced conditions can also be identified and/or treated that result from events such as, but not limited to, post-percutaneous intervention, post-endovascular stenting, post-coronary stenting, post heart valve replacement, post atrial arrhythmia ablation, post ventricular arrhythmia ablation, post op for cardiac surgery, post op for non-cardiac surgery, pre-op for cardiac surgery, pre-op for non-cardiac surgery. A patient's thrombotic profile may also be utilized in an inpatient setting to determine the patient's thrombotic acute profile, in an outpatient setting. In some embodiments, thrombotic profiles can be correlated with patient outcomes, allowing specific profiles or ranges of profiles to identify risk for specific outcomes. Similarly, outcome correlation will allow the definition of optimal thrombotic profiles for given diseases or iatrogenic states. For example, conditions such as, but not limited to, myocardial infarction, post percutaneous intervention, stroke, pulmonary embolism, atrial fibrillation, post-endovascular device complications, renal failure, GI bleed, retroperitoneal bleed, femoral bleed, predisposed clotting, heparin induced thrombocytopenia, or intracranial hemorrhage can be identified and the outcomes followed to determine the parameter set or sets which leads to the optimal outcome and/or to the undesirable outcomes.

Systems

Systems and methods for determining one or more thrombotic conditions of a patient are also provided. The systems and methods may include any combination of the apparatus and data analysis features described herein. In one embodiment, a system includes at least one memory that stores computer-executable instructions; and at least one processor configured to access the at least one memory. The at least one processor is configured to execute the computer-executable instructions to: receive a plurality of patient data points from a device which exposes a sample of the patient's blood to multiple exposure conditions in vitro, each patient data point comprising an amount of clot formation and one or more exposure conditions; create a virtual multi-dimensional representation of the plurality of patient data points; and determine, based at least in part on the virtual multi-dimensional representation, one or more thrombotic conditions of the patient. The exposure conditions may include blood contacting surface substrate, chemical agent addition, and blood flow rate.

In certain embodiments, the at least one processor is further configured to execute the computer-executable instructions to: receive a plurality of predictive data points, each predictive data point comprising a blood outcome and one or more exposure conditions; create a virtual multi-dimensional representation of the plurality of predictive data points; and determine, based at least in part on the virtual multi-dimensional representation of the plurality of predictive data points and the one or more thrombotic conditions of the patient, an optimal thrombotic therapy. For example the plurality of predictive data points may be received from a bank of patient data. The bank of patient data may include a locally or remotely stored collection of anonymous patient data points. The patient and predictive data points may include any combination of exposure condition data and clot formation data, and may be tailored based on the specific application and/or patient. In certain embodiments, each patient and/or predictive data point further includes one or more of: patient genotype data, patient age data, patient gender data, patient medical history data, patient medication data, previous patient bleeding event data, previous patient clotting event data, and standard clinical thrombosis test data.

Figure 57:
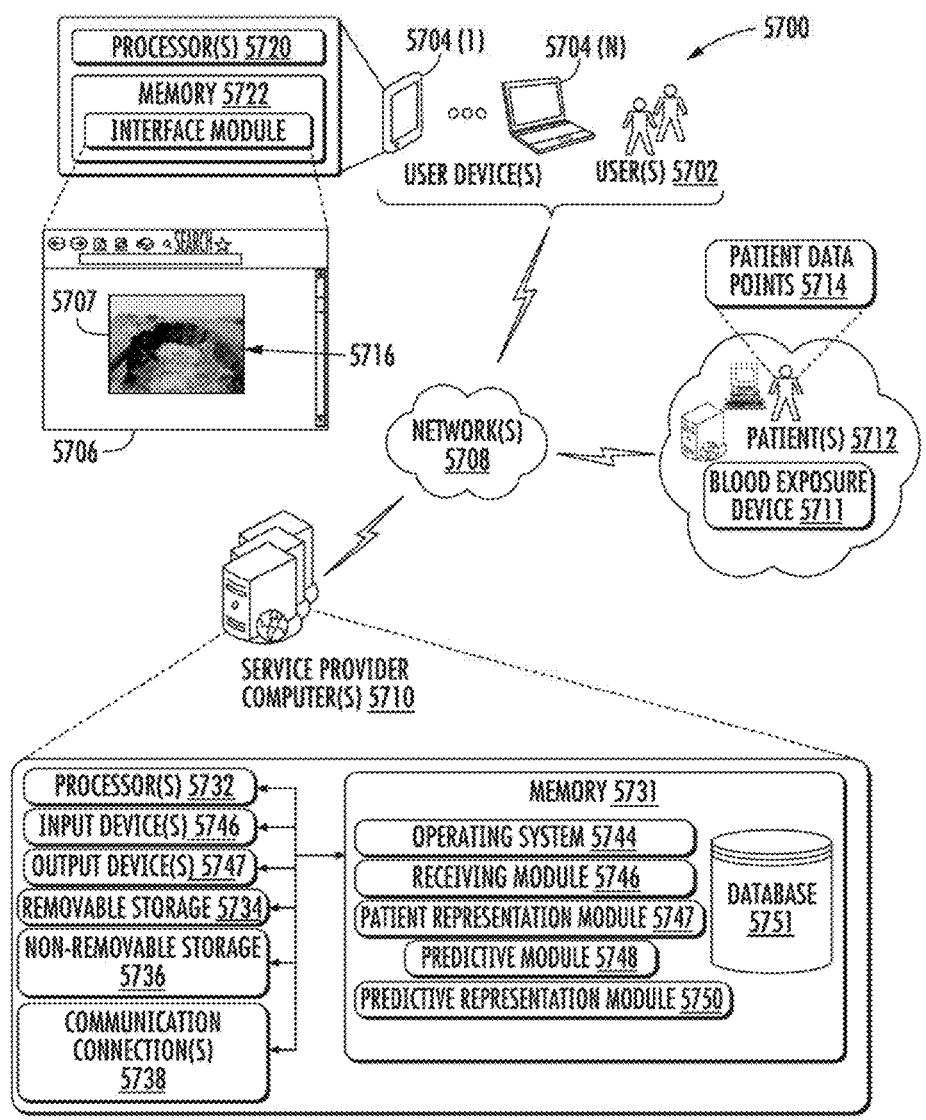
FIG. 57 is a schematic, illustrating one embodiment of a system for determining one or more thrombotic conditions of a patient.

FIG. 57 depicts an illustrative architecture 5700 in which techniques for determining one or more thrombotic conditions of a patient may be implemented. In architecture 5700, one or more users 5702 (e.g., physicians, physician assistants, medical technicians, etc.) may utilize computing devices 5704(1) . . . 5704(N) to access an interface (or website) 5706 that may be provided by, created by, or otherwise associated with a service provider via one or more networks 5708. In some instances, the computing devices (collectively 5704) may be configured to present or otherwise display the interface 5706 to the one or more users 5702. The networks 5708 may include any one or a combination of multiple different types of networks, such as cable networks, the Internet, wireless networks, and other private and/or public networks. While the illustrated example represents users 5702 accessing the interface 5706 over the networks 5708, the described techniques may equally apply in instances where the users 5702 interact with a service provider via a personal computer, a kiosk, or in any other manner. It is also noted that the described techniques may apply in other arrangements (e.g., set-top boxes, etc.), as well as in non-client/server arrangements (e.g., locally stored software applications, etc.).

In some aspects, the interface 5706 may allow the users 5702 to access, receive from, transmit to, or otherwise interact with the service provider via one or more service provider computers 5710. In some examples, the interface 5706 may also allow users to receive, from the service provider computers 5710 over the networks 5708, information associated with one or more patient data points 5714 of a patient 5712. For example, through the interface 5706, the user 5702 may interact with or manipulate the virtual multi-dimensional representation of the plurality of patient data points 5716. Moreover, through the interface 5706, the user 5702 may determine, based at least in part on the virtual multi-dimensional representation 5716, one or more thrombotic conditions of the patient.

The user devices 5704 may be any type of computing devices including, but not limited to, desktop personal computers (PCs), laptop PCs, mobile phones, smart phones, personal digital assistants (PDAs), tablet PCs, set-top boxes, wearable computers, e-readers, web-enabled TVs, cloud-enabled devices and work stations, and the like. In some instances, and as illustrated, each user device 5704 may be equipped with one or more processors 5720 and memory 5722 to store applications and data, such as the virtual multi-dimensional representation 5716 that may be displayed on the interface 5706 and/or enable access to the service provider computers 5710, or elsewhere.

The service provider computers 5710 may be any type of computing device such as, but not limited to, mobile, desktop, and/or cloud computing devices, such as servers. In some examples, the service provider computers 5710 may be in communication with the user devices 5704 via the networks 5708, or via other network connections. The service provider computers 5710 may include one or more servers, perhaps arranged in a cluster, as a server farm, or as individual servers not associated with one another. These servers may be configured to host a website viewable via the interface 5706 or any other Web browser accessible by a user 5702 such as, but not limited to, one or more of the user devices 5704. By way of example and not limitation, suitable computing devices may include personal computers (PCs), servers, server farms, data centers, or any other device capable of storing and executing all or part of the disclosed features.

Still referring to FIG. 57, in one illustrative configuration, the service provider computers 5710 may comprise at least a memory 5731 and one or more processing units (or processor(s)) 5732. The processor(s) 5732 may be implemented as appropriate in hardware, software, firmware, or combinations thereof. Software or firmware implementations of the processor(s) 5732 may include computer-executable or machine-executable instructions written in any suitable programming language to perform the various functions described.

Memory 5731 may store program instructions that are loadable and executable on the processor(s) 5732, as well as data generated during the execution of these programs. Depending on the configuration and type of service provider computers 5710, memory 5731 may be volatile (such as random access memory (RAM)) and/or non-volatile (such as read-only memory (ROM), flash memory, etc.). The service provider computers 5710 may also include additional removable storage 5734 and/or non-removable storage 5736 including, but not limited to, magnetic storage, optical disks, and/or tape storage. The disk drives and their associated computer-readable media may provide non-volatile storage of computer-readable instructions, data structures, program modules, and other data for the computing devices. In some implementations, the memory 5731 may include multiple different types of memory, such as static random access memory (SRAM), dynamic random access memory (DRAM), or ROM.

Memory 5731, removable storage 5734, and non-removable storage 5736 are all examples of computer-readable storage media. For example, computer-readable storage media may include volatile and non-volatile, removable and non-removable media implemented in any method or technology for storage of information such as computer-readable instructions, data structures, program modules, or other data. Additional types of computer storage media that may be present include, but are not limited to, programmable random access memory (PRAM), SRAM, DRAM, RAM, ROM, electrically erasable programmable read-only memory (EEPROM), flash memory or other memory technology, compact disc read-only memory (CD-ROM), digital versatile discs (DVD) or other optical storage, magnetic cassettes, magnetic tape, magnetic disk storage or other magnetic storage devices, or any other medium which can be used to store the desired information and which can be accessed by the server or other computing device. Combinations of any of the above should also be included within the scope of computer-readable media. Alternatively, computer-readable communication media may include computer-readable instructions, program modules, or other data transmitted within a data signal, such as a carrier wave, or other transmission.

The service provider computers 5710 may also contain communication connection(s) 5738 that allow the service provider computers 5710 to communicate with a stored database, another computing device or server, user terminals, and/or other devices on a network. The service provider computers 5710 may also include input device(s) 5740, such as a keyboard, mouse, pen, voice input device, touch input device, etc., and output device(s) 5742, such as a display, speakers, printer, etc.

Turning to the contents of the memory 5731 in more detail, the memory 5731 may include an operating system 5744 and one or more application programs or services for implementing the features disclosed herein including a receiving module 5746, a patient representation module 5747, a predictive module 5748, a predictive representation module 5752, and a database 5751. The receiving module 5746 may be configured to receive information related to the plurality of patient data points. For example, a patient's blood may be run through a blood exposure device 5711 to obtain a set of patient data points 5714. The plurality of patent data points may include a reduced set of data, or may be reduced by a module of memory 5731. The dataset from the blood exposure device 5711 may then be transmitted to the receiving module 5746 via the network 5708, where the virtual multi-dimensional representation 5716 may be analyzed.

In one embodiment, the blood exposure device 5711 is a multi-parameter assay apparatus as described herein. In other embodiments, the blood exposure device 5711 may include conventional blood assays.

The receiving module 5746 may be configured to receive information related to any known or future blood exposure device.

Similarly, memory 5731 may also include a predictive module 5748 configured to receive information related to a plurality of predictive data points. For example, the plurality of predictive data points may be received from a bank of thrombotic information collected from patients. The plurality of predictive data points may include a reduced set of data, or may be reduced by an module of memory 5731.

The memory 5731 may further include a patient representation 5747 module and/or a predictive representation module 5750. These representation modules may be configured to produce a virtual multi-dimensional representation of the patient and predictive data points, respectively. The representation modules may use any of the data analysis techniques described herein, as well as other modeling techniques known to those of ordinary skill in the art to produce a virtual multi-dimensional representation 5716.

Various instructions, methods, and techniques described herein may be considered in the general context of computer-executable instructions, such as program modules, executed by one or more computers or other devices. Generally, program modules include routines, programs, objects, components, data structures, etc., for performing particular tasks or implementing particular abstract data types. These program modules and the like may be executed as native code or may be downloaded and executed, such as in a virtual machine or other just-in-time compilation execution environment. Typically, the functionality of the program modules may be combined or distributed as desired in various embodiments. An implementation of these modules and techniques may be stored on some form of computer-readable storage media.

The architecture 5700 shown in FIG. 57 is provided by way of example only. Numerous other operating environments, system architectures, and device configurations are possible. Accordingly, embodiments of the present disclosure should not be construed as being limited to any particular operating environment, system architecture, or device configuration.

In one embodiment, a method includes receiving, by at least one processer configured to access at least one memory, a plurality of patient data points from a device which exposes a sample of the patient's blood to multiple exposure conditions in vitro, each patient data point comprising an amount of clot formation and one or more exposure conditions; creating, by the at least one processor, a virtual multi-dimensional representation of the plurality of patient data points; and determining, by the at least one processor, based at least in part on the virtual multi-dimensional representation of the plurality of patient data points, one or more thrombotic conditions of the patient. For example, the multi-dimensional representation may include an axis which represents the amount of clot formation, and at least one additional axis, each additional axis representing an exposure condition.

The virtual multi-dimensional representation may be created by any of the methods described herein. For example, the plurality of patient data points may include a reduced data set, the reduced data set being reduced from a raw data set comprising the exposure conditions and the amount of clot formation. The step of receiving a plurality of patient data points may include reducing, by the at least one processor, the raw data set into the plurality of patient data points.

In certain embodiments, the method also includes receiving, by the at least one processer, a plurality of predictive data points, each predictive data point comprising a blood outcome and one or more exposure conditions; creating, by the at least one processor, a virtual multi-dimensional representation of the plurality of predictive data points; and determining, by the at least one processor, an optimal thrombotic therapy, based at least in part on the virtual multi-dimensional representation of the plurality of predictive data points and the one or more thrombotic conditions of the patient. For example, determining an optimal thrombotic therapy may include determining predictive positive outcomes, predictive adverse outcomes, and predictive risk prone states, based at least in part on the virtual multi-dimensional representation of the plurality of predictive data points, and associating the one or more thrombotic conditions with one or more of: the predictive positive outcomes, the predictive adverse outcomes, and the predictive risk prone states.

Figure 58:
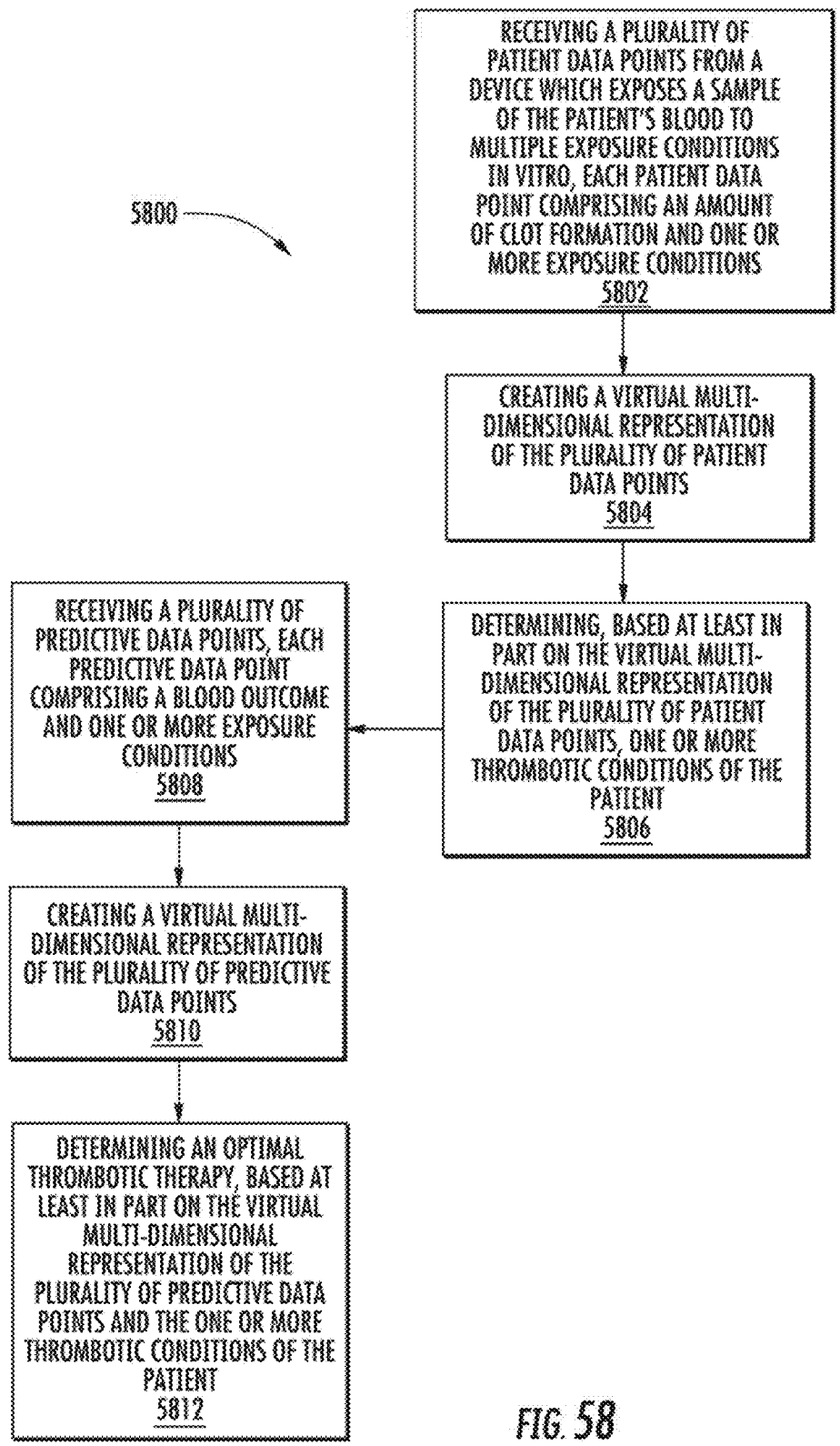
FIG. 58 is a process flow diagram, illustrating one embodiment of a method for determining one or more thrombotic conditions of a patient.

FIG. 58 illustrates one embodiment of a flow diagram of a method for determining one or more thrombotic conditions of a patient. In one embodiment, the illustrative service provider computers 5710 of FIG. 57 and/or locally stored software applications and/or one or more modules, alone or in combination, may perform the described operations of the methods. In one embodiment, a method 5800 may begin at block 5802, in which the method 5800 may include receiving a plurality of patient data points from a device which exposes a sample of the patient's blood to multiple exposure conditions in vitro, each patient data point comprising an amount of clot formation and one or more exposure conditions. For example, the device may be a multi-parameter assay apparatus as described herein, or any other blood testing device known in the art. At block 5804, the method 5800 may include creating a virtual multi-dimensional representation of the plurality of patient data points. For example, the virtual representation may be made by any of the data analysis or modeling techniques described herein. At block 5806, the method 5800 may include determining, based at least in part on the virtual multi-dimensional representation of the plurality of patient data points, one or more thrombotic conditions of the patient. At block 5808, the method 5800 may include receiving a plurality of predictive data points, each predictive data point comprising a blood outcome and one or more exposure conditions. For example, the predictive data points may be received from a local or remote bank of data. At block 5810, the method 5800 may include creating a virtual multi-dimensional representation of the plurality of predictive data points. At block 5812, the method 5800 may include determining an optimal thrombotic therapy, based at least in part on the virtual multi-dimensional representation of the plurality of predictive data points and the one or more thrombotic conditions of the patient.

For example, determining an optimal therapy may include correlating patient data with good (e.g., healthy, safe) and adverse (e.g., clotting events, bleeding) clinical outcomes. Using predictive algorithms derived from the collection of predictive data, when data from a new patient is collected, their risk profiles can be assessed and appropriate therapeutic interventions can be made in real time. After data is obtained for full condition sets and the important factors of particular clinical scenarios determines (e.g., patients undergoing percutaneous coronary intervention, coronary artery bypass grafting, other surgical procedures or biopsies, have conditions such as deep vein thrombosis, pulmonary embolism, stroke, atrial fibrillation, hematological conditions), tailored test apparatus can be produced.

Illustrative systems and methods are described for analyzing and determining one or more thrombotic conditions of a patient. Some or all of these systems and methods may, but need not, be implemented at least partially by architectures such as those shown in FIG. 57.

Publications cited herein and the materials for which they are cited are specifically incorporated by reference. Modifications and variations of the methods and devices described herein will be obvious to those skilled in the art from the foregoing detailed description. Such modifications and variations are intended to come within the scope of the appended claims.

We claim:

1. A system for determining one or more thrombotic conditions of a patient, comprising:
   at least one memory that stores computer-executable instructions; and
   at least one processor configured to access the at least one memory, wherein the at least one processor is configured to execute the computer-executable instructions to:
   receive a plurality of patient data points from a device which exposes a sample of the patient's blood to multiple exposure conditions in vitro, each patient data point comprising an amount of clot formation and one or more exposure conditions, wherein the one or more exposure conditions are selected through a quasi-random process that comprises a Sobol sequence;
   create a virtual multi-dimensional representation of the plurality of patient data points; and
   determine, based at least in part on the virtual multi-dimensional representation, one or more thrombotic conditions of the patient,
   wherein the exposure conditions comprise blood contacting surface substrate, chemical agent addition, and blood flow rate.

2. The system of claim 1, wherein the at least one processor is further configured to execute the computer-executable instructions to:
   receive a plurality of predictive data points, each predictive data point comprising a blood outcome and one or more exposure conditions;
   create a virtual multi-dimensional representation of the plurality of predictive data points; and
   determine, based at least in part on the virtual multi-dimensional representation of the plurality of predictive data points and the one or more thrombotic conditions of the patient, an optimal thrombotic therapy.

3. The system of claim 1, further comprising the device which exposes a sample of the patient's blood to multiple exposure conditions in vitro, wherein the device comprises:
   a plurality of test receptacles adapted to receive a sample of blood, wherein blood contacting surfaces of a first subset of the plurality of test receptacles are coated with a first surface substrate, and blood contacting surfaces of a second subset of the plurality of test receptacles are coated with a second surface substrate which is different from the first surface substrate;
   at least one flow generating mechanism in fluid communication with the plurality of test receptacles, wherein the at least one flow generating mechanism is configured to generate a first blood flow rate through a third subset of the plurality of test receptacles and a second blood flow rate which is different from the first blood flow rate through a fourth subset of the plurality of test receptacles; and
   a clot detector configured to analyze an amount of clot formation, if any, that occurs within the sample of blood in each of the test receptacles.

4. The system of claim 3, wherein the device further comprises one or more blood chambers in fluid communication with the plurality of test receptacles, each blood chamber configured to introduce a chemical agent into the sample of blood therein.

5. The system of claim 3, wherein the at least one flow generating mechanism or at least one of the test receptacles is configured to introduce a chemical agent into the sample of blood therein.

6. The system of claim 3, wherein the at least one flow generating mechanism comprises a volume displacement device.

7. The system of claim 6, wherein:
   the volume displacement device comprises syringe pumps, each syringe pump containing a piston having a volume, and
   the blood flow rates are dependent upon the volumes of the pistons or upon rates of actuation of the syringe pumps.

8. The system of claim 6, wherein:
- the volume displacement device comprises deformable chambers, each deformable chamber having a volume, and
- the blood flow rates are dependent upon the volumes of the deformable chambers or upon rates of compression of the deformable chambers.

9. The system of claim 6, wherein the volume displacement device comprises a pump operable to generate (i) a positive pressure which is effective to push blood through or into the test receptacles, or (ii) a negative pressure which is effective to pull blood through or into the test receptacles.

10. A system for determining one or more thrombotic conditions of a patient, comprising:
- at least one memory that stores computer-executable instructions; and
- at least one processor configured to access the at least one memory, wherein the at least one processor is configured to execute the computer-executable instructions to:
  - receive a plurality of patient data points from a device which exposes a sample of the patient's blood to multiple exposure conditions in vitro, each patient data point comprising an amount of clot formation and one or more exposure conditions;
  - create a virtual multi-dimensional representation of the plurality of patient data points; and
  - determine, based at least in part on the virtual multi-dimensional representation, one or more thrombotic conditions of the patient,
- wherein the exposure conditions comprise blood contacting surface substrate, chemical agent addition, and blood flow rate.

11. The system of claim 10, wherein the at least one processor is further configured to execute the computer-executable instructions to:
- receive a plurality of predictive data points, each predictive data point comprising a blood outcome and one or more exposure conditions;
- create a virtual multi-dimensional representation of the plurality of predictive data points; and
- determine, based at least in part on the virtual multi-dimensional representation of the plurality of predictive data points and the one or more thrombotic conditions of the patient, an optimal thrombotic therapy.

12. The system of claim 10, further comprising the device which exposes a sample of the patient's blood to multiple exposure conditions in vitro, wherein the device comprises:
- a plurality of test receptacles adapted to receive a sample of blood, wherein blood contacting surfaces of a first subset of the plurality of test receptacles are coated with a first surface substrate, and blood contacting surfaces of a second subset of the plurality of test receptacles are coated with a second surface substrate which is different from the first surface substrate;
- at least one flow generating mechanism in fluid communication with the plurality of test receptacles, wherein the at least one flow generating mechanism is configured to generate a first blood flow rate through a third subset of the plurality of test receptacles and a second blood flow rate which is different from the first blood flow rate through a fourth subset of the plurality of test receptacles; and
- a clot detector configured to analyze an amount of clot formation, if any, that occurs within the sample of blood in each of the test receptacles.

13. The system of claim 12, wherein the device further comprises one or more blood chambers in fluid communication with the plurality of test receptacles, each blood chamber configured to introduce a chemical agent into the sample of blood therein.

14. The system of claim 12, wherein the at least one flow generating mechanism or at least one of the test receptacles is configured to introduce a chemical agent into the sample of blood therein.

15. The system of claim 12, wherein the at least one flow generating mechanism comprises a volume displacement device.

16. The system of claim 15, wherein:
- the volume displacement device comprises syringe pumps, each syringe pump containing a piston having a volume, and
- the blood flow rates are dependent upon the volumes of the pistons or upon rates of actuation of the syringe pumps.

17. The system of claim 15, wherein:
- the volume displacement device comprises deformable chambers, each deformable chamber having a volume, and
- the blood flow rates are dependent upon the volumes of the deformable chambers or upon rates of compression of the deformable chambers.

18. The system of claim 15, wherein the volume displacement device comprises a pump operable to generate (i) a positive pressure which is effective to push blood through or into the test receptacles, or (ii) a negative pressure which is effective to pull blood through or into the test receptacles.

* * * * *